(12) United States Patent
Khouri

(10) Patent No.: US 11,318,009 B2
(45) Date of Patent: May 3, 2022

(54) SURGICAL TOOLS AND METHODS FOR THEIR USE

(71) Applicant: Roger Khouri, Key Biscayne, FL (US)

(72) Inventor: Roger Khouri, Key Biscayne, FL (US)

(73) Assignee: Lipocosm, LLC, Key Biscayne, FL (US)

( * ) Notice: Subject to any disclaimer, the term of this patent is extended or adjusted under 35 U.S.C. 154(b) by 664 days.

(21) Appl. No.: 13/884,431

(22) PCT Filed: May 6, 2013

(86) PCT No.: PCT/US2013/039675
§ 371 (c)(1),
(2) Date: May 9, 2013

(87) PCT Pub. No.: WO2013/166484
PCT Pub. Date: Nov. 7, 2013

(65) Prior Publication Data
US 2015/0157450 A1 Jun. 11, 2015

Related U.S. Application Data

(60) Provisional application No. 61/849,959, filed on Feb. 5, 2013, provisional application No. 61/643,023, filed on May 4, 2012.

(51) Int. Cl.
*A61F 2/12* (2006.01)
*A61B 17/04* (2006.01)
(Continued)

(52) U.S. Cl.
CPC ............ *A61F 2/12* (2013.01); *A61B 17/0401* (2013.01); *A61B 17/0482* (2013.01);
(Continued)

(58) Field of Classification Search
CPC ...... A61F 2/12; A61F 13/14; A61B 17/32053; A61B 17/3417; A61B 17/3494;
(Continued)

(56) References Cited

U.S. PATENT DOCUMENTS

| 55,775 A | 6/1866 | Klee |
|---|---|---|
| 60,917 A | 1/1867 | Brown |

(Continued)

FOREIGN PATENT DOCUMENTS

| CH | 396 311 A | 7/1965 |
|---|---|---|
| EP | 2 377 475 A1 | 10/2011 |

OTHER PUBLICATIONS

Extended European Search Report issued in European Application No. 13785140.8 dated Feb. 25, 2016 (6 pages).

*Primary Examiner* — Todd J Scherbel
(74) *Attorney, Agent, or Firm* — Neil D. Gershon

(57) ABSTRACT

Surgical tools and kits for performing methods include a grommet with cylindrical shaft, cutting tip, annular flange with suture retaining anchoring fixture; a grommet jig for extending between adjacent grommets and guiding a needle therebetween; a family of needles with single and double pointed ends, reinforced eyelets, stops to limit inadvertent exiting, double shaft construction with a longitudinal gap and sharpened, slicing ends, including a "J" shape embodiment; a bone anchor with ring to secure sutures about a patient's clavicle; a tissue dissector having radially extending cones to nick taut connecting tissues; a tissue rasp having a series of crisscrossing grooves along an end; a tissue mesher comprising one or more blocks having a matrix of holes for clamping a plurality of needles and a supporting framework; and a kit device and a method of surgically inserting an internal mesh brassiere under the breast skin.

17 Claims, 51 Drawing Sheets

(51) Int. Cl.
*A61B 17/06* (2006.01)
*A61B 17/20* (2006.01)
*A61B 17/34* (2006.01)
*A61K 35/16* (2015.01)
*A61B 17/3205* (2006.01)
*A61F 13/14* (2006.01)
*A61B 17/00* (2006.01)
*A61B 17/322* (2006.01)
*A61B 90/00* (2016.01)

(52) U.S. Cl.
CPC ...... *A61B 17/06066* (2013.01); *A61B 17/205* (2013.01); *A61B 17/32053* (2013.01); *A61B 17/3417* (2013.01); *A61B 17/3494* (2013.01); *A61K 35/16* (2013.01); *A61B 90/02* (2016.02); *A61B 2017/0023* (2013.01); *A61B 2017/00792* (2013.01); *A61B 2017/00796* (2013.01); *A61B 2017/044* (2013.01); *A61B 2017/0414* (2013.01); *A61B 2017/0608* (2013.01); *A61B 2017/0609* (2013.01); *A61B 2017/06042* (2013.01); *A61B 2017/06047* (2013.01); *A61B 2017/06071* (2013.01); *A61B 2017/3225* (2013.01); *A61B 2017/3454* (2013.01); *A61F 13/14* (2013.01); *A61F 2250/0067* (2013.01)

(58) Field of Classification Search
CPC ......... A61B 17/0482; A61B 17/06066; A61B 17/0401; A61B 17/205; A61B 2017/0023; A61B 2017/3454; A61B 2017/0608; A61B 2017/00792; A61B 2017/06042; A61B 2017/00796; A61B 2017/0414; A61B 2017/0609; A61B 2017/06047; A61B 2017/044; A61B 2017/06071; A61B 2017/3225; A61B 90/02; A61B 17/06; A61B 17/06004; A61B 17/34; A61B 17/3468; A61B 17/3478; A61B 2017/06009; A61B 2017/06019; A61B 2017/06023; A61B 2017/06028; A61B 2017/06057; A61B 2017/06085; A61K 35/16; D05B 85/00; D05B 85/003; D05B 85/006; D05B 85/14

See application file for complete search history.

(56) References Cited

U.S. PATENT DOCUMENTS

| | | | |
|---|---|---|---|
| 273,702 A | 3/1883 | Bennett | |
| 693,554 A | 2/1902 | Langstaff | |
| 1,067,368 A | 7/1913 | Ogier | |
| 4,781,190 A * | 11/1988 | Lee | A61B 17/06004 606/139 |
| 5,250,067 A | 10/1993 | Gelfer et al. | |
| 5,336,239 A * | 8/1994 | Gimpelson | A61B 17/0469 606/223 |
| 5,478,353 A * | 12/1995 | Yoon | A61B 17/0057 606/104 |
| 5,935,138 A * | 8/1999 | McJames, II | A61B 17/06066 606/139 |
| 5,961,535 A | 10/1999 | Rosenberg et al. | |
| 5,964,729 A | 10/1999 | Choi et al. | |
| 6,030,404 A | 2/2000 | Lawson et al. | |
| 6,063,094 A | 5/2000 | Rosenberg | |
| 6,551,338 B1 | 4/2003 | Chiu et al. | |
| 6,660,018 B2 | 12/2003 | Lum et al. | |
| 6,835,184 B1 | 12/2004 | Sage et al. | |
| 7,056,324 B2 | 6/2006 | Stough | |
| 7,186,235 B2 | 3/2007 | Martin et al. | |
| 7,316,671 B2 | 1/2008 | Lastovich et al. | |
| 7,419,481 B2 | 9/2008 | Trautman et al. | |
| 7,618,429 B2 | 11/2009 | Mulholland | |
| 8,257,379 B2 | 9/2012 | Lee | |
| 8,267,889 B2 | 9/2012 | Cantor et al. | |
| D687,550 S | 8/2013 | Moeckly et al. | |
| D687,551 S | 8/2013 | Moeckly et al. | |
| 8,545,489 B2 | 10/2013 | Giovannoli | |
| 8,551,098 B2 | 10/2013 | Shimko et al. | |
| 2003/0050530 A1* | 3/2003 | Neisz | A61B 17/0401 600/29 |
| 2005/0182446 A1* | 8/2005 | DeSantis | A61B 17/06066 606/222 |
| 2007/0055179 A1 | 3/2007 | Deem et al. | |
| 2007/0276425 A1 | 11/2007 | Kim et al. | |
| 2008/0119781 A1 | 5/2008 | King | |
| 2009/0054911 A1* | 2/2009 | Mueller | A61B 17/0401 606/139 |
| 2009/0125050 A1 | 5/2009 | Dixon | |
| 2010/0137679 A1* | 6/2010 | Lashinski | A61B 17/0401 600/37 |
| 2011/0130773 A1* | 6/2011 | Saliman | A61B 17/0469 606/145 |
| 2011/0251602 A1 | 10/2011 | Anderson et al. | |
| 2011/0301642 A1* | 12/2011 | White | A61B 17/06066 606/223 |
| 2011/0319920 A1 | 12/2011 | Kikkawa et al. | |
| 2012/0123471 A1* | 5/2012 | Woodard, Jr. | A61B 17/06004 606/223 |
| 2012/0209300 A1* | 8/2012 | Torrie | A61B 17/0469 606/148 |
| 2012/0277766 A1* | 11/2012 | Ferree | A61F 2/442 606/144 |
| 2013/0150878 A1 | 6/2013 | Church | |
| 2014/0039523 A1 | 2/2014 | Austen | |

* cited by examiner round stop, one or both ends

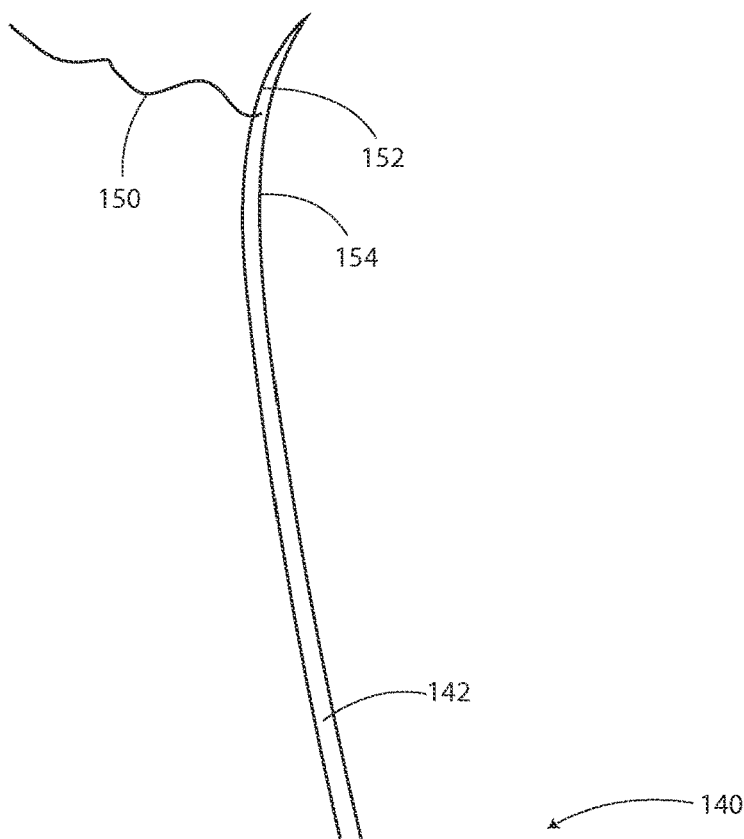
FIG. 18
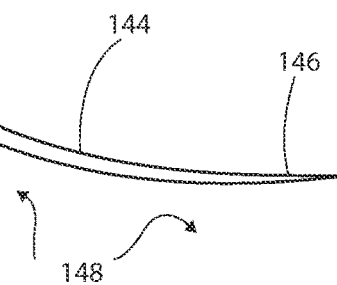

SURGICAL TOOLS AND METHODS FOR THEIR USE

BACKGROUND AND SUMMARY OF THE INVENTION

The inventor has conceived of, reduced to practice, and patented, many inventions related to the augmentation of soft tissue including especially the augmentation and reconstruction of the female breast. Several examples of his patented inventions include the following: U.S. Pat. Nos. 5,536,233; 5,662,583; 5,676,634; 5,695,445; 5,701,917; 6,083,912; 6,478,656; 6,500,112; 6,641,527; 6,699,176; and most recently U.S. Pat. No. 8,066,691, along with other patent applications under prosecution such as 20080167613, 20100137841, and 20100160900, the disclosures of all the foregoing being incorporated herein by reference. As his investigative work has continued, he has continued to invent tools and methods for their use which enable him to implement new surgical procedures which provide strikingly improved results for his patients over existing practices and procedures implemented by other surgeons in this field. Many of these may be implemented together and thus provide the basis for them to be provided in a kit, either single use or for repeated use with one or more patients. Similarly, several of these may be implemented not only together but also in conjunction with the tools and methods of his earlier work as exemplified in his patent filings mentioned above. Furthermore, several of inventions disclosed herein, while implemented by the inventor and having been found to work, have alternate constructions or embodiments that the inventor has conceived of and which are contemplated to also work and may even be more desirable for commercialization. These tools and appliances may be briefly summarized as follows.

A number of the inventions described, infra, are useful in a particular breast augmentation/reconstruction procedure or a procedure for the correction of breast deformities, whether acquired or congenital, which will be described in greater detail below as part of the Detailed Description of the Preferred Embodiments and illustrated in the drawings included herein. The inventor has coined the term Reverse Abdominoplasty and Lipo-Filling (RAFT) to describe this procedure which is a minimally invasive alternative method of breast reconstruction that utilizes the anterior abdominal apron as a reverse abdominoplasty flap. The RAFT procedure was initially developed as a means of salvaging the failed implant augmentation and reconstruction procedures and the inventor later realized that it was also a very useful means of augmenting the small breast, of correcting the breast deformities, or treating scars or chest wall wound defects, and of reconstructing mastectomy defects. Essentially, it comprises a purse string suture that can be threaded through the dermis/subdermal tissue layers of the abdominal skin apron that is to be advanced and incorporated into the breast, and a mechanism to suspended this suture to the clavicle to secure the advancement, and to tighten it in order to induce a mushrooming out projection of the breast and to sculpt a pleasing inframammary and lateral breast folds. The abdominal apron to be advanced is usually first filled with a tumescent fluid and liposuctioned to loosen it and deflate it. This is followed by extensive percutaneous dissection to create an interface to ensure long term maintenance of the suspension and the repositioned tissue independent of the suture. The advanced abdominal and lateral thoracic flaps by themselves add significant volume to the breast mound. Lipofilling the breast and the purse-stringed advanced flaps adds more volume and shape to created breast mound. Percutaneously meshing the deeper retaining structures that restrict the advancement of the abdominal apron expands it (similar to a skin graft mesh expansion pattern) and alleviates the tension. It also serves to divide the cutaneous perforator nerves that would normally cause pain if they are stretched but usually not if they are simply divided. As shown in FIG. 41, use of the tissue mesher allows for further advancement of the abdominal skin apron. The reconstruction is with local breast-like tissue, is incisionless, minimally invasive and patient friendly. It is considered by the inventor as a first choice reconstructive option that is also available when all else has failed or in some cases not even tried. Though most useful for the breast, the same principle of tissue advancement and tightening can be applied to other anatomic areas such as the jowls of the aging face and the overhang of the panniculus or other anatomic structures that migrate downward under the effect of gravity with aging and volume loss.

The reconstruction of a woman's breast is an important step towards her recovery after mastectomy or following other disfiguring breast pathologies. The TRansverse Abdominoplasty Musculocutaenous flap or TRAM flap as it is most commonly called, is one of the most common methods of achieving this purpose. It consists of performing an abdominoplasty (tummy tuck) and then transferring the harvested excess abdominal tissue to the chest as a flap. Unfortunately, the TRAM flap is a major surgical procedure that carries a substantial amount of morbidity, inflicts multiple incisions and has a significant failure and complication rate. While the abdominal tissue is the best available substitute for the restoration of a breast mound, a more patient friendly, less invasive and less complication prone method of transferring this tissue to the breast would provide a significant societal benefit.

While both the TRAM and the novel method described herein take advantage of the laxity of the abdominal apron, compared to the TRAM where the tissue is totally cut out of the lower abdomen and brought up to the chest, this device allows the lax abdominal tissue to slide up, to be secured in its new position and to be molded into a breast without having to cut it out and without any major incision. The invention herein preferably comprises a kit for use by a surgeon to perform a surgical procedure to transfer the abdominal tissue to the chest by sliding it up and fixing it in place with a purse string of suture, and the fashioning of that tissue into a breast mound by filling it with a small implant or with a suitable fluid such as aspirated fat. The kit components provide means of:

1—Mobilizing the laxity of the upper abdominal tissue to slide it up to the breast, 2—Inserting a suspension suture that is threaded from the level of the upper chest or the clavicle, down to the upper abdominal tissue, where it can grab its dermis/subcutaneous tissue in a purse string fashion and then thread it back up to the level of the upper chest or clavicle to close the loop.

3—Using that suspension suture to grab the abdominal tissue, pull it up and suspend it to the clavicle (collar bone) with a bone anchor.

4—Tightening the suture to pucker the purse string into a dome and firmly securing the looped suture to the bone anchoring device using a suture locking mechanism 5—Percutaneously dividing the fibers that restrict advancement of the skin just cephalic (above) and caudal (below) to the purse string to allow a "mushrooming effect" and fully define the breast overhang and the breast fold.

6—Without making a skin incision and only through a multitude of non-scar inducing punctures, cutting the deep tissues at the level of the new fold to define it and to induce it to permanently heal and adhere in that new location 7—Loosening the resultant tightness of the rest of the abdominal tissue by mesh expanding it and dividing the restrictive vertical retaining fibers and perforators as shown in FIG. 41.

8—Filling the advanced tissue with fat graft and percutaneously re-orienting its fibrous framework in order to correct any puckering, iron out wrinkles and treat the "double bubble" deformities.

The steps described above are not necessarily performed in the order presented.

The kit components could be single use, sterile, disposable, or more permanent re-usable & re-sterilizable. Some of these components could come inside a box kit for a specific application or can be made available as individual devices. While, as known to the inventor, each of these components is novel and serves a specific purpose for use in performing a RAFT breast reconstruction, they are most likely useful in other related or unrelated medical applications such as the rejuvenating face lift and other procedures that benefit from advancing tissue beyond what the normal tissue laxity and mobility permits.

One of these inventions may best be characterized as a temporary bra, to be used, as appropriate, throughout the surgical process but most preferably during surgery and then post-operatively to maintain the shape and to prevent any recoil of the swollen tissue. This bra is sterile and may be applied during surgery. The bra is preferably transparent, sufficiently pliant to conform to the breast surface and then preferably molded to the desired shape as it is preferably strongly adhered to the skin. The adhesive component may be inherent to the bra or shaping device material so that it adheres upon initial contact or the shaping device may not be initially adherent as this will allow the breast (or other anatomic region) to be appropriately positioned inside the device and then, when appropriately arranged inside the shaping bra, the adhesive component might be added or made to become active. The device may also have suspension straps or a cap bonnet to overcome the effect of gravity. It may have a pattern of markings on it to mark the path of the sutures and the position of the grommets (see below) to guide the surgeon as he performs a surgical lifting/shaping/augmentation/reconstruction on the breast. This bra may also include a rib like structural reinforcement to help hold its shape as it is worn by the patient. Alternatively, the shaping device itself might be made of a material that hardens upon exposure to air or to a catalyst, or a hardening component can be added to it as desired by the surgeon.

To further aid the surgeon as he threads sutures through the breast, the inventor has developed several grommet designs which fit through the dermal tissues (and bra, if used) to identify and isolate exit points for the sutures which aids in not only avoiding damage to any superficial subdermal fibers and invagination dimpling of the skin when these superficial fibers are inadvertently held by the suture and driven inside by its tightening, but also assists in creating an internal weave set at a predetermined depth to support and lift the breast in a novel surgical procedure developed by the inventor.

Thanks to the grommet, a surgeon can pass the entire needle out through the skin, then pass the thread through the grommet, secure the grommet in place through and over the skin puncture site, and re-enter with the single pointed needle through the same entrance path to avoid grabbing dermal fibers and thus grab only the deep tissues and avoid the unwanted dimpling effect which would potentially be created in the dermal tissues adjacent the exit/entry point. The grommet could thus be a "salvage" for the double pointed needle as re-entry of the needle through a grommet threaded over the thread that has exited will prevent that suture loop from grabbing unwanted superficial tissues.

The grommet provides an elegant alternative to the double pointed needle as may otherwise be required. A grommet can be inserted first through the skin around the area that needs to be suspended and then two separate needles at the ends of the same thread can be passed through, each circumscribing a separate path. Removing the grommet and tightening the suture buries the loop deep inside the tissue (at the predetermined depth of the grommet) without grabbing dermal fibers and puckering the skin.

In addition, having two separate thread loops, each with a different path, exit through the same grommet allows these loops to interlock and create a basket weave that can be driven deeper inside the breast (or other anatomic areas chosen for the procedure) without puckering the skin and without leaving a significant scar. A judiciously placed pattern of grommets and thread paths is a unique and novel method of percutaneously weaving a net-like or basket weave like supportive and shaping mesh pattern deep inside the tissues without making any major incision, only tiny puncture sites that tend to heal without a significant scar. To prevent an unwanted exit through the skin and keep the grommet securely in and across the skin opening while the needles and threads are coming in and out, the grommet preferably has a structure to hold it in place. To this effect, the grommet may have threads like a screw so that it may be screwed in place. Alternatively, the grommet could simply have a button like or barb like design on the entry side that prevents its unintended withdrawal, or include a retractable, telescoping "fanning out" umbrella that would open on the undersurface of the skin to hold it tightly in place. This additional locking mechanism would enter the skin through the same hole, however, for the sake of keeping the hole at minimal size, the anchoring mechanism could be spaced about a top hat or flange in the grommet that grabs the skin through separate fine needle sticks, fine clamps, a staple like mechanism or even sutures. As yet another feature of the grommet, a cleat or spiral hook may be provided to allow a suture to stay outside and be anchored and then reintroduced into the patient's breast after interlocking it with another loop that also exited through the same grommet so as to create the basket weave internal support bra procedure described, infra and in other of the inventor's patent filings.

As an adjunct to the grommet invention, the inventor has also conceived of a jig or guiding mechanism that can be attached between two or more adjacent grommets and used to physically guide the needle as it is inserted and extends between the two grommets. A pattern of jigs can be affixed to the supportive bra or other shape forming device to guide the entire process of inserting and weaving the mesh. This assists the surgeon in the delicate procedure of guiding the needle through the deep tissues and then the intradermal tissues of the patient as one of the surgical procedures described herein is performed. Again, although not strictly required, it helps transform the process from one of art to science to thereby improve chances for a successful procedure.

The inventor has conceived of and developed a number of needle devices to aid him in several of his novel surgical procedures. Among these are a needle that can be driven from a distance to enter from one site, grab and secure tissues that are relatively distant, and return to the original entrance point while keeping the suture deep within the body tissue without grabbing of any intervening skin and without causing any unwanted puckering. This requires a needle that is significantly different than the standard surgical needles that are used to stitch together wounds or immediately exposed adjacent structures.

The needle preferably has a sharp point at only one end as long as long as the procedure allows it to come in and out only through "mature" puncture holes along its looped course. Mature holes may be for example liposuction cannula entry holes that have their subdermal fibers destroyed by the repeated passage of the cannula such that an in & out passage of the needle through this widely dissected path is not likely to catch unwanted fibers along the way. In a surgical procedure such as the fat graft augmentation typically performed on a patient with excess abdominal fat, a liposuction procedure to harvest the fat for use in the breast augmentation would provide these mature holes, for example.

Most prior art surgical needles have pointed tips that are round in cross section. The inventor's needle invention preferably includes cutting tips; needle tips having a cross section with sharp cutting edges at the pointed end to slice through the dermis. (Surgical needles are normally classified as having either round or cutting tips.) The needle here preferably needs to have a extremely sharp and long beveled cutting tip that has preferably an even sharper finer bevel to slice through the arcuate long dermal path when it is used for the purse string procedure described, infra). Furthermore the orientation or needle cutting tips should ideally be such that the cuts are deep and along the inner curve and not up, as explained infra.

Another needle embodiment is preferably double pointed. (Though for the RAFT procedure only one of the pointed tips is preferably very fine and cutting, the other, for the purpose of safer manipulation is preferably round or with a shorter cutting bevel). Double pointed needles are capable of being driven along a complex stich course to grab and tie together deep and far tissues (as contrasted with adjacent tissues as is typically done in the prior art) without the attached thread ever having to exit through the skin which tends to cause unwanted dimpling. A classic prior art needle (sharp at one end and blunt with a thread through an eye at the other) can only be driven through the tissue for a short distance, and this through a relatively straight course, or one that circumscribes only a limited arc. To go through a lengthy course or to complete a loop and come back to its original entry site, a standard needle has to exit the body every few centimeters, and be driven back again through the skin to continue and complete the path. With this process, as dictated by the typical prior art needle, it is difficult to penetrate the skin again back through the exact same exit pin hole, and even if it does, it is even more difficult to follow the exact same path along the subdermal fibers. As a result, the thread that follows will inevitably grab some skin or some subdermal fibers along its in and out looping path, and when tightened, the stich will almost invariably create some dimpling of the skin at each entry/exit site. A double pointed needle can be driven through the tissues with the first sharp point forward like a conventional needle and have that first point come out through the skin. But unlike the conventional needle, to continue the complex course, the double pointed needle does not have to completely come out through the skin. If the second point is kept deep inside the tissue, that needle can now be handled by the outside shaft and driven back for another bite with the second point now forward piercing the tissues. One of non-obvious advantages enabled by the double pointed needle invention is that the attached thread never emerges through the skin and instead remains at the depth predetermined by the length of needle kept inside at each bite. This presumes a centrally located eye or thread connection site.

There are some prior art double pointed needles previously described by innovative plastic surgeons and are called shuttle needles. This simple design of a straight double pointed needle with a hole for the thread in the middle is known in the art. However, the present invention improves upon this type of needle with a number of non-obvious design modifications that provide many more functional advantages and which adapt it to be especially useful for the purposes described, infra. For example, some of these differences include: Size: prior art length of 10-15 cm vs. 25-50 cm for the invention & prior art diameter 0.8-1.2 mm vs. 1.5-3.5 mm diameter. Curvature: prior art straight or simple curved arc vs. a relatively straight central portion with a curvature at one if not both ends for the invention. In one embodiment the needle preferably takes a "J" shape, or in an another, a double "J" shape. Cutting point: prior art sharp point tip with round cross section vs. sharp point tip preferably with cutting sharp edges in cross section and a long bevel specially oriented according to its curvature to allow it to slice through as it is tunneled inside the dermis without risk of cutting the skin surface along its path. In addition to being able to be driven from a long distance (from infraclavicular to upper abdominal), the needle used for the RAFT needs to maintain the suture in an even tissue plane as it is threaded through what becomes the mammary folds is considered important by the inventor for desirable results. Otherwise, instead of resulting in an even line fold, the purse-string tightening may result in unsightly curtain like dimples, bulges and folds.

Malleability: prior art brittle hard vs. rigid but malleable enough so its path can be steered to a certain extent along its curved path from the outside, while it is handled from the distant exposed end as it is pushed through the tissues and manually steered externally along the arc and kept at the desired anatomical depth.

In addition to the above, the inventor conceives of a family of needles that may for convenience be categorized into the following types. All are preferably curved and pointed on one or both sides. These are considered by the inventor as the improvements and the novel features to be added to the simple double pointed needles previously described.

a—Eye or swaged thread insertion point closer to the needle point edges: The previously described shuttle needles have a simple hole for the thread (the eye) at the approximate mid-point of the needle. This mechanically weakens the needle at its very center where the torque is strongest while it is driven through the patient, making it prone to breaking with a broken piece deeply lodged and causing complications. To remedy that shortcoming in the prior art, the inventor has conceived of an alternate modification which places the eye close to one of the sharply pointed ends so as to reduce the torque capable of being applied as the needle may be grasped nearer the eye when inserted, and thereby also reduce the chance of the needle breaking at the eye. Most if not all previously described shuttle needles have the eye, or the attachment point of the thread, at the middle of the needle shaft. The inventor has made the discovery that an eye close to the pointed edge still serves the same purpose of being able to shuttle a stich while reducing the possible torque to be applied at the weak eye or the suture insertion point and therefore greatly diminishing the possibility of the dangerous complication of breaking the needle in its middle with one of the halves deep inside the patient's tissues.

b—Reinforcement of the needle at the eye or the swaged thread insertion site: The second modification, regardless of the location of the eye or suture insertion point, consists of reinforcing the area around that weak spot to further inhibit possible needle breakage. This reinforcement could preferably be in the form of a metal sleeve around the eye opening, a thickening of the needle shaft at that location, or a segment of stronger alloy used at that particular location or otherwise.

c—Swaged thread design: For a single use device, a present day requirement for all modern sutures, the swaged thread design is the preferred embodiment. The thread can be connected at one end for the single sharp end needle embodiment or on the shaft somewhere between the two points with the reinforcement described above for the double sharp end needle embodiment. The thread material can also be molded around and through the needle shaft for a more secure connection that does not weaken the structural mechanical properties the needle.

d—Adjustable or Marked Exit/Pivot Point: For the double pointed needle to maintain its suture thread deep inside the tissues and avoid skin dimpling, it is presently considered by the inventor to be critically important to always maintain one of the needle point tips under the skin. The opposite point should not exit the skin while the needle shaft is reloaded on the needle holder and the needle shifts direction to advance and take the next suture bite. This is delicate and trickier than it may seem, as inadvertent minimal exiting of the second needle tip will inevitably catch dermal fibers during re-entry, annul the advantage of the double pointed needle and lead to failure of that entire needle path. Furthermore, the depth at which the needle switches direction to be driven forward again determines the level at which the tissues are sutured. The problem becomes even more delicate when the desired depth/level of tissue suturing is more superficial or needs to be precisely set. Simple prior art double pointed needles do not offer a mechanism to prevent inadvertent exit and provide no means to gauge the depth of the needle tip as the needle is withdrawn leaving the surgeon guessing without any objective reference as to how much length of needle is still inside the patient.

To remedy that shortcoming in the prior art, the inventor has conceived of placing visible graduation marks, grooves or tiny rings on the needle shaft, preferably extending near each end, to accurately determine how much needle is still inside the patient, and at the same time, determine and set the depth of suturing.

d—Stops to prevent inadvertent needle exit: Another and perhaps even more useful additional innovation is to place a structure on the needle shaft at predetermined distances from the pointed tip, like a ring, a bulb, an arrowhead, or some barbs that will function as stops to prevent inadvertent exiting from the skin and which also function as pivot points to indicate a change in direction. These "stops" could be placed at fixed predetermined locations on the needle shaft, with different needles for different applications requiring different level of suturing. Alternatively, the stops could be slidable or otherwise adjustable such as by being mounted on ring sleeves so as to adapt the same needle for use with different surgical procedures. And, the stops could also be made to retract, fold in, withdraw, or otherwise become reduced in cross section when needed to thereby reduce the eventual exit opening or skin puncture diameter, making it less traumatic to withdraw the needle when it is time to do so. This "stop" innovation provides a more objective indication to the surgeon as he works and which helps him avoid unintended exiting, and thereby improves his chances for a successful surgery, to both the patient and the surgeon's benefit.

e—Needle construction comprising two or more parallel shafts joined at the tip that are sharpened and made into cutting tips: This innovative needle design comprises two or more parallel shafts joined at the tips that are rendered pointy & sharp cutting. The slit between the two shafts provides ample room for the thread to move freely and yet be retained and potentially wedged within the needle as it is used. Furthermore, the thread loop knuckled at a 90° angle to the plane of the needle shafts acts like a natural stop to prevent inadvertent needle exit and the apex meeting point of the shafts also serves as a good anchoring or retaining point for the thread. Of course, marked graduations to gauge depth and full mechanical stops as described above to prevent inadvertent exit are still useful options.

f—Needle with an opening eye, or a slit allowing it to grab a thread segment: In this construct, the eye of the needle can be opened to insert a thread loop, or has a passage that allows a thread segment of loop to enter the eye when the thread ends are not available. Contrary to needles with a standard eye opening that can only be fed the ends of suture threads through the eye, this novel type of needle does not need to have the end of a thread available to grab it. When the ends are buried or not available it can grab a thread segment or loop through its eye and continue to suture that thread. Such a needle makes it possible to pass a loop back through the grommet either to close a weave path or to emerge back through another grommet allowing for a more complex and supportive weave. A double pointed needle with the eye that opens is a very useful tool that can take a suture loop and weave it deep through the tissues to complete a complex stich path. Two possible designs for the opening eye needle invention are shown in FIG. 42. The embodiment shown in the upper figure has a passageway providing a way to hook the suture. The bottom figure depicts a deflectable or bendable arm that can be deflected to allow passage of a suture therethrough and into the eye, after which it closes to retain the suture.

g—Double pointed needles with two eyes. One that opens and the other standard or that already has a swaged on suture or one already with two threads, one close to each eye. In this even more useful embodiment the needle has two potential suture attachment sites, one close to each end. This can allow for inserting even more complex weaves through even more complex paths without necessarily having the thread ever grabbing dermal fibers.

h—Needle where the cutting edge has small sharp dissecting winglets that ensure an even level of travel as it courses through the subdermal/dermal tissue planes. One such example is depicted in FIG. 45.

i—Combinations/permutations that includes two or more of the above design innovations:

In the RAFT surgical procedure described herein it becomes necessary to provide an anchor with a tightening device in which a number of sutures are secured and used to adjustably lift and support the surgically repaired/augmented breast. This could take the form of a simple suspension hook introduced through a small slit and guided to curve around the superior aspect of the clavicle to hook it to the patient's clavicle. Alternatively, through a small incision on the anterior aspect of the clavicle a curved blunt needle can be introduced to curve around the posterior aspect of the clavicle and emerge in the supraclavicular fossa, then without completely coming out (Shuttle principle) follow the postero-superior surface of the clavicle and emerge through the anterior wound. The thread that follows would have left a loop around the clavicle upon which the long threads can be suspended, looping down to the upper abdomen and then locking the entire construct at a determined level of tightness. This is the clavicle loop alternative that requires a shorter double pointed shuttle needle with a tighter arc of curvature, as described in more detail in the Detailed Description.

In yet another alternative, the suspension can be done with the help of a standard bone anchor of the type that has barbs that open once the outer cortex is pierced to prevent pull out. Or a bone anchor of the type that is secured as a screw through the bone cortex may be successfully used. The anchor can be either introduced under direct vision after making a small incision and dissecting the tissues overlying the clavicle, or preferably through a minimal incision using a modified drill guide tissue dissector or a cannulated screw inserted over a previously driven guide wire. (Such techniques are standard and well known to skilled surgeons in the surgical art). The screw is preferably a self-tapping screw to avoid the tapping stage required to create the threads in the bone.

Traditional anchors have threads and needles attached to them so the sutured tissues such as ligaments and tendons are secured to the bone through the anchor. In this application tissues are not sutured directly to the bone, rather the anchor acts as a suspender for a loop that is being tightened into a purse string and brought cephalically. One simple way is to have a strong suture loop or a hanging washer loop connected to the anchor and then looping the long purse string suture through that loop as it is being tied. However, this may be found to be cumbersome and not ideal. Adjusting the tightness of the suspension and of the purse string by tying a knot is not precise and the secured knot leaves behind an undesirable mass of palpable bulky tissue. And, once secured, the process does not leave room for adjustment.

To that effect the inventor has conceived of various alternative designs for simpler, more practical, adjustable, elegant and less bulky results. One such concept is the use of washers around the bone screw and by having the thread loop around these washer rings it can be locked in place at the proper tension and level by tightening the screw. Furthermore there are many mechanisms by which threads can be securely locked together at the desired tightness with a device where the threads enter a passage or hole or loop and a screw or a cam mechanism tightens this passage to lock them securely in place. This tightening device can be an integral part of the anchor as a screw or a cam inside the already screwed in anchor, in which case a guide is required for the blind insertion of the tightening device or screwdriver and a thread guide passer loop is needed to pass the ends of the purse string suture through the deep anchor. In another embodiment, the tightening/locking device can be a separate structure connected or attached to the anchor but with more freedom of movement so that it can be exposed to pass the purse string loops, tighten them and lock them in place and then the tightening/locking device can then be buried deep inside the tissues once the suspension is complete. Two embodiments are shown in FIGS. 43 and 44.

There are a number of alternative means of locking the suture and suspending it to the anchor. The requirements are that is should not be bulky so it is not visible or palpable and ideally it should be adjustable. Thus, alternatives such as ultrasound or heat welding the sutures together or locking them with a tightening clip or belt-like band/washer system are also contemplated.

All of these alternatives are within the scope of this invention.

Another alternative is having the anchor already connected to the same long suture that is connected to the needle and leaving a mechanism whereby after driving its looped course around the breast the needle can pass through the anchor again or a ring on the anchor side of the thread to thereby complete its arcuate path. That ring could also have a crimping/screw/looping or cam locking mechanism that would allow locking the tightness of the loop and the suspension level.

The inventor has also conceived of a tissue mesher device which has been found to be extremely useful in several of the surgical procedures disclosed herein, especially in the RAFT breast augmentation/reconstruction. For the breast surgery procedures described infra, pulling up the abdominal tissue to the chest is limited by the resultant tightness of the advanced tissues. The inventor has discovered that meshing the abdominal tissue can relieve the tightness thereby allow much more tissue to be advanced and recruited into the breast while maintaining a tolerable low tension to the tissues and the suspension structure.

It is known in the art that making staggered small slits into a sheet of tissue allows it to expand. This principle is used by children to create ornaments and in metallurgy to create metal meshes. This is also how plastic surgeons, using a device called a mesher, stretch small pieces of harvested skin graft and expand them to cover much larger wound defects. However, with this invention, instead of meshing a skin graft, the surgeon meshes the tissues just under the skin that would otherwise restrict the advancement of the abdominal apron. The tissue mesher preferably consists of a number of sharp thin cylindrical rods with short sharp cutting tips at their penetrating ends. The rods are preferably firmly mounted in a staggered, orderly and predetermined pattern on a handling device that can control the depth and angle of penetration and the degree of oscillation. Oscillatory and translational sweeps of the mesher divide at different levels different anchoring fibers that hold the apron to the deeper abdominal wall. Due to the orientation of the rods, these alternating nicks do not open a tissue plane and prevent the formation of potential cavities which would be undesirable. Instead, as the individual fibers are cut by the rods at different levels they slide past one another to create a complex expanding inter-digitating scaffold. Thus without space generating slicing cuts these combined nicks allow the abdominal apron to freely translocate cephalically and advance into the breast.

This process also creates a healing interface so that once healing occurs, the apron scars down to its new location and tissue advancement is no longer dependent upon the sutures. Furthermore, this process creates tiny interstices with loose vascularized tissue fibers, an ideal environment with excellent graft to recipient interface where in aggregate, large volumes of micro tissue grafts can survive. Trauma, surgery, inflammation or radiation leads to tissue scarring, deficiency and stiffness that can cause disfiguring body deformities, organ dysfunction, motion restriction, pain or unstable non-healing wounds. The traditional treatment technique consists of surgically releasing the scar or the fibrous constriction by making cuts typically referred to as relaxing incisions. This maneuver provides the tissue mobility necessary to release the contracture, advance the freed up tissue to restore mobility or correct the contour defect or to reconstruct the tissue deficiency. To address a more extensive scar and tissue deficiency problem, the classic surgical solution is to incise or excise the scar, free up the incision/excision edges and stretch them open to create a wide gap, then fill the tissue deficiency void by transferring a block of healthy tissue with its own blood supply in the form of a flap. This is a major surgical intervention and one that leaves behind a new deficiency at the site where the flap was harvested. Unfortunately, this standard procedure of dividing the scar with relaxing incisions has many shortcomings:

First, the large gap created when the released tissue is advanced leaves behind a void or a cavity that needs to be filled in order to properly heal. This void is usually filled with a flap of tissue; a step that often requires another major surgical intervention whereby vascularized tissue taken from another location on the patient's body is transferred to fill that gap.

Second, the surgical incision itself to release the tissue leaves new permanent scars. The same is true for the site where the flap is excised. This amounts to treating a scar with a scar inducing procedure.

Third, this alternative does not address the stiff fibrous scar; it only incises it and divides it in half so that the bulk of the scar tissue remains in its present state.

Fourth, the degree of advancement that can be achieved with a single incision is limited.

Fifth, by also dividing the endogenous blood vessels, the incision impairs the circulation and limits the amount of advancement.

Attempts at excising the scar are also often futile. The scar can be conceptually compared to a solid fibrous block of tissue, like a brick wall separating and tightly tethering two normal tissue compartments that are more jelly-like in nature. Simply excising the block wall in itself induces tissue trauma that often heals by leaving behind a new scar and often re-erects a new wall and does nothing to address the scar tissue deficiency problem.

There is therefore a long felt need in the art for a better and less invasive alternative; a procedure that can truly address the fibrous scar, the tissue deficiency, the stiffness that limit organ function and joint motion and the body contour defects caused by tethering surrounding tissues.

Fat grafting has been touted as a source of regenerative tissue, and could, at the same time, address the scar and the tissue deficiency. Conceptually, a tight scar can be incised with a relaxing incision, its edges mobilized apart to release the tightness and then regenerative fat grafts inserted in the gap generated by the divided ends. A caveat is that for the injected fat graft to survive it has to gain blood supply from the recipient site. And as it is becoming well known in the art from the inventors experience and teaching that only droplets less than 2-3 mm or so across can develop new blood supply to survive as grafts, grafts collected in pocket gaps larger than 2-3 mm across routinely die from an inability to restore circulation and thus necrose leaving behind cysts and more scar. This is why as the edges of a standard relaxing incision need to open up by much more than 2 mm to achieve the needed relaxation, the larger tissue or flap inserted needs to be a block of tissue with its own blood supply in the form of a flap.

With the tissue mesher of the present invention, an inventive method for addressing this issue consists of releasing the scar or the restrictive tissue in a mesh pattern with the tissue mesher invention to loosen it and allow it to expand into a fibro vascular scaffold that can accept tiny tissue grafts. The resultant construct transforms a rigid tight scar into a much larger soft piece of healthy normal tissue. This method achieves a novel means of tissue engineering. Meshing the fibrous contracture (or the normal but taut endogenous fascia) with this method in effect generates a fibrovascular scaffold that is conducive to the survival of large volumes of micrografts.

An important conceptual advance over the prior art, realized with this invention, is the observation that the human body can heal needle sticks in the 2 mm diameter range (like intravenous lines or venipuncture sites) with no significant scar. Therefore, while the needle tip is innocuous in puncturing the skin, through an oscillatory or a to and fro translational movement of the tissue mesher, it can be made to inflict small nicks in the deeper tissues in different planes.

Another important conceptual advance over the prior art is the realization that a needle (or rod) cutting tip will be much more likely to cut a tissue placed under mechanical tension than mechanically looser tissue. To illustrate this, we can envision two violin strings wrapped around each other. If we forcefully tighten one of the strings and keep the other loose, a needle nick to this construct will cause the tight one to snap but will leave the loose one relatively unaffected. Thus, sharp pointed tips will preferentially cut the tight scar or the fibrous tissue that is pathologically tight or placed under tension by the forced advancement while sparing the looser tissues such as nerves and blood vessels.

These two conceptual advances put together allowed the inventor to develop the percutaneous tissue mesher invention and method as a means of bringing about the tissue advancement alternative to the flap that is usually required in the prior art for plastic reconstructions.

There is a natural limit to how much tissue can normally be advanced in order to close a wound defect, release a tight contracture or create a breast mound. This is due to the fibrous attachments between the skin and the deep immobile tissue layers such as the fascia underneath. These restrictive tissues can be collectively called the subcutaneous aponeurosis. Trying to advance the skin beyond the natural laxity limit of this subcutaneous aponeurosis places these structures under tension rendering them much more susceptible to being nicked by a needle tip and thus separated than the surrounding tissues. Thus, without causing visible skin scars, judicious percutaneous nicking of the subcutaneous aponeurosis can mesh expand the restrictive tissues/structures and facilitate the tissue advancement required for a reconstruction that would have otherwise required a distant flap transfer.

This "needling" of the deep tissues that does not leave a skin scar is useful in the release of Dupuytren contractures and other scar contractures. The needling meshes the tight tissues that cause the contracture and expansion of the meshed construct lengthens the contracture to regenerate the tissue needed to relieve it.

Yet another conceptual advance is the realization that the meshing pattern can be designed and gauged to create small interstices that can take advantage of the regenerative ability of tissues or become good recipient scaffold for fat grafts or other regenerative tissue grafts. The multitude of 2 mm or so gaps created by the meshing makes room for a multitude of tiny 2 mm or so graft droplets to survive. Fine meshing also takes advantage of the natural regenerative ability of live tissue. This is pertinent as tiny gaps in the body tend to spontaneously fill in and regenerate tissue if the space and the proper milieu are maintained. (This is how when we cover a wound with a meshed skin graft, the gaps eventually coalesce to from a new skin sheet that completely covers the wound). The small gaps might then fill up by themselves if kept open and prevented from collapsing again. Alternatively, these gaps can be filled with substances with regenerative potential such as platelets rich plasma, solutions containing growth factors, stem or other cells, or even just fat. The gaps can also be filled with allograft preparations which in themselves have regenerative potential.

One of the means to keep the tissue under stretch after filling the recipient area with fluid (tumescence) is to apply a relatively stiff splint, as previously described in a related patent application. This is also another means of keeping the meshed space open and to invite the natural regenerative abilities of the tissue to fill the thousands of microcavities, which in aggregate would represent substantial volume of tissue gained naturally by using the endogenous abilities of the body to regenerate across tiny gaps. Thus a judiciously performed meshing followed by appropriate splinting might allow the generated construct to fill in with healthy regenerated tissue instead of scar tissue that will have a tendency to subsequently contract and negate some of the benefit of the meshing.

It is also conceived that the meshing or expansion process does not necessarily need cuts induced by a sharp instrument. Forced tumescence by internal hydrostatic pressure can separate the native fibers to expand tissues in a similar fashion. Therefore it is contemplated that tumescence, as an adjunct or alone, can also be used to expand the tissue and generate an extracellular scaffold matrix with a multitude of tiny gaps. This matrix could then be induced to regenerate the tiny gaps on its own or with the help of added regenerative agents such as autografts, stem cells, allografts or otherwise.

The inventor has found that the length of the nicks and their spacing will determine the amount of expansion that can be achieved. Too aggressive a meshing will destroy the circulation, leading to ischemia and necrosis. It can also tear the deeper tissues and result in the creation of excessively large cavities instead of those of a delicate fibrovascular recipient scaffold. Excessive meshing destroys the integrity of the scaffold and leads to excessive numbers or sizes of cavities. Too many or too large cavities are to be avoided because tissue grafts lodged inside a cavity are far from the capillaries of the recipient tissue and will die from failure to re-vascularize. Therefore the inventor realizes that since the meshing ratio is limited, it is the amount of tissue that is meshed that determines the amount of tissue gain. In practical terms, from experience the inventor has found that a meshing ratio preferably up to about 20% achieves the desired results while more than about 30% will usually lead to undesirably wide gaps and cavities in which fat grafts will die. Using the 20-30% ratio, this means that to gain 2-3 cm of tissue, an area about 10 cm long will need to be meshed.

The mainstay of tissue engineering consists of seeding scaffolds with cells. The current practical limitation of tissue engineering is not the cells, as these are readily available from simple liposuction or from tissue cultures, but the three dimensional supporting scaffold with functional blood capillaries connected to the circulation of the recipient. This is why to the best of the inventor's knowledge currently available tissue engineered products are limited to a few cell thick alloplastic constructs that can survive by diffusion such as dermis or cornea. It is the inability in the prior art to build a fibrovascular scaffold (fibrous scaffold with capillary circulation) in the laboratory and connect it to the recipient blood circulation that limits the ability to build three dimensional solid organs or blocks of tissue.

This invention and method, however, is akin to tissue engineering. It creates in situ a fibro vascular scaffold out of a restrictive aponeurosis or a block of scar tissue and it seeds this vascular construct with healthy cell grafts. As the droplets of fat (or other regenerative seeded cells or reagents) engraft and mature in this new scaffold, the effective result is the generation of new fibro-fatty tissue. The inventor calls this novel procedure PALF for Percutaneous Aponeurotomy & Lipo-Filling. This is the inventor's novel and non-obvious regenerative alternative to the classic FLAP tissue transfer. In his investigations, the inventor has successfully performed a PALF procedure to patients that would have otherwise required a FLAP procedure to achieve the necessary plastic reconstruction and the results are successful.

The tissue mesher used in this procedure preferably consists of an array of needles that are fixed on a flat or slightly curved platform and that can penetrate the skin at various predetermined depths and may be oscillated or translated laterally to nick the deeper aponeurosis under tension. In various embodiments, the needles may be permanent sharp points or replaceable cartridges consisting of an array of sharp points, or commercially available hypodermic needles that can be loaded and tightened into the device at varying depths or with varying length needles or rods. The needles are preferably arranged on a supporting device in a staggered fashion and may preferably be organized either in one or more longitudinal rows or even more preferably in a singular, triangular, quadrangular, hexagonal, more rounded fashion depending upon the specific application and requirements. Three Al blocks, screwed together, with 3-19 holes, clamping hypodermic needles at varying depths ranging from ½ cm to 3 cm, alternating a cm apart, may be preferably used. If only a two dimensional PALF is desired, then all needles/rods can be the same level, but if three dimensional it would be preferred to do multiple levels. The hexagon pattern is preferred, but others work as well, depending on patient anatomy.

The edges of the device, or the entire plane upon which the device pins are mounted may also be rounded or partially spherical to facilitate the rocking or oscillatory motion needed to nick the underlying tissues.

The tissue mesher may also be either fixed and cause the deep tissue nick with a translational motion of the skin surface. Or it can be designed such that when placed against the skin, a hinge mechanism allows the needles to oscillate around one or more axes or a ball like joint or equivalent. The sharp cutting tips can either be constructed out of solid shafts with sharp pointed and cutting tips or alternatively hollow hypodermic needles. If hypodermic needles are used to deliver the graft in a controlled fashion, they may be connected to a pump/syringe system. The hypodermic embodiment connected to a pump/syringe system is considered by the inventor to be ideally suited to deliver the graft in a controlled, diffuse and evenly distributed fashion throughout the topography of the recipient.

Stops may be provided to indicate a penetration at predetermined depths. Or the tissue mesher may have an adjustable stop platform that determines the level of penetration.

One embodiment for the tissue mesher, labeled as a Rigottome™ mesher, is preferably a surgical instrument with a number of thin cylindrical rods that have short cutting tips at their apex. It may be introduced percutaneously (through the skin) to create a specific alternating pattern of multiple small cuts throughout the deep subcutaneous tissues, in accordance with the method described herein. Depending upon the specific technique used, the Rigottome™ mesher can generate a two or three-dimensional mesh of potential spaces inside a sheet or a block of tissue. When placed under tension the meshed tissue expands in one or two dimensions to open up these potential spaces into tiny cavities. Mesh expansion generates a beehive type of construct for the 3D mesh or a wire mesh construct of the 2D mesh. The tension could be an externally applied mechanical force or an internally induced tumescence such as can be achieved by injecting a fluid. That fluid may include normal physiologic solutions, regenerative reagents, or a suspension of cells or tissue grafts that can fill the tiny created cavities to successfully engraft. Other materials that can be added include processed allografts able to regenerate tissue after being inserted inside the matrix. Depending upon the technique, the process allows the 2D linear expansion of a sheet of tissue where the interstices can be filled with fluid or graft, or a 3D volumetric expansion of a block of tissue into a larger block with the multiple tiny generated cavities filled with larger amounts of fluid or graft. This process transforms a solid sheet (2D expansion) or a solid block of tissue (3D expansion) into a recipient scaffold consisting of a multitude of tiny cavities into which very large graft volumes can still maintain the critical 2 mm graft to recipient interface required for revascularization and survival. A solid block turned into a looser and larger framework with large numbers of staggered interstices where the injected graft can survive.

As a result of transforming a solid block or a sheet into a recipient structure, large volumes of fluid or graft can be infused inside that tissue with the expectation that the graft will survive. The method transforms a solid block into a loose graft recipient scaffold, or a restrictive cicatrix into a regenerative matrix. The tight fibrous cicatrix becomes larger, and by becoming filled with healthy fat graft, or by healthy new regenerated tissue, it becomes more like the surrounding tissue. Depending upon the density of the scar, one or more sessions can make the scar totally disappear.

The general application of this novel principle is not believed by the inventor to be limited to scar tissue. The inventor considerers that any block of tissue, whether an internal organ such as liver or kidney or whether muscle or fatty or normal can be meshed and expanded to create tiny gaps that the body can regenerate either naturally if the gaps are small enough and maintained open or with the help of instilled reagents such as the ones mentioned above.

To mobilize the abdominal panniculus and allow it to advance cephalically we not only need to expand as described above, but we also need to free it from its anchoring fibers to the deep attachments. Realizing that the apron has already been mobilized to a certain extent by the crisscrossing tunnels of the liposuction cannula, what still prevents advancement are the residual anchoring fibers that the normal cannula does not cut. What is necessary at this stage then is to divide these fibers and/or mesh advance the fascia that is anchoring their origin.

Yet another invention conceived of by the inventor is a tissue dissector. The meshing of the deep anchoring fascia is performed with the tissue mesher described above. But the inventor has discovered that while meshing provides some advancement it is sometimes not enough and more is needed. To that effect a device is needed that will snare and avulse and cut these vertical fibers which anchor and restrain the tissue from significant relative movement. The inventor has found that such a device designed to hook and avulse perforators and vertical fibers that prevent vertical swelling when tissues have been horizontally stretched but vertically restrained (such as what happens to tissues overlying long standing breast implants or tissue expanders) is needed. One embodiment for such a device is a thin long metal rod that could be solid or hollow, to simultaneously allow aspiration or injection. Its external surface is preferably rough like a rasp with sharp points or ridges or, if necessary, the inventor envisions that it could be more aggressive and have hook like or shark fin like winglet extensions for snaring the vertical perforator fibers. These winglets are preferably arranged radially around the shaft or in one side or plane of the shaft depending upon the specific dissection needed. The tip of the device is preferably round or flat round spatulated, but preferably not pointed or sharp so as to remain in the subcutaneous plane and not puncture the skin superficially nor the deeper muscle tissue and viscera. The device is preferably thin enough to be introduced through a needle puncture in a concealed corner of the tissue that needs to be dissected and elevated. Thickness preferably varies from 1.0 to 3.5 mm. The inventor contemplates that thinner rods will not have enough mechanical torsional strength to do most jobs and thicker ones will leave more noticeable scars at the entrance points. The device preferably has four portions: a short smooth round or spatulated tip that can tunnel through the tissues while maintaining the device in the selected plane; This part can vary in length from 0 to 1 cm. An active portion (the length with ridges or teeth or dissecting hooks/fins); this part can vary in length from 1 cm to 30 cm, depending upon the application. An inactive smooth proximal portion without roughening that will not damage the entrance site during the to and fro, oscillatory or other movements required to release the tissues; and an ergonomically fit handle portion, though a strong clamp gripping player could substitute for that portion. Depending upon the patient's anatomy and the task required, the active portion could be from about 2-3 cm to about 20-25 cm long.

A related invention conceived of by the inventor is a subcutaneous tissue rasp and dissector. There are a number of conditions where the tissues are lax and where tissue tightening is necessary and beneficial. This includes pathologic conditions where ligaments, tendons, fascia and many other deep structures stretch out or become attenuated. Tightening of the skin is also the mainstay of plastic surgery. Facial wrinkles are ironed out and the lax skin is tightened in the common facelift rejuvenation procedures. Tissue tightening is also required to lift back up what gravity has stretched out over the years. Examples include facial jowls, ptosis of the breasts and overhanging abdominal panniculus.

Tightening the tissues currently requires a surgical intervention to dissect the lax tissue, redrape or re-tighten it to the desired position and resect the excess lax tissue and/or suture plicate the laxity. It is also well known that post inflammatory healing deposits scar tissue that has an inherent tendency to contract. Therefore, to bypass the invasiveness of surgery, a number of devices in dermatology and plastic surgery have been designed to achieve and deliver a controlled deep dermal/subcutaneous tissue injury that leads to inflammation and subsequent healing with scarring and fibrosis that cause the desired retraction and tissue tightening. Most of the devices as known by the inventor deliver the active agent in the form of laser light, focused ultrasonic energy, radio-frequency energy, or thermal energy. They include many complex design features to ensure that the superficial tissues are protected while it is only the deeper ones that will absorb the energy and will be affected. (What is sought to be avoided is the delivery of the injurious energy to the epidermis and most superficial dermal layers which will cause blistering and subsequent visible unsightly scars). These devices were mostly designed to treat the wrinkles of the aging face. Unfortunately, these devices have limited effectiveness; proof is that despite years on the market, they have not replaced the surgical facelift operation.

The effectiveness of these devices is limited by their inability to safely deliver the amount of injury to the deep dermis and subcutaneous tissue that will result in the required scar retraction while completely sparing the more superficial delicate tissues from the injurious agent. Since the distance between these two tissue layers is of the order of millimeters and fractions of millimeters, even a limited scatter of the most precisely focused agent is bound to cause collateral damage. This is particularly obvious since the injurious agent is delivered from the outside surface and therefore has to travel through the delicate superficial structures without injuring them before reaching the layer that need to be treated.

As an alternative to these prior art devices, the inventor has developed a subcutaneous tissue file or rasp that can directly mechanically abrade deep tissues and in a precise and controlled fashion to cause scarring to the abraded tissues without affecting the more superficial tissues above as well as the more delicate external surface of the skin. This invention allows the surgeon to manually deliver in a controlled fashion a mechanical abrasive injury exactly where it is needed to the inner internal surface of the skin, causing it to scar down and contract as desired to achieve the tightening and lifting of the treated tissues. To be most effective, this abrasive injury is delivered to tissues that have already been loosened and partially separated and mobilized from their anchoring deeper structures, a step that can be achieved by the tissue dissector described herein. The inventor realizes that the structures to be tightened need to be first dissected and mobilized free with the tissue dissector and then allowed to redrape and made to contract with the tissue abrader. The percutaneous tissue dissector and the percutaneous tissue abrader are related devices consisting of a thin long relatively stiff rod of medical grade material which differ by the design and aggressiveness of the teeth or ridges built along their functional part in a continuum going from the least abrasive tissue file with ridges, to the tissue rasp with needle like teeth to the most aggressive tissue dissector with barbs or fins that act as a saw. An important feature of these devices is their overall external diameter that is thin enough so that they can be introduced through needle punctures in the 2-3 mm range. Puncture sites that require no sutures to close and essentially leave no scar. Thus while the central rod is limited in OD, the barbs or fins could be retractable with a mechanism that pushes them out once the file is introduced through the narrower puncture site.

Furthermore, to be most effective in and to obtain the best retraction, the abraded tissue should be redraped over the deeper structures and kept loose under no tension till the healing process that takes a few weeks causes it to retract and scar down in the new position. This can be achieved in two means or a combination of these two.

1—Applying an external adhesive supporting structure such as a thin adhesive supportive bra in the case of the breast or an adhesive supportive, repositioning mask in the case of the face. This post procedure bra or holding and molding device preferably can stay in place for the required few weeks, or is easily replaceable till the tissues scar down.

2—Inserting supportive sutures that stay deep and serve to reshape, plicate, contract or suspend the deep tissues. These sutures are best inserted with the double ended needles and the grommets described herein and as needed suspended with the anchor and tightening devices also described above.

In a preferred embodiment, the device preferably consists of a thin solid metal probe (or a hollow cannula that can also deliver fluids or tissue and cell suspensions if needed) that can be inserted through a few puncture sites or tiny hidden incisions and then be tunneled under the skin to where the tightening or dissection is desired. The rod preferably has a blunt, round hemispheric tip to prevent it from inadvertently puncturing tissue planes or a round spatulated tip to dissect the tissue planes without puncturing through them. Some of the fins or barbs can be designed such that they are retractable by a screw or an internal push mechanism. The mechanical abrasion can be manually performed, or alternatively the filing motion can be delivered by an external mechanical source that either pistons back and forth, in and out, and/or rotate or oscillate. This internal skin file device is completely different from other prior art file and rasp devices in that it is a thin rod of medical grade material that has relatively sharp fine ridges along its active portion and may have an inactive portion, if desired.

It is also understood that to perform such a dissection, the tissues often need to be primed with a tumescent infusion that can help open up the tissue planes, put the restrictive fibers under tension and thus more prone to avulsion, and cause vasoconstriction that will prevent bleeding from the avulsed vessels. External traction could also provide an alternative/supplement to the tumescent infusion.

Yet another related invention addresses the problem of breast ptosis. Breast ptosis, is the drooping of the breast from acquired laxity of the supporting ligaments and the skin envelope of the breast. It is the most common deformity of the female breast and virtually all women will develop some breast ptosis with age. It is estimated that over 100,000 surgeries alone are performed in the USA to correct this deformity. Ptosis is classified according to the relationship between the nipple and the inframammary fold. In the non-ptotic breast the nipple is above the level of the fold. In grade one ptosis, the nipple is at the level of the fold; grade two, the nipple is below the fold; and grade three, the nipple is the lowermost structure of the breast.

While minor degrees of ptosis, can be corrected by filling up the stretched out skin envelope with an implant, larger degrees of ptosis require re-tailoring of the skin envelope to bring the nipple back to above the level of the inframammary fold and to restore the hammock-like supporting effect of the lower pole breast skin. This tailoring operation requires multiple incisions to remove (or plicate) the excess skin and therefore leaves behind unsightly scars. These incisions and scars are believed to be the reason why the overwhelming majority of these deformities are never sought to be corrected. Therefore a device and method that could be used to surgically correct breast ptosis without incisions or scars would be a very useful.

Women with ptotic breasts typically wear a support brassiere for most of their waking hours for at least cosmetic reasons. Some stick-on brassieres have recently been developed where, as the adhesive tape plicates and folds in the excess skin, a normal breast contour is restored.

The main problem in breast ptosis is the excess skin and laxity of the internal suspensory ligament (also called ligament of Cooper). Excess skin in the vertical dimension along with vertical elongation of Cooper's ligament causes a loss of the suspensory effect and brings the nipple down. Excess skin in the transverse dimension along with laxity of Cooper's ligament causes a loss of the hammock-like support of the breast permitting it to fall further. Therefore the skin and the ligaments need to be tightened in two dimensions in order to restore both the suspension and the hammock. To remedy this issue, the inventor has conceived of a kit and a method of surgically inserting a permanent, preferably woven, brassiere under the breast dermis to restore the supporting ligaments, to reconstruct a hammock, and to induce the skin to shrink.

The kit device preferably includes:

1—A bone anchor, in order to secure the breast to a solid fixed anatomical structure. That anchor is preferably inserted in the sternum, the ribs or the clavicle. The threads weaved into the breast as explained below connect to this anchor.

2—Threads, that are surgically tunneled subcutaneously and weaved inside the breast to restore the ligaments and the hammock. These threads could be made of suture materials commonly used in surgery or preferably out of synthetic, allogenic or alloplastic materials that favor their ultimate transformation into fibrous ligament. Preferably, the threads are also color coded such that each thread has a different color to facilitate the recognition of the ends of each thread as they are tightened during the surgery. The inventor has found that a typical procedure would preferably be expected to require 6-12 threads of different length.

3—Special needles, to drive these threads. The needle is preferably curved, double pointed with graduation marks near the pointed tip that indicate the level of penetration, and with the thread swaged in the middle or close to one of the sharp points. Another type of needle that may instead be used is one where the eye can be opened to allow the insertion of a loop. Yet another needle is one that includes a stop to prevent inadvertent exit as it is shuttled through the tissues. These needles may be the same needles as described above.

4—A brassiere, that can be applied sterile on the operative field as a surgical aid. This brassiere is considered by the inventor as an important element of this invention. After restoring the normal anatomical relationships of the breast architecture like a well-fitting brassiere would, the brassiere desirably becomes adhesive and sticks to the skin and becomes relatively plastic or rubber-like hard. The brassiere is preferably transparent or translucent in order to allow monitoring of the status of the underlying skin and to insure that the brassiere is still adherent. The brassiere also preferably has marked on its surface the preferred pattern of weave that the threads should follow, to thereby guide the surgeon during the operation. The external temporary brassiere provides static support for the breast while the weave is surgically formed so that the individual threads are passively weaved and their loops locked at the appropriate length without being under tension in the process.

5—An important attribute of this brassiere is its ability to hold the breast in the desired shape and suspend it in the desired position. It is also preferably rigid and well adherent to the skin such that snugly pulling the threads that constitute the weave locks them all at the ideal length and tightness for an even contour. If the brassiere is not adherent or not stiff, some threads might be tightened more than others to cause unsightly dimples. In essence therefore it is this brassiere that primarily determines the length and tension on the individual threads of the construct to make it even.

6—Preferably needle sleeve grommets, that fit around the needle as it emerges out of the skin and become the guide for the needle when it is reinserted again into the skin. These grommets keep the threads and the weave in the deep tissue planes as the needles come in and out of the skin, preventing the suture loop from catching dermal fibers as they perform the weave. This needle sleeve grommet is also considered by the inventor as an important and innovative part of the invention. Without these grommets, a shuttle needle (a double pointed needle with the eye in the middle) has been found by the inventor to only perform a simple circum-mammary loop. With the grommet keeping the skin/subcutaneous tunnel open, a loop of thread can stay outside and then interlocked with another loop coming out of the same tunnel so that the interlocking weave pattern can be performed and brought back down inside the deeper planes where it does not result in visible skin dimples.

7—Preferably a crimpling/locking device, that adjusts the length of each of the individual supporting threads as a function of its path along the stretched out skin envelope. This crimpling or locking device eliminates the need for the standard tying of knots. This prevents leaving behind a suture knot bulk and makes it easy to appropriately adjust the length and tension of the threads. The final exact adjusted length of each individual thread weaved through the breast has been found by the inventor to be important to the success of this procedure. The multiple threads preferably function together to distribute the support evenly among themselves in order to prevent dimples and contour irregularities.

8—Optionally, special dissector cannulas and liposuction and lipografting cannulas, if desired.

With this kit device and the method of application described herein, an internal brassiere can be surgically constructed subcutaneously to support the breast and lift it up to restore its normal aesthetics. Most importantly, the procedure leaves minimal scars as there are essentially no incisions and no sutures marks, only needle size puncture holes which heal leaving virtually no scarring.

An alternative to this inserted weave pattern is an external supportive shaping brassiere that firmly adheres to the skin after the dissection with the rasp is performed and can be worn for the long period of time necessary for the tissues to heal in the new location and for the dissected skin to retract to the new envelope shape imposed by the brassiere.

The inventor also has conceived a similar device and method to re-drape the stretched skin and jowls of the aging face. Double needles such as the ones described above can be used to insert a pattern of deep suture that can tighten or suspend the tissues. A supportive mask or bonnet is also included that can supplant/replace the sutures once the percutaneous dissection of the skin and its stimulation to retract are induced with the rasp and the file.

While many of the advantages and features are briefly described above, a more thorough understanding of the invention(s) may be gained by referring to the drawings and the Detailed Description of the Preferred Embodiments which follow.

BRIEF DESCRIPTION OF THE DRAWINGS

FIG. 18 is a side view of two alternative stops for use with a "J" shaped needle;

FIG. 20(a) is a partial view of the working ends of various tissue dissector and rasp alternate embodiments;

DETAILED DESCRIPTION OF THE PREFERRED EMBODIMENTS

Figure 1:
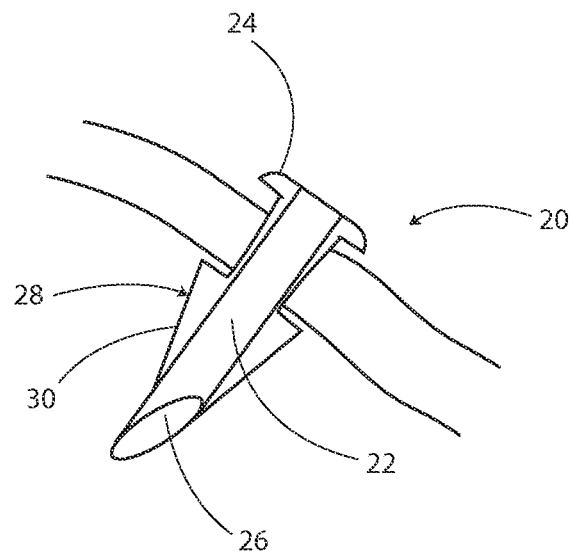
FIG. 1 is a side view of a grommet invention, inserted through a patient's skin, and detailing a flange and retainer.
Figure 2:
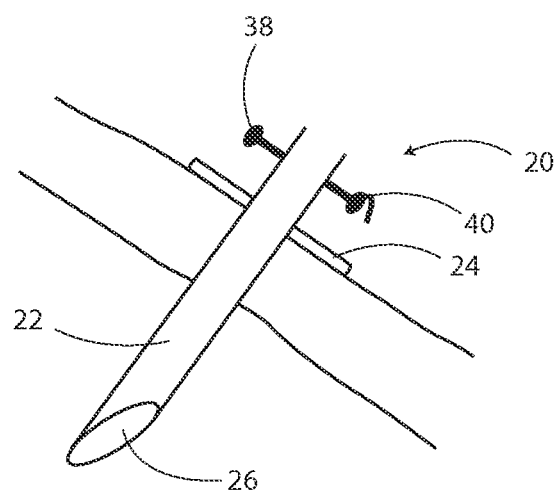
FIG. 2 is a side view of a grommet invention, inserted through a patient's skin, and detailing thread tie off structures.
Figure 3:
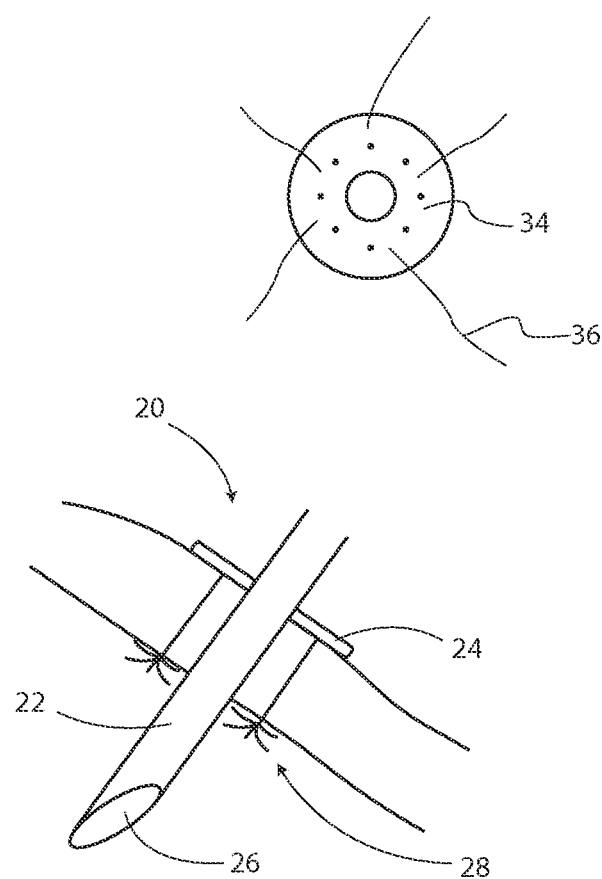
FIG. 3 is a side view of a grommet invention, inserted through a patient's skin, and detailing a flange with securing structure.
Figure 4:
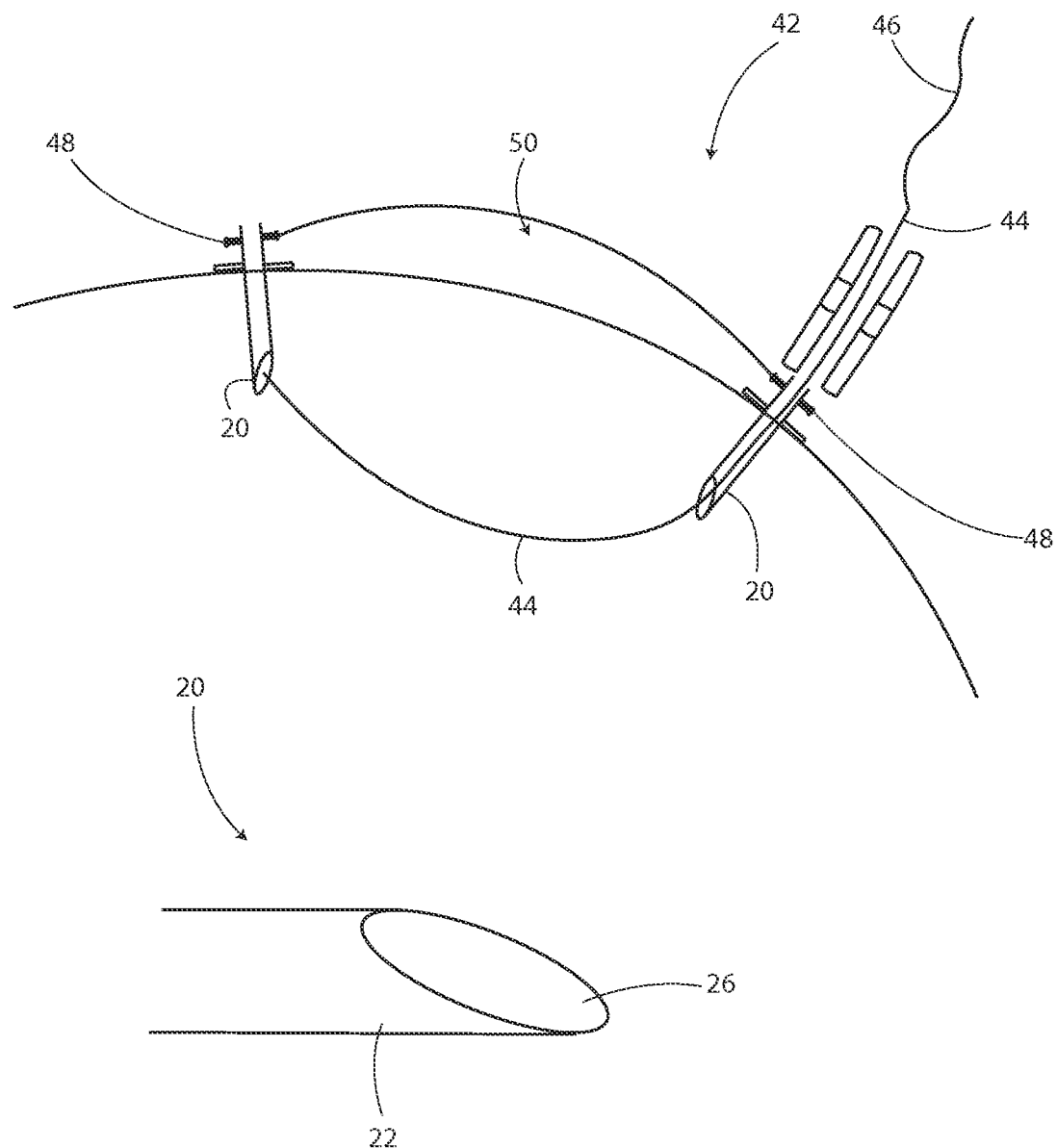
FIG. 4 is a perspective view of a jig extending between two adjacent grommets to guide a needle from one grommet to the other.

As shown in FIG. 1-3, a grommet 20 includes a central, cylindrical shaft 22 preferably with a top hat, annular flange 24 for engaging the skin surface as it is inserted into an incision in the patient's skin. The cylindrical shaft 22 preferably has a beveled tip 26 to aid in its insertion and which provides directionality for locating and threading therethrough a needle and thread, as is explained in greater detail below. Various embodiments of a stop 28 are depicted, as follows. As shown in FIG. 1, a collapsible pair of wings 30 may extend from the sidewall of the shaft 22, and which open to block unintended removal or exiting of the grommet 20 during use but which may be collapsed to facilitate its removal, when desired. Two other embodiments of a stop 28 are depicted in FIG. 4 and include a collapsible umbrella 32 extending from the flange 24. Or, as yet another alternative, the flange 24 may be provided with a series of holes 34 through which a suture, pin or other structure 36 may be inserted either parallel or oblique to the shaft 22 to secure the grommet in place. As depicted in FIG. 2, a threaded loop or suture securing or retaining structure comprising a cleat 38 around which the thread (not shown) may be wrapped much like a marine grade cleat. Alternatively, a spiral hook 40 may be provided through which the thread (not shown) may passed and wrapped around to the same effect. Thus, with the grommet 20, a designated opening, or incision, is reliably located and which is "clear" of surrounding tissues which might otherwise be undesirably caught or snagged as the needle and thread is passed therethrough.

As shown in FIG. 4, a grommet jig 42 may be secured to two adjacent grommets 20 to guide a needle 44 and attached thread 46 from one grommet 20 to the next grommet 20 during the RAFT procedure as described herein, or for any other surgical procedure requiring a suture to be implanted between adjacent grommets 20 or incisions. The grommet jig 42 generally comprises an articulating or swivel mounted fixture 48 at each grommet location and a fixed bar 50 extending therebetween. There are various structures and construction details indicated and shown in FIG. 4, the details of which would be apparent to those of skill in the art.

As shown in FIG. 5-18, a number of embodiments with alternative novel and unique features of surgical needles are depicted for use not only in the RAFT and PALF procedures but also for general surgical use. These are typically made of surgical stainless steel for reliable sterilization and as would be known in the art. Several of them have cutting edges and points in various configurations although others, as known in the art could be used as well. At least one needle is specially configured for the RAFT procedure and its specific use will be explained.

Figure 5:
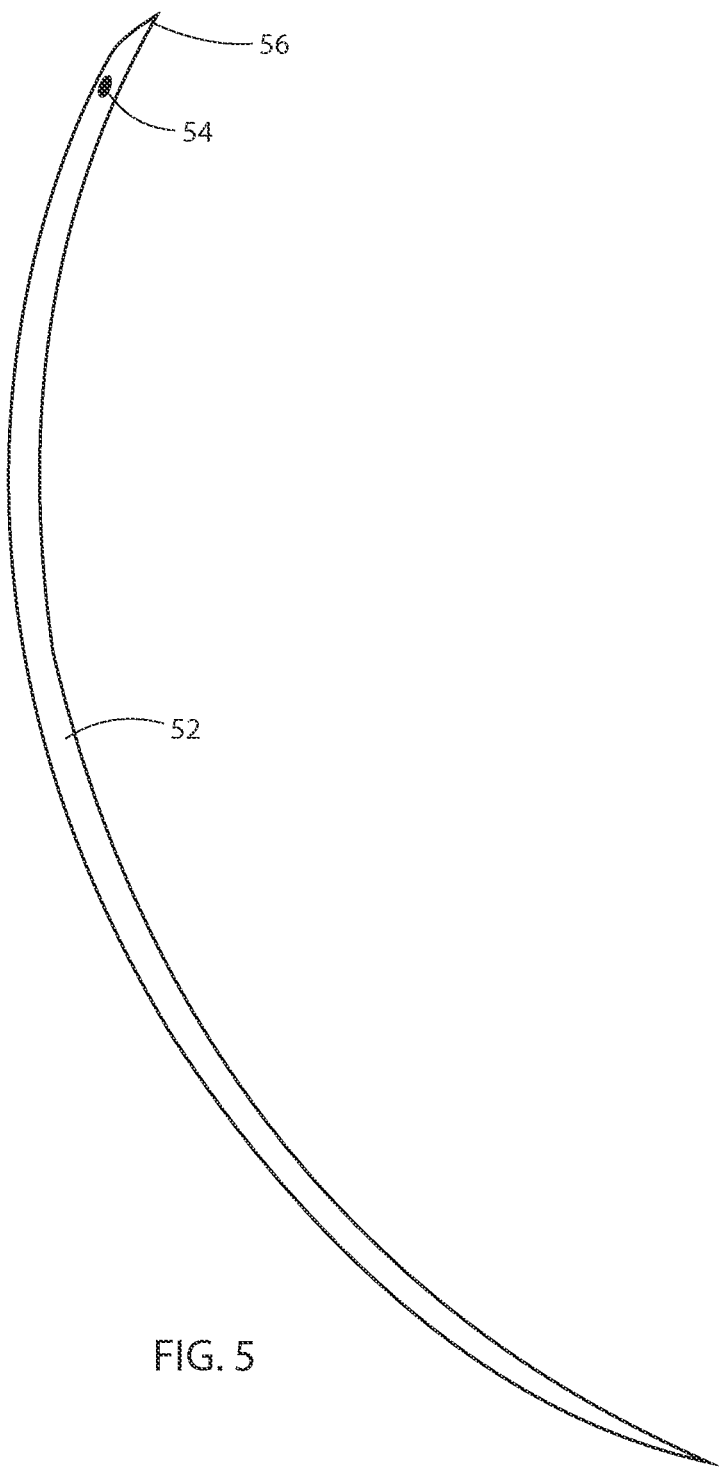
FIG. 5 is a side view of a double pointed needle of the present invention, with an eyelet at one end thereof.
Figure 6:
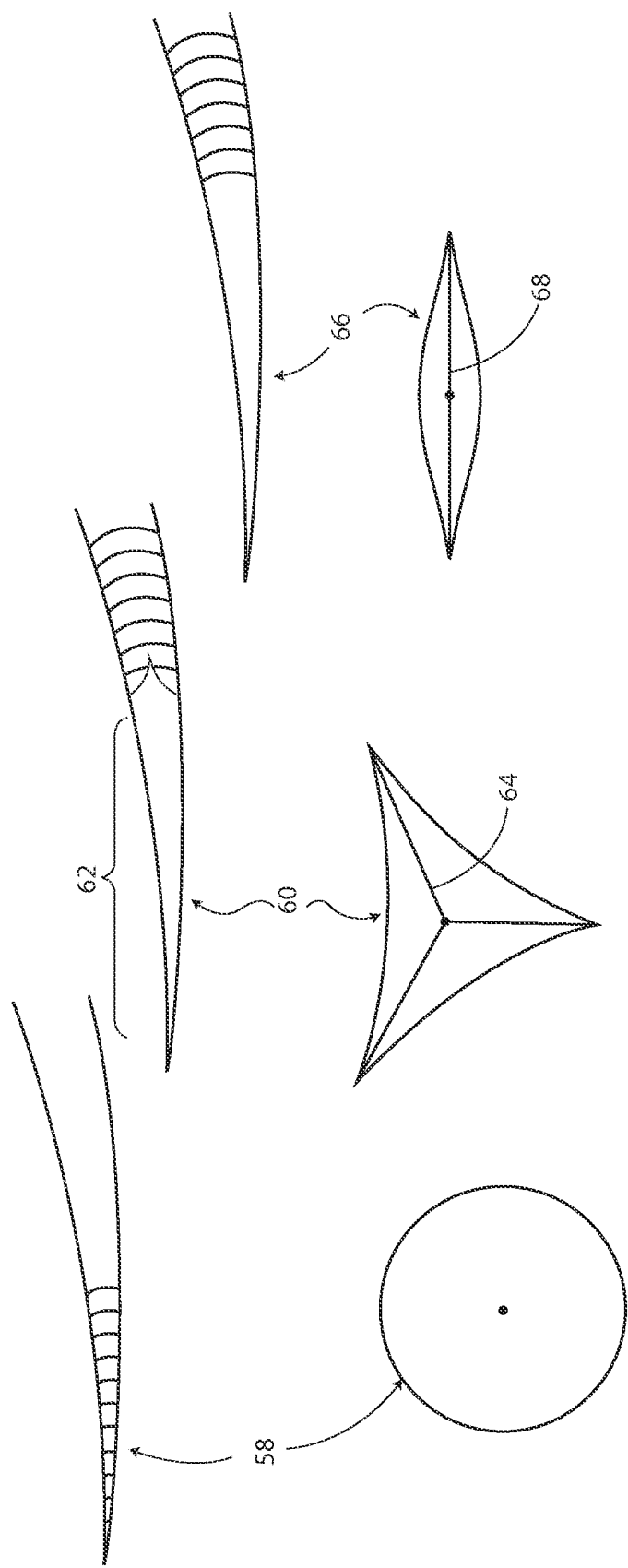
FIG. 6 is a partial view of several variations of the needle invention, with cross sectional views detailing their different embodiments.
Figure 7:
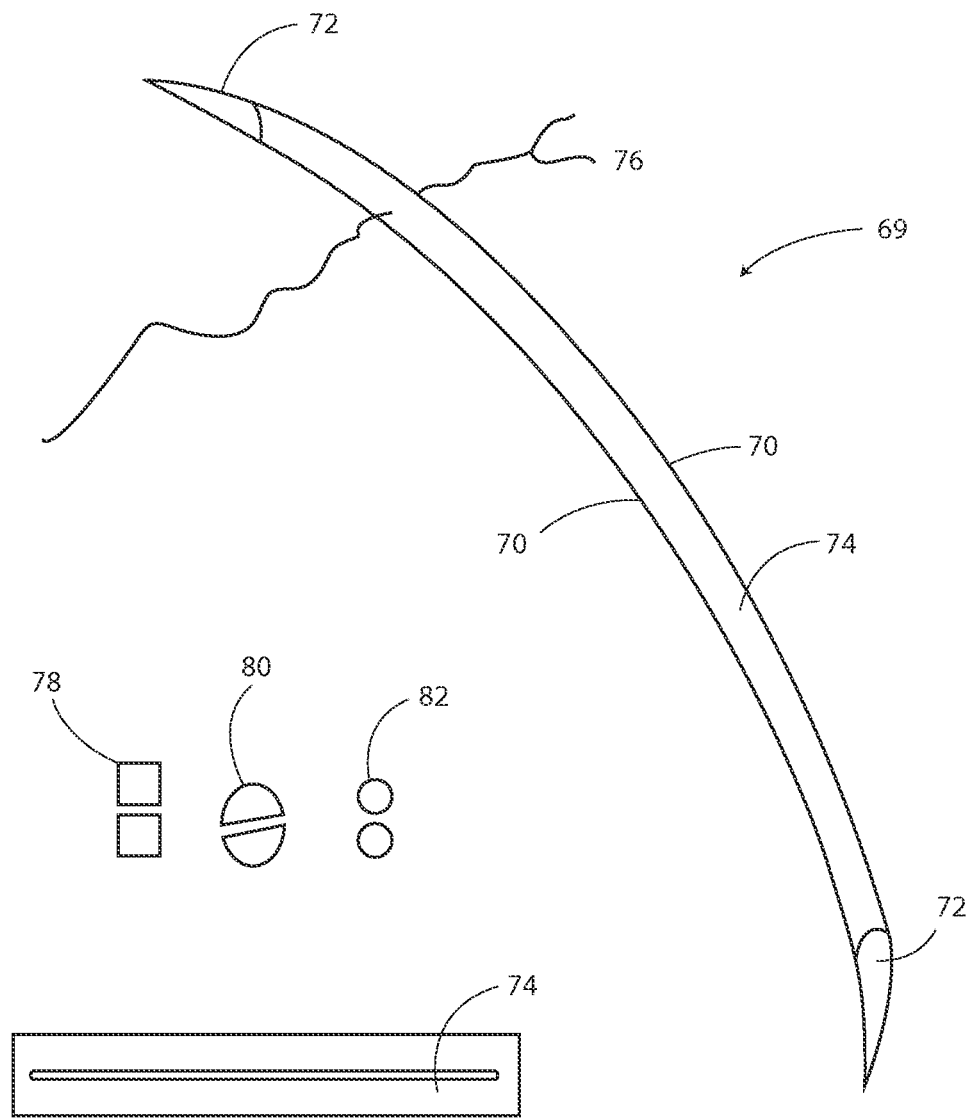
FIG. 7 is a perspective view of a double shaft needle embodiment with double pointed ends, with cross sectional views detailing different possible shaft shapes possible for use.
Figure 8:
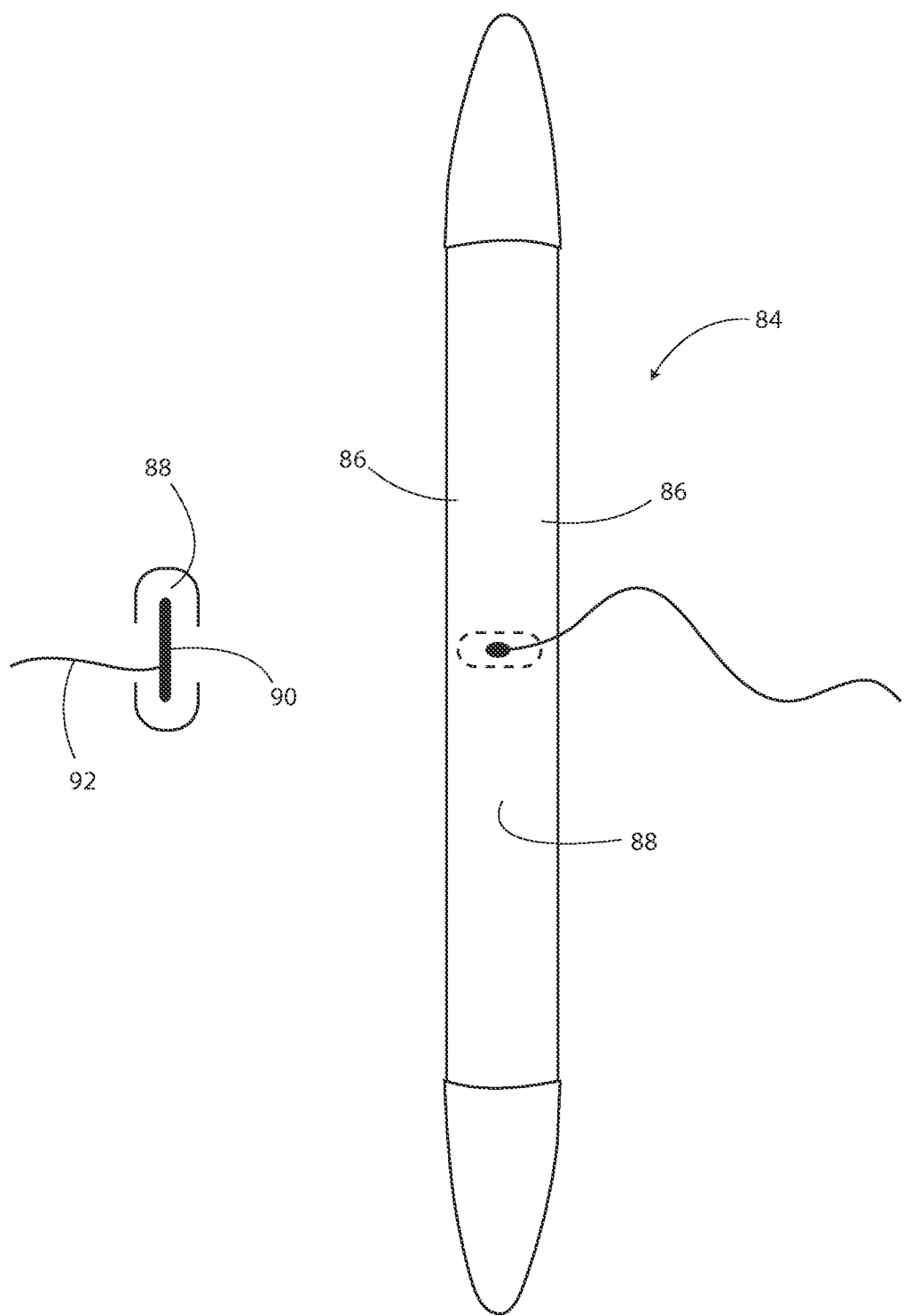
FIG. 8 is a top view of a double shaft needle with a central thread shuttle.
Figure 9:
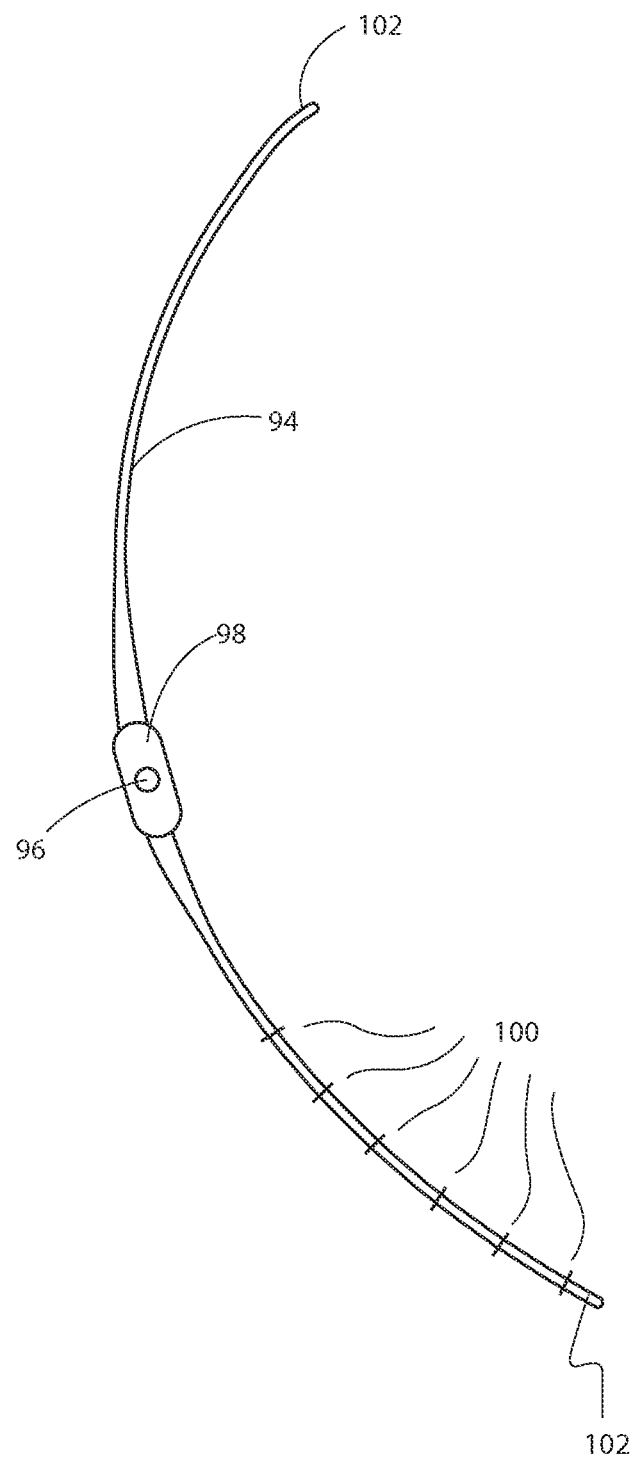
FIG. 9 is a side view of a double pointed needle with central reinforcement and graduations marked on an end.
Figure 10:
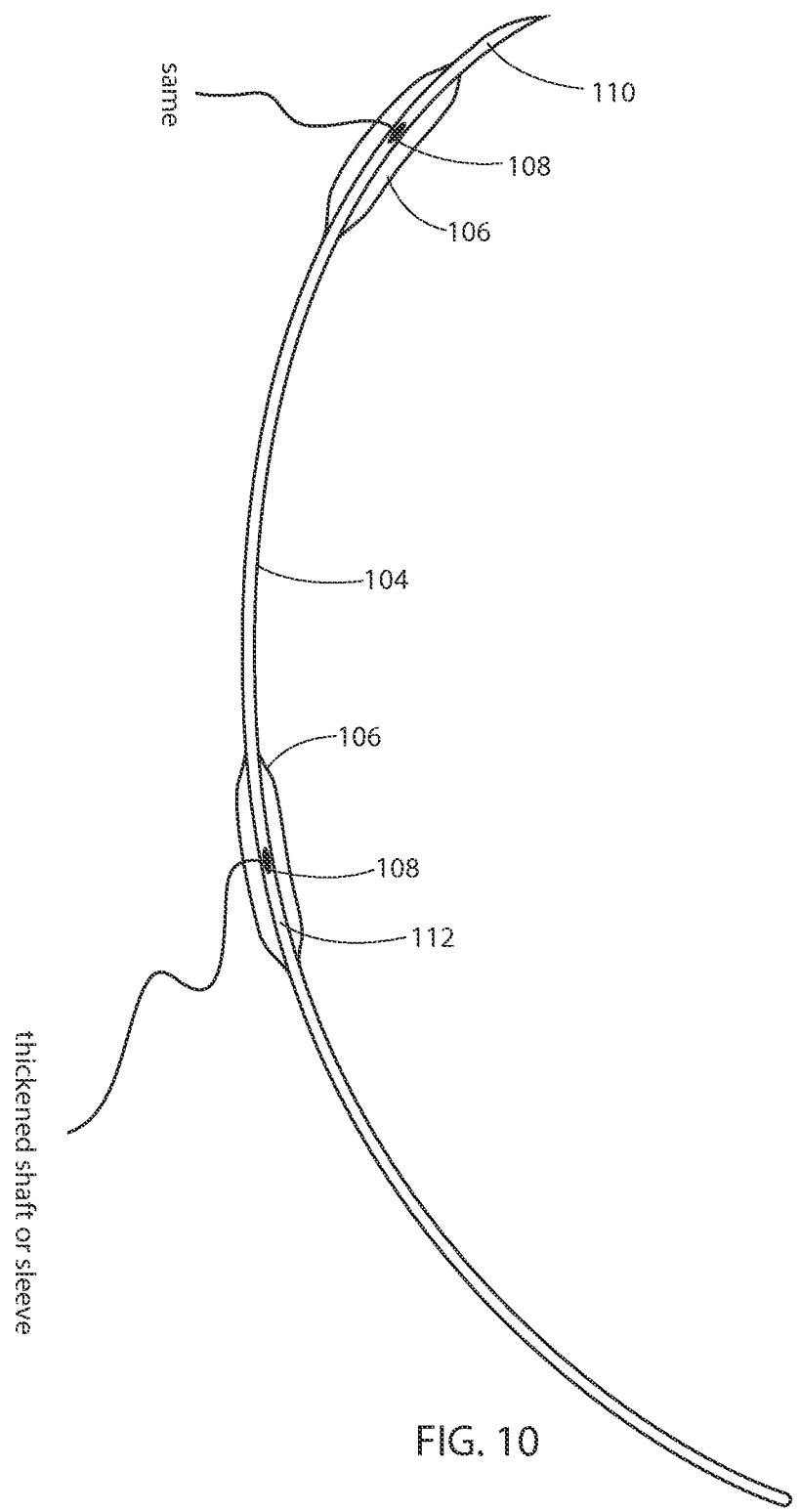
FIG. 10 is a side view of a double pointed needle with reinforcement depicted at an eyelet, whether positioned in the middle or at an end of the needle.

Referring now to FIG. 5, a generally curvilinear, double pointed needle 52 has an eye or eyelet 54 located near an end 56 through which thread may be passed when used, or which may have thread swaged thereat for a single use needle 52. FIG. 6 depicts various alternative cutting points which may be used as desired or as indicated for a particular procedure. As shown, a round point 58 has a circular cross section and which is especially suited for creating a smooth entry hole. A cutting point 60 with a long bevel 62 provides a trilateral cutting edge 64 for opening up a wider incision. A knife or blade tip 66 provides a bilateral cutting edge 68 which will cut through the tissues more evenly and assists the surgeon in dissecting the tissue planes, and maintaining the relative position of the needle with respect to the tissue planes. Staying level and staying in the same plane is helpful in avoiding the gathering of tissues, similar to drawing a curtain together, while preforming the "purse string" RAFT procedure as described herein. FIG. 7 depicts a particular construction of a curved needle 69 as has been used by the inventor. As shown, a pair of shafts 70 are joined at their ends 72, such as by swaging them together, leaving a longitudinal gap 74 therebetween and through which a thread 76 may be inserted. The ends 72 are sharpened into points as shown. The shafts 70 may have different cross sections, such as being a simple rectangle 78, semi-circle 80, or circle 82 and be suitably used for this construction along with many other shapes. With this construction, the thread 76 may be left free to slide along the length of the needle 69 as it is used, or it may be swaged or otherwise attached anywhere along its length, as desired. FIG. 8 depicts a straight, double pointed needle 84 formed from a joined pair of shafts 86, as before. However, additionally, a centrally located passageway 88 is formed between the shafts 86 and a shuttle 90 with an attached thread 92 is positioned within the passageway 88 so that it may freely slide from end of the needle 84 to the other as it is used. Alternately, the shuttle 90 and passageway may be provided and be crimped into place by the surgeon to suit his individual preference depending on his technique, the surgical procedure, or the particular patient. This same construction could also be incorporated into other needle designs. FIGS. 9 & 10 depict alternative structures for reinforcing that part of the needle through which the eye is located, to avoid inadvertent breakage of the needle as it is being used. In FIG. 9, the needle 94 is a double pointed, curvilinear needle with a centrally located eyelet 96. The reinforcement is provided by providing a swaged sleeve 98 of material near the mid-point where the eyelet 96 is drilled or otherwise formed into the needle 94. Also, as shown in FIG. 9, a series of measured graduations 100 are provided at each end 102 which indicate to the surgeon the position of the needle 94 as it is partially inserted in the patient so that inadvertent exiting of the needle 94 is avoided, and for more precise placement of the suture during the procedure. In FIG. 10, a curved, double pointed needle 104 has a thickened shaft 106, which could also be a sleeve swaged into place, surrounding the eyelet 108 as positioned either at an end 110 or at a mid-point 112.

Figure 11:
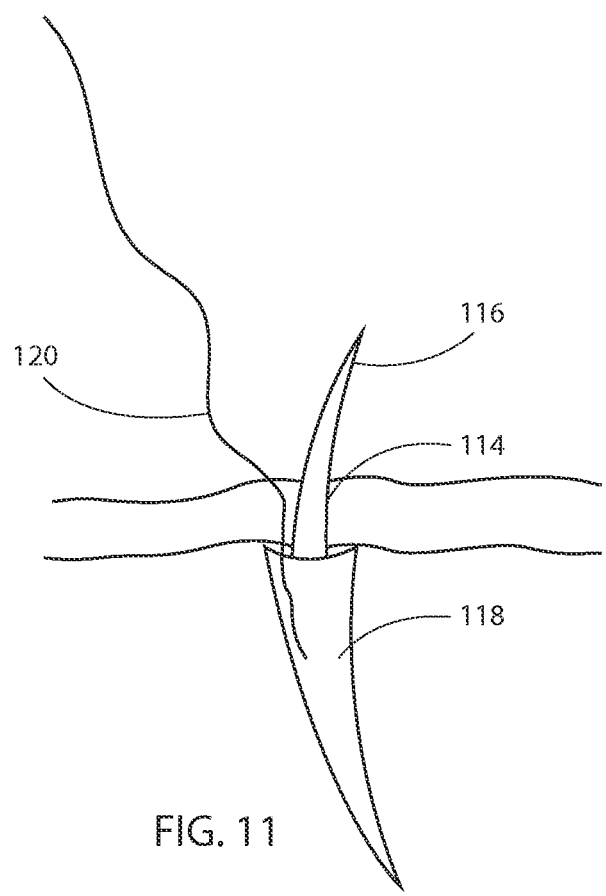
FIG. 11 is a partial view of a needle end inserted through the skin with a stop to prevent inadvertent exiting of the needle during the surgical procedure.
Figure 12:
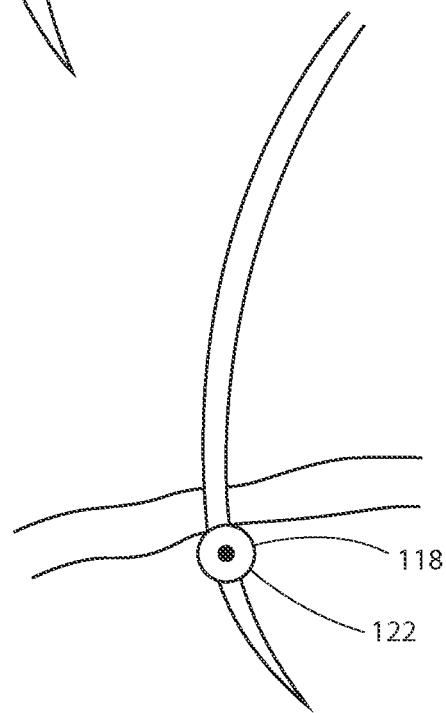
FIG. 12 is a partial view of a needle end inserted through the skin with a different design stop.
Figure 13:
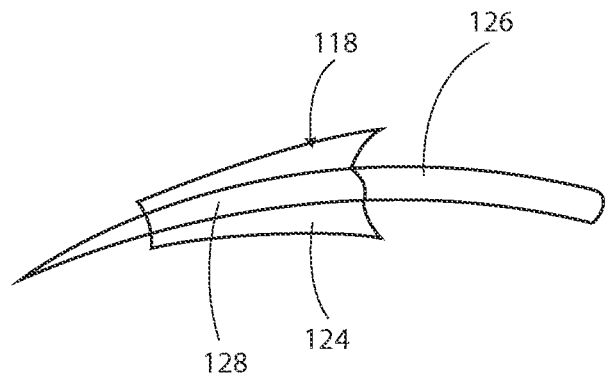
FIG. 13 is a perspective view of a needle end with a retainer threaded onto the needle to provide an adjustable retainer.
Figure 14:
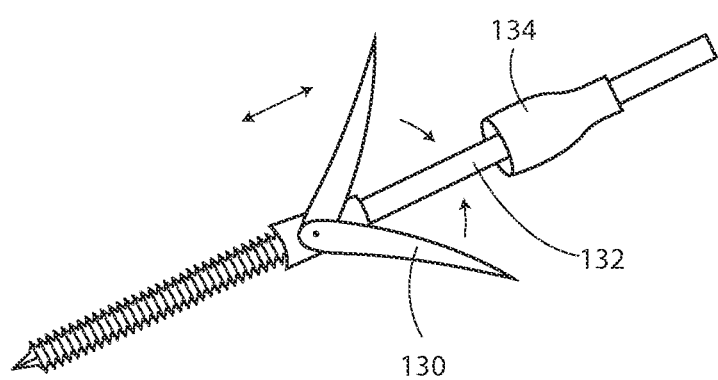
FIG. 14 is a partial perspective view of a needle end with a threaded retainer comprising retractable umbrellas.
Figure 15:
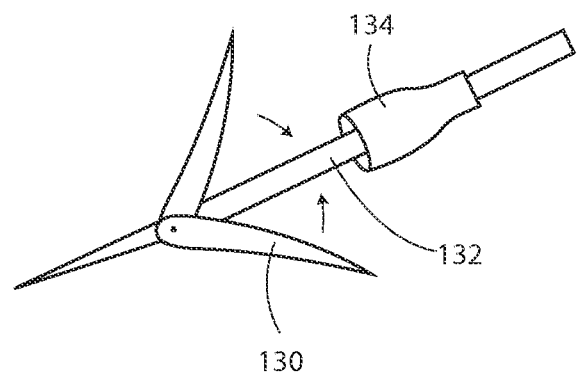
FIG. 15 is a partial perspective view of a needle end with a slidable retainer comprising retractable umbrellas.
Figure 16:
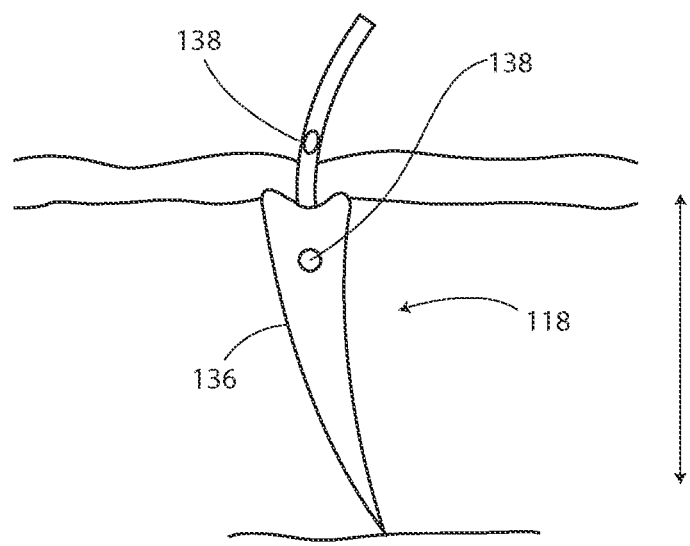
FIG. 16 is a partial perspective view of a needle end with an arrowhead stop and depicting alternate eyelets for the thread.
Figure 17:
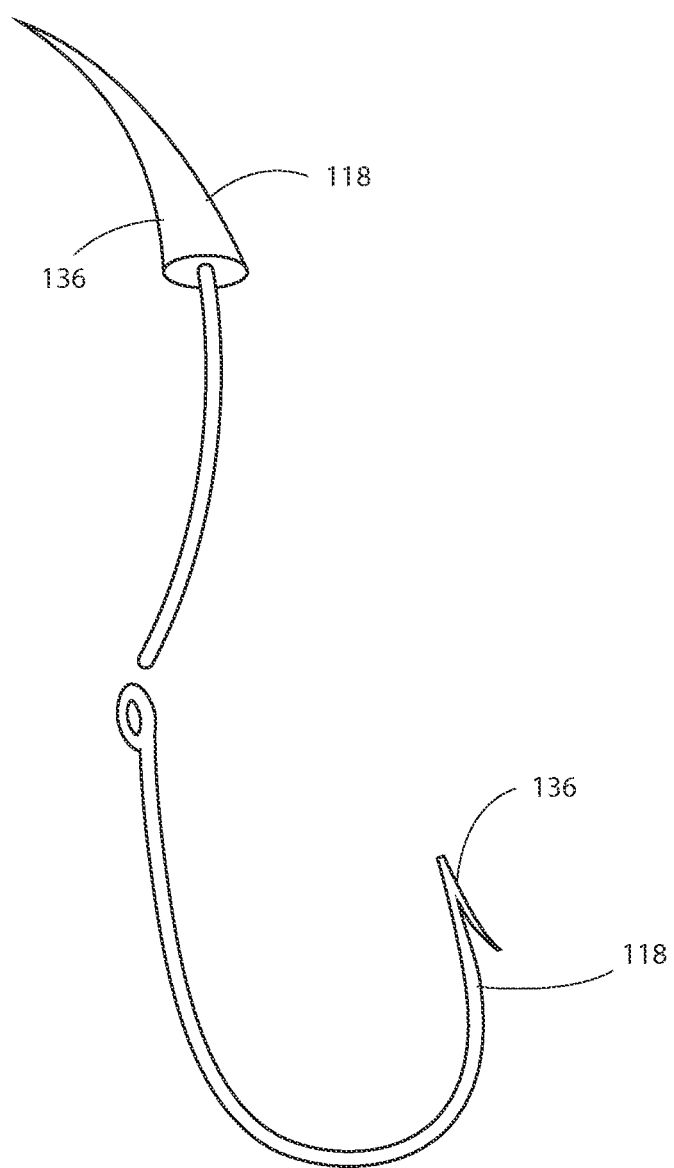
FIG. 17 is a perspective view of a "J" shaped needle as used in a RAFT breast augmentation/reconstruction procedure, with thread swaged onto one end thereof.

The needle embodiments of the present invention may also be provided with one or more of a series of alternative design stops, as depicted in FIG. 11-17. In FIG. 11, an end 114 of a needle 116 is depicted with an arrowhead shaped stop 118. The stop could be either threaded onto the end 114 of the needle 116 so that its position could be adjusted by the surgeon, or swaged into a fixed position. The stop 118 could also be provided in different lengths. A suture 120 may also be swaged into the stop 118. In FIG. 12, a stop 118 shaped like a ball 122 may also be provided, again either with internal threads to permit adjustment by the surgeon or swaged into a fixed position. In FIG. 13, a stop 118 comprises a fin 124, one or more of which extends radially from the needle end 126. The fins 124 may be provided as part of a sleeve 128 that could be threaded onto the needle end 126, or swaged directly onto the needle end 126. FIGS. 14 & 15 depict another stop 118 comprised of one or more retractable barbs 130 which may be either threaded onto the needle end 132 (FIG. 14) or swaged into fixed position onto the needle end 132 (FIG. 15). The barbs are swivel mounted so that a retainer 134 may be slid down the needle end 132 to hold them in a retracted position for removal of the needled end 132 at the completion of the surgical procedure. FIGS. 16 & 17 depict other stops 118 comprised of an arrowhead shape, or fish hook, or cone, or barb 136, with alternate locations of the eyelet 138 (FIG. 16) for attaching the suture. In essence, the stop designs shown are exemplary, the function of the stop being to give the surgeon a physical indication of the needle position during the course of the surgery by mechanically restricting exiting of the needle end from the patient.

A specially shaped needle 140 is depicted in FIG. 18, especially intended for use in a RAFT surgical procedure. It comprises essentially a "J" shape of a longer relatively straight portion 142 transitioning into a more sharply curved portion 144 with pointed. cutting end 146. The curved portion is preferably a beveled, cutting shape, such as a trilateral cross sectional shape 148, to facilitate its being driven into the deep tissues of the patient's chest. The beveled cutting shape may extend further into the straight portion, depending on the particular technique, patient anatomy, or surgeon preference. A suture 150 may be either passed through an eyelet 152 at the opposite end 154, or swaged into fixed location thereat. Its use in a RAFT procedure is explained in greater detail, below.

Figure 19:
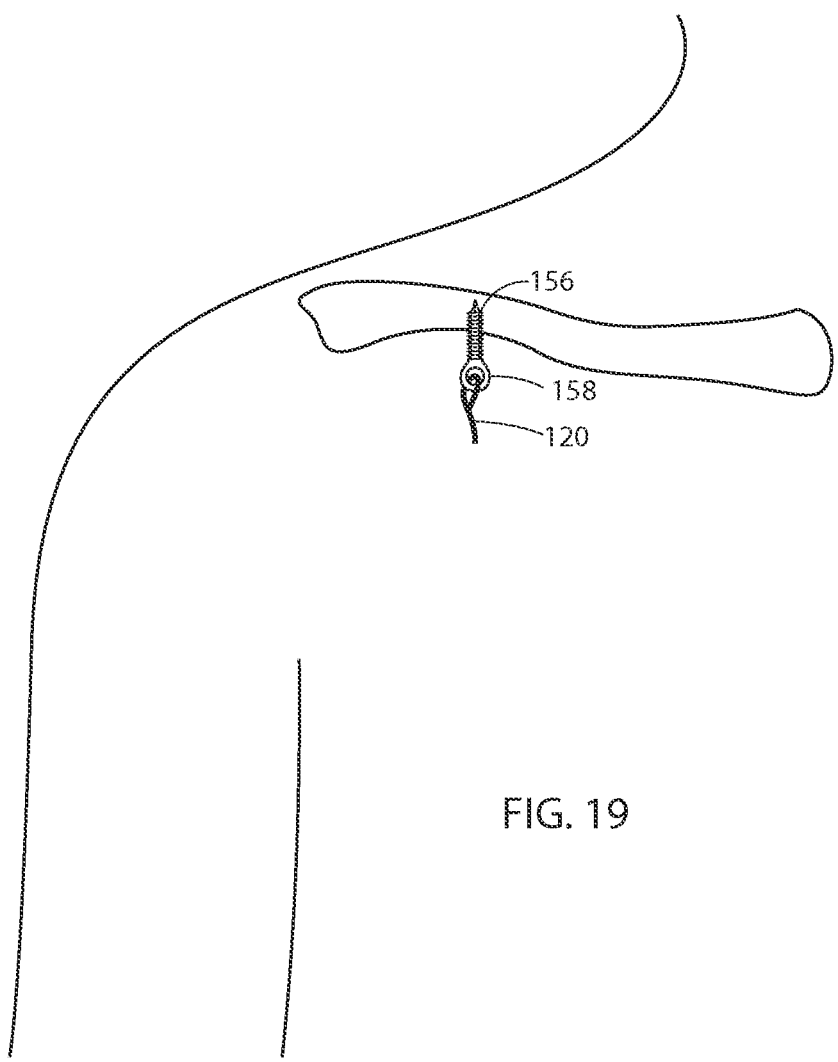
FIG. 19 is a partial cutaway view of a bone anchor detailing the sutures gathered through a ring with the anchor secured to the clavicle.
Figure 19A:
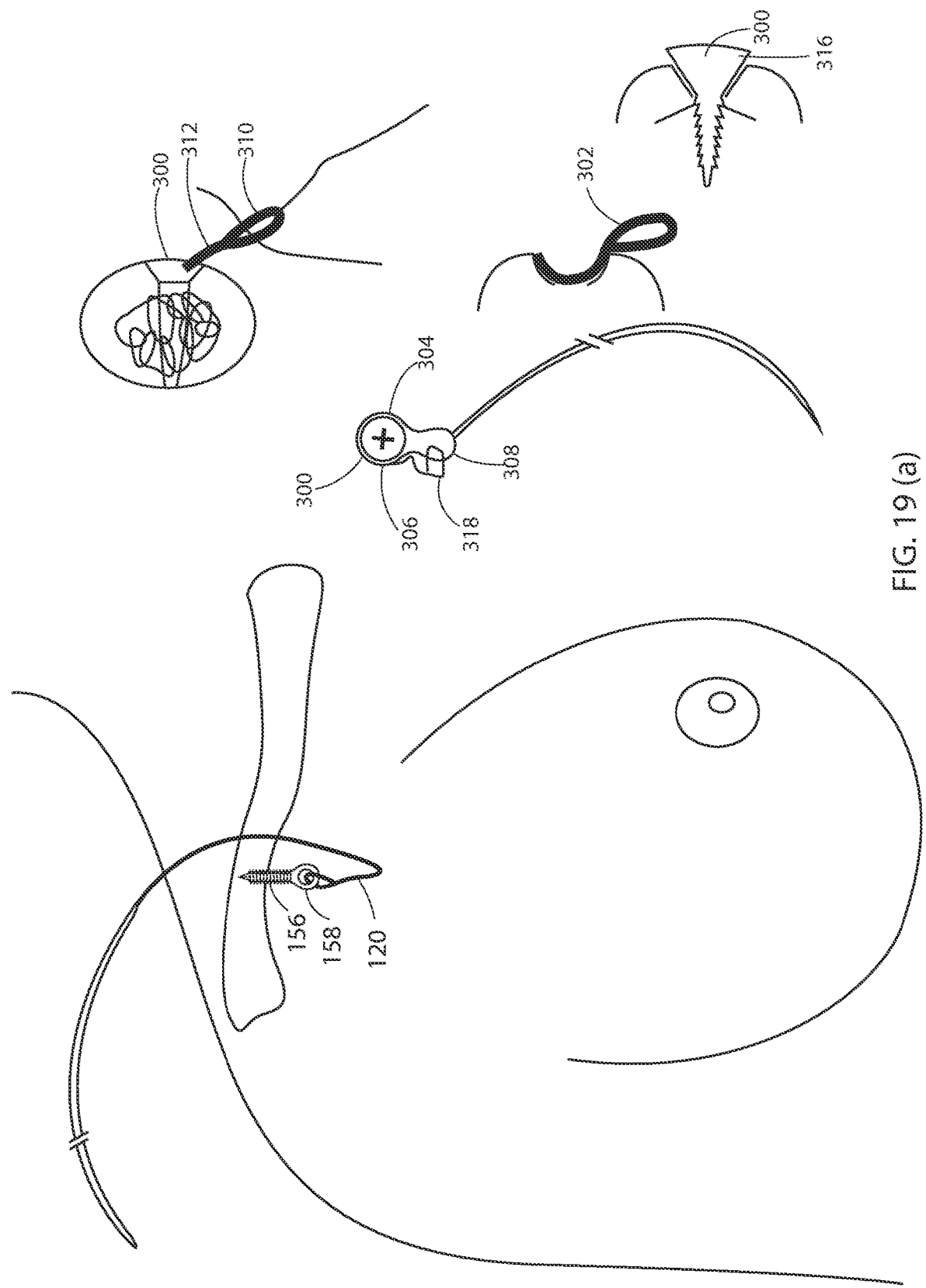
FIG. 19(a) is a perspective view detailing the bone anchor and various alternative embodiments thereof.

As depicted in FIG. 19, a bone anchor 156 may be screwed into or otherwise attached to a patient's clavicle in a RAFT or other breast augmentation/reconstruction procedure for gathering the one or more sutures passing in and around the breast and securing them after the reconstituted breast is desirably positioned. The bone anchor may include a ring or washer 158 for receiving the suture(s) 120 and which allows them to be individually adjusted in length before being affixed.

FIG. 19(*a*) depicts various alternative embodiments for the bone anchor 156 including different arrangements for attaching the suture 120. As shown therein, in a first embodiment the bone anchor preferably comprises an orthopedic, Phillips head screw 300 which is preferably countersunk into the clavicle so as to be flush with the surface of the clavicle. A preferably thin, flexible but resilient washer 302 is preferably attached to the screw 300, in one of several optional ways. This washer may be a double washer 304 having a first annulus 306 through which the screw 300 is inserted as it is attached to the clavicle and a second annulus 308 through which the suture(s) may be threaded and then tightened during the surgery. The double washer 304 may be made from any suitable medical grade material for permanent implantation into the patient's body. As an alternative, a washer 310 may be secured to the screw 300, such as with a suture 312 swaged onto the screw 300 so that as the screw 300 is secured the suture 312 remains exposed to support the washer 310 and is not crimped or otherwise has its integrity affected through tightening of the screw 300. In yet another embodiment, the head 314 of the screw 310 may have an annular flange 316 which may engage the annulus 306 to squeeze it between the flange 316 and the surface of the clavicle, thereby providing what is believed to be a more secure positioning of the washer 304 and its annuluses 306, 308 relative to the clavicle. With either of these embodiments, the washer 310 or second annulus 308 may be crimped to capture the suture 120 after it is passed therethrough and fix the suture in place, as desired. Another feature of the bone anchor 156 may be to include a set screw or cam 318 within the second annulus 308 which may be tightened to internally clamp or capture the suture(s) 120 within the second annulus 308. With the set screw or cam 318 feature, the suture(s) 120 may be readily adjusted during, and even after the surgery to achieve the desired patient results. The needle (for example needle 140 as used in the RAFT procedure) may have a suture 120 swaged to an end thereof and a bone anchor 156, such as one of the washers 302, 304, swaged to the other end of the suture 120 to thereby provide a convenient assembly or surgical tool 320 for a surgeon to perform the RAFT procedure or other surgical procedure, thereby saving the time and trouble of the surgeon attaching these elements together during surgery.

Figure 20:
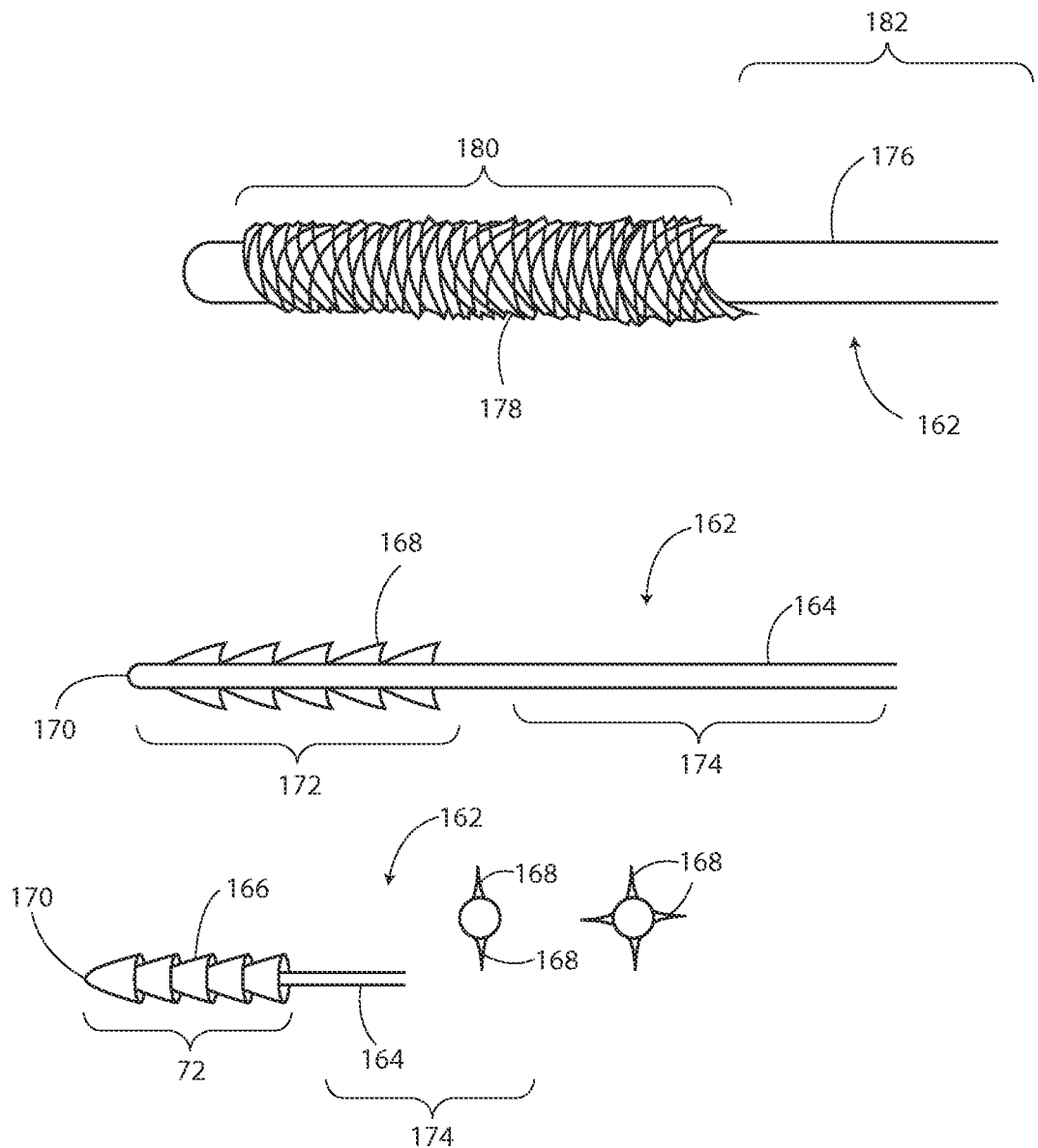
FIG. 20 is a partial view of an end of a tissue dissector and rasp.
Figure 20:
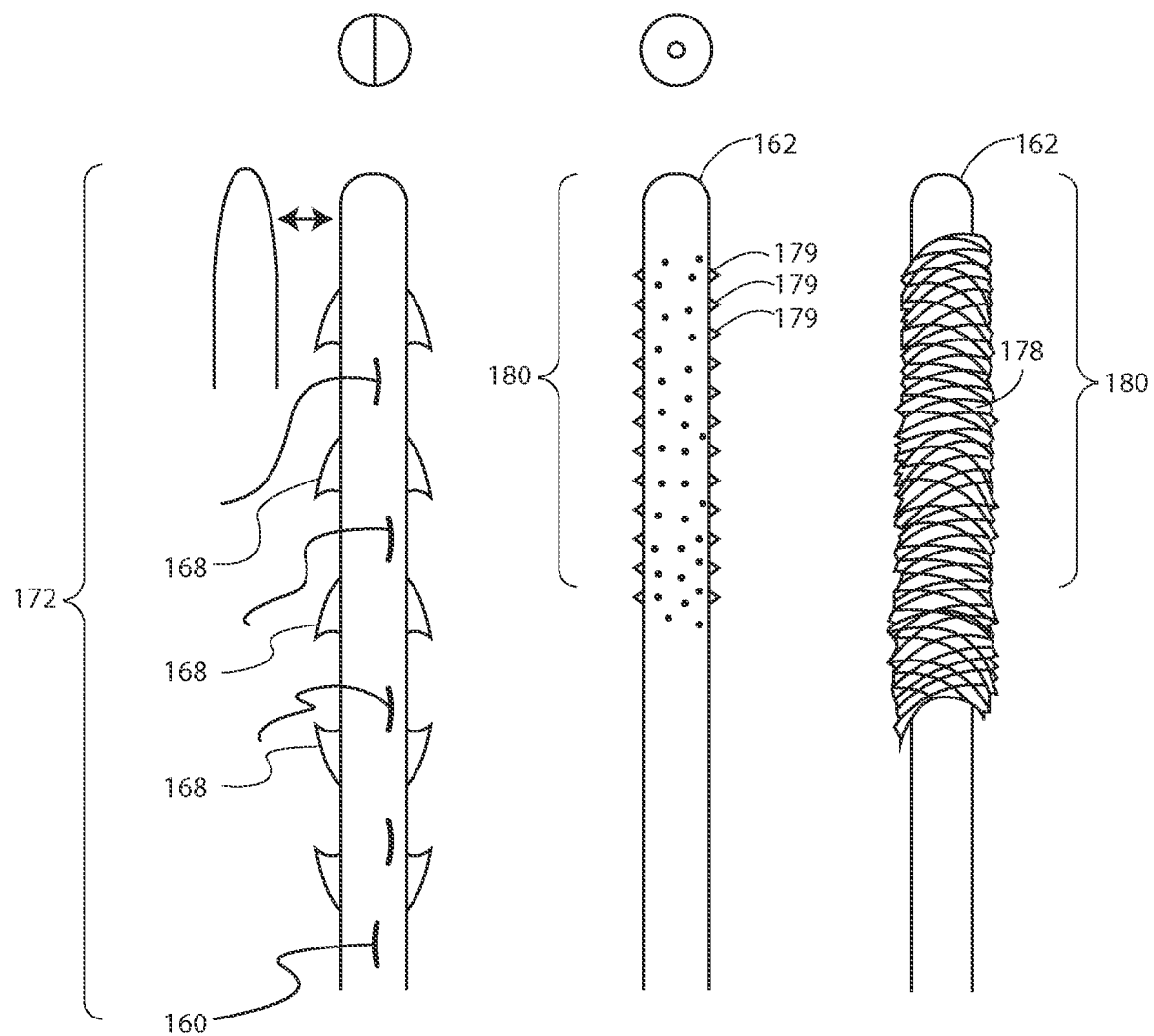

FIG. 20 depicts a tissue dissector 160 and tissue rasp 162. The tissue dissector 160 comprises a relatively long, thin rod 164, solid or hollow, characterized by a series of points or ridges or cones 166. Alternatively, a more aggressive dissector 160 could include shark fin like winglets 168 or other more aggressive cutting structures. The rod 164 could be spatulated or round, and would preferably have a rounded, non-cutting tip 170. The tissue dissector preferably has an active end 172 and a passive or non-acting central portion 174 and a thickness of between about 1 mm to about 3.5 mm. The tissue rasp 162 has a thin preferably metal rod or hollow cannula 176 with a series of rasp-like grooves 178 oriented in various directions, as desired to achieve what may be generally considered as a more aggressive surface than a tissue dissector's active end 172. The grooves 178 could be oblique, orthogonal, or otherwise, and of different and varying depths to achieve the desired degree of aggressiveness. The tissue rasp 162 has an active portion 180 containing the grooves 178 and an inactive portion 182. As explained above, these are similar surgical tools but generally the rasp is intended to provide a more aggressive abrading surface, while the tissue dissector is intended to provide more of a cutting or nicking effect on taut connecting tissues.

FIG. 20(*a*) depicts the working or active ends 172, 180 of representative tissue dissectors 160 and tissue rasps 162. For example, in one view depicted in FIG. 20(*a*) a tissue dissector 160 has a series of shark fin like winglets 168 arranged with their cutting edges in opposite directions to provide a cutting action in both directions as the surgeon moves the tissue dissector in and out and along a tissue plane. These shark fins 168 are also shown oriented at 90° about the circumference of the spatulated, active end 172. A tissue rasp 162 is depicted having a generally cylindrical shape, with circular cross section, and having a series of teeth 179 extending generally radially from its surface. These teeth can be formed in a myriad of shapes and sizes, with sharp or blunt ends, with hooks or not, or otherwise to obtain the desired results during use. A second rasp 162 is also shown, similar to that depicted in FIG. 20, to again illustrate the myriad of groove shapes, depths, and arrangements that can be provided to achieve the desired aggressiveness depending on its intended use.

Figure 21:
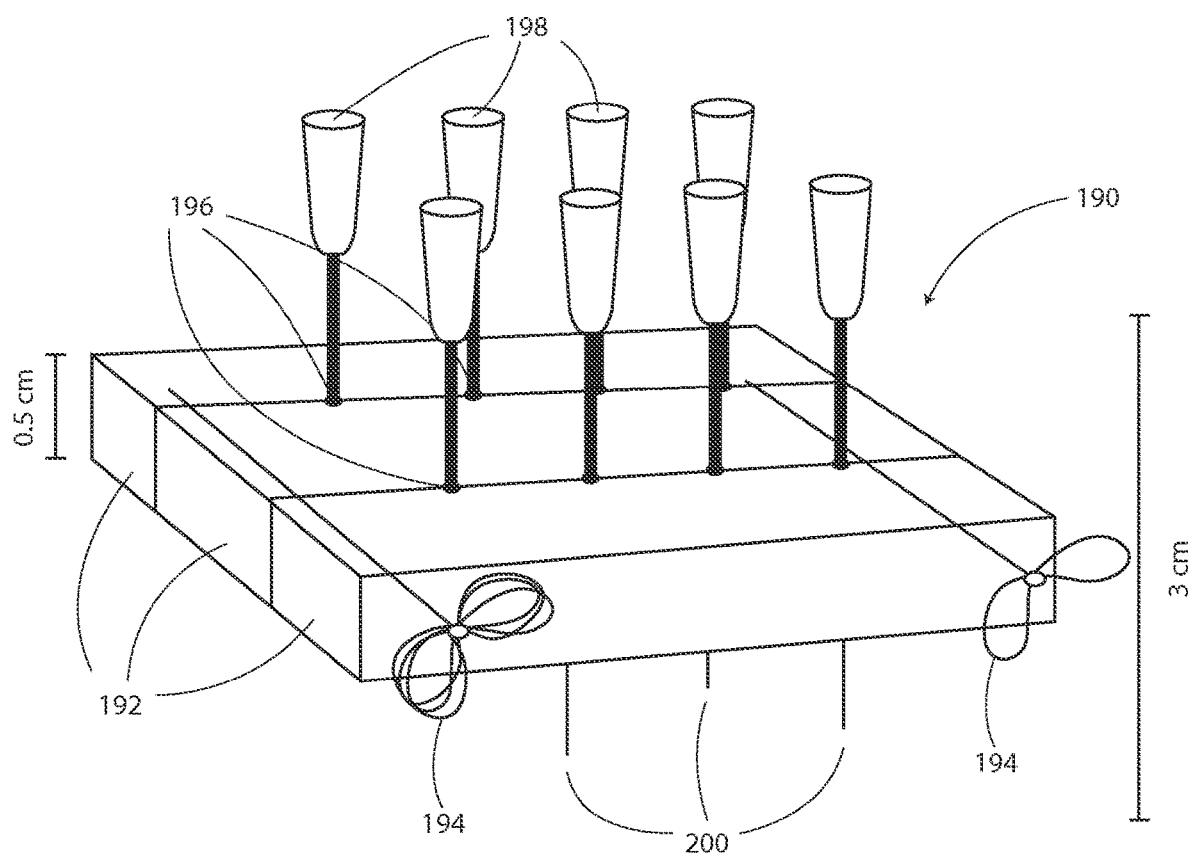
FIG. 21 is a perspective view of a first embodiment of a tissue mesher invention comprised of three rectangular solids screwed together with needles extending through a matrix of eight holes.
Figure 22:
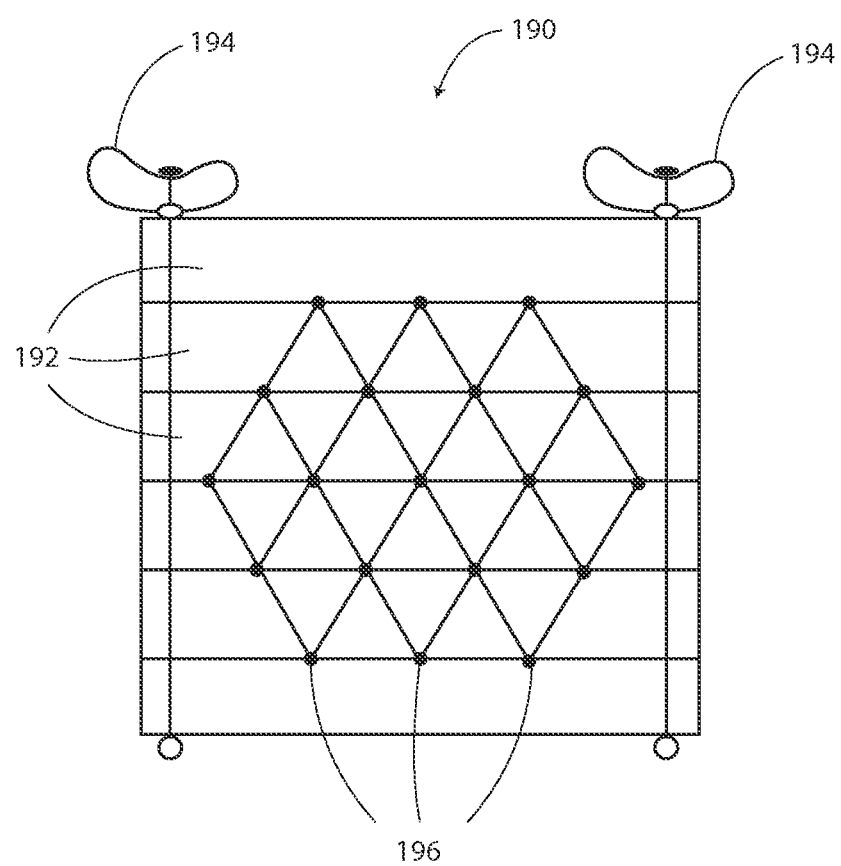
FIG. 22 is a plan view of a second embodiment of the tissue mesher with a matrix of nineteen holes.
Figure 23:
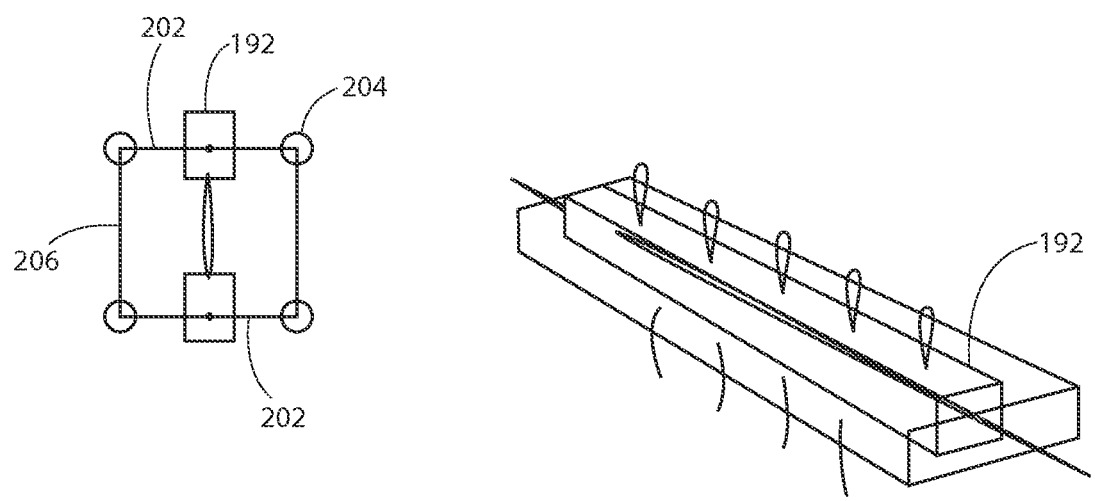
FIG. 23 is a perspective view of a third embodiment of the tissue mesher arranged in a sliding framework to provide lateral translation of the needles.
Figure 24:
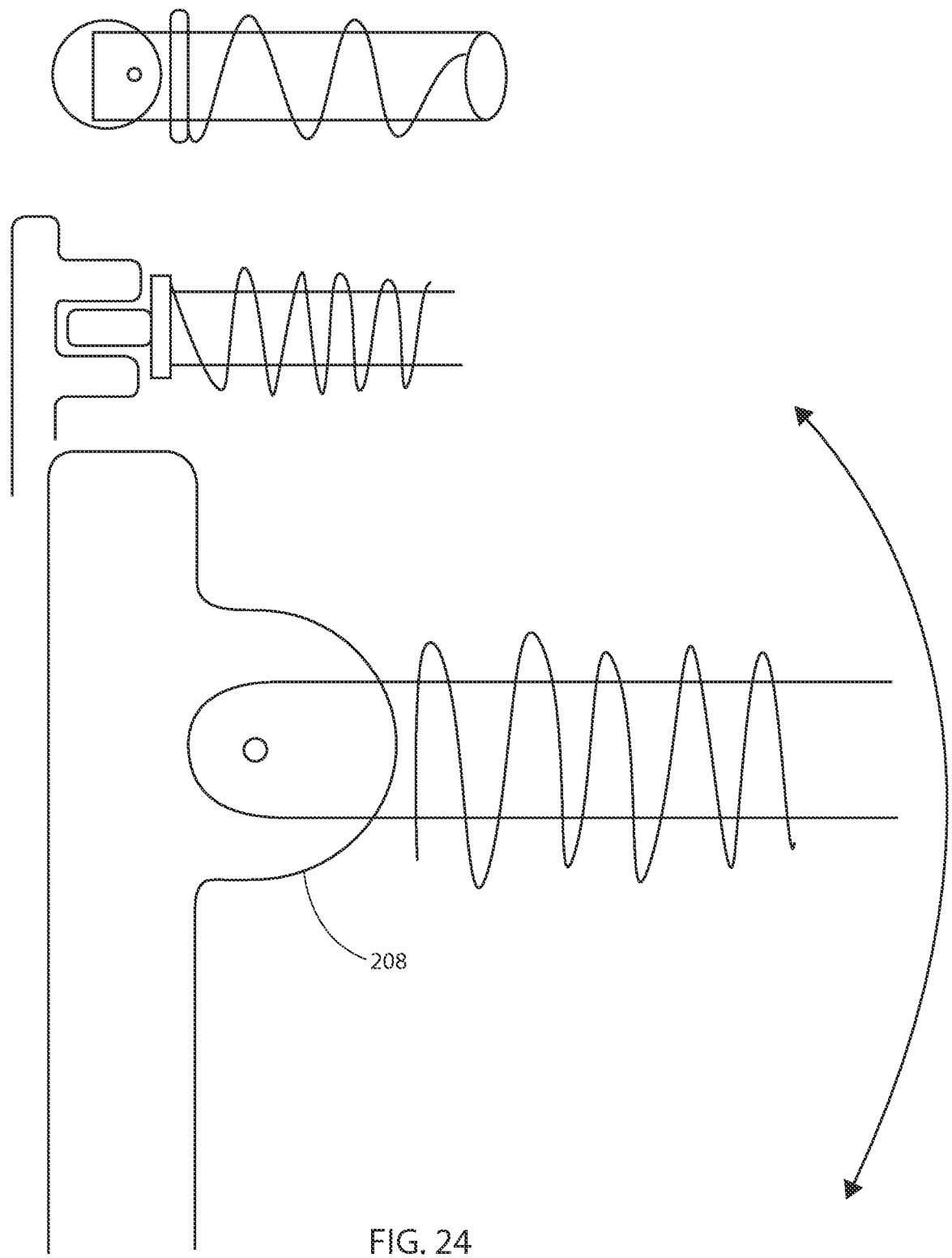
FIG. 24 is a partial view of several articulated joints to permit lateral translation of a tissue mesher or grommet jig.
Figure 25:
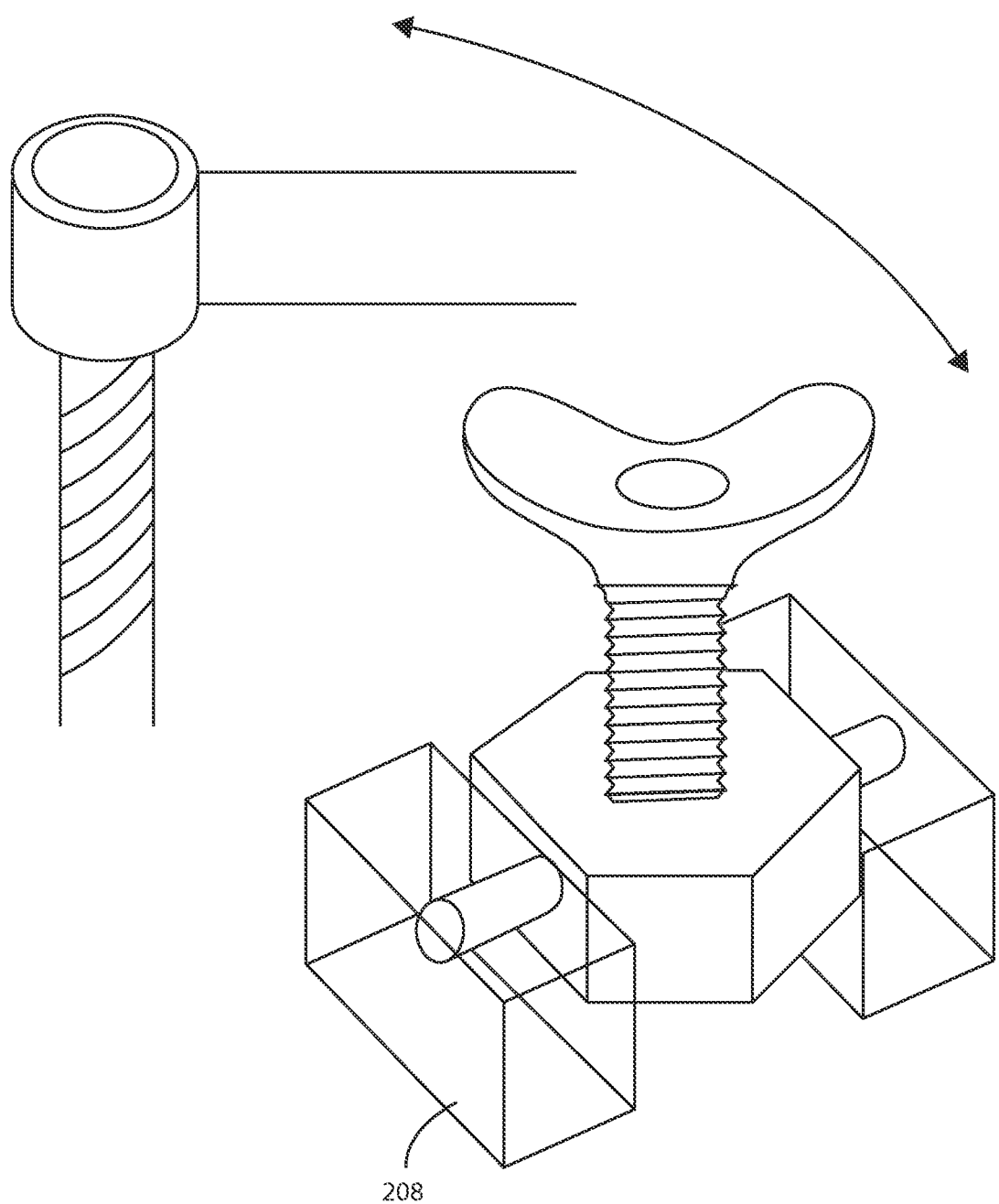
FIG. 25 is a partial view of several articulated joints to permit lateral translation of a tissue mesher or grommet jig.
Figure 26:
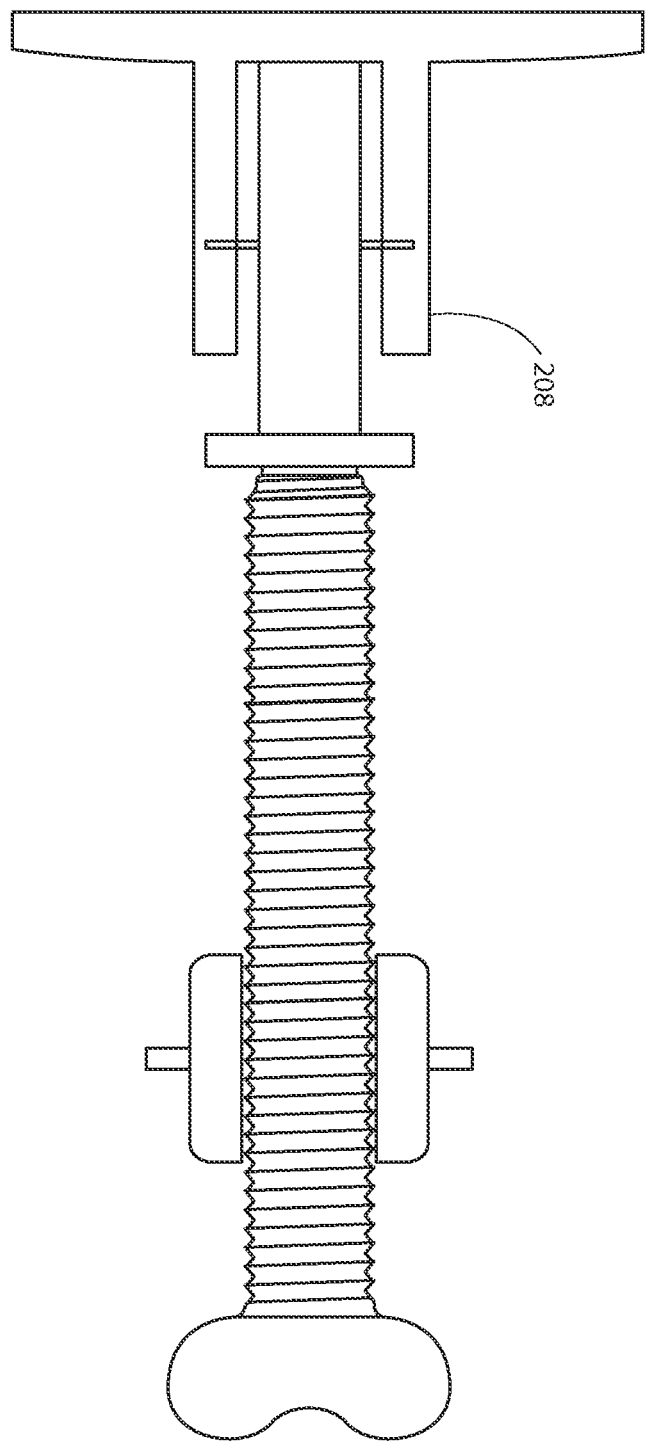
FIG. 26 is a partial view of yet another articulated joint to permit lateral translation of a tissue mesher or grommet jig.
Figure 27:
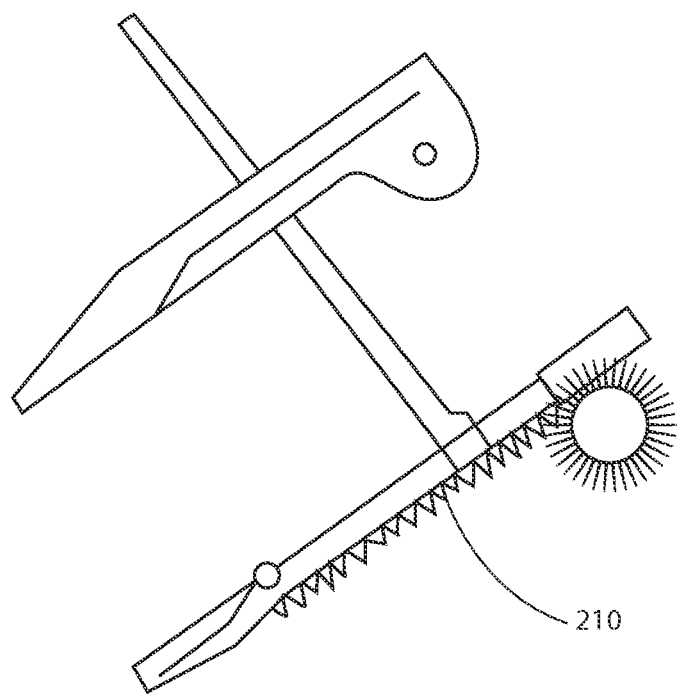
FIG. 27 is a side view of a rack and pinion drive for a tissue mesher to provide lateral translation of the needles.
Figure 28:
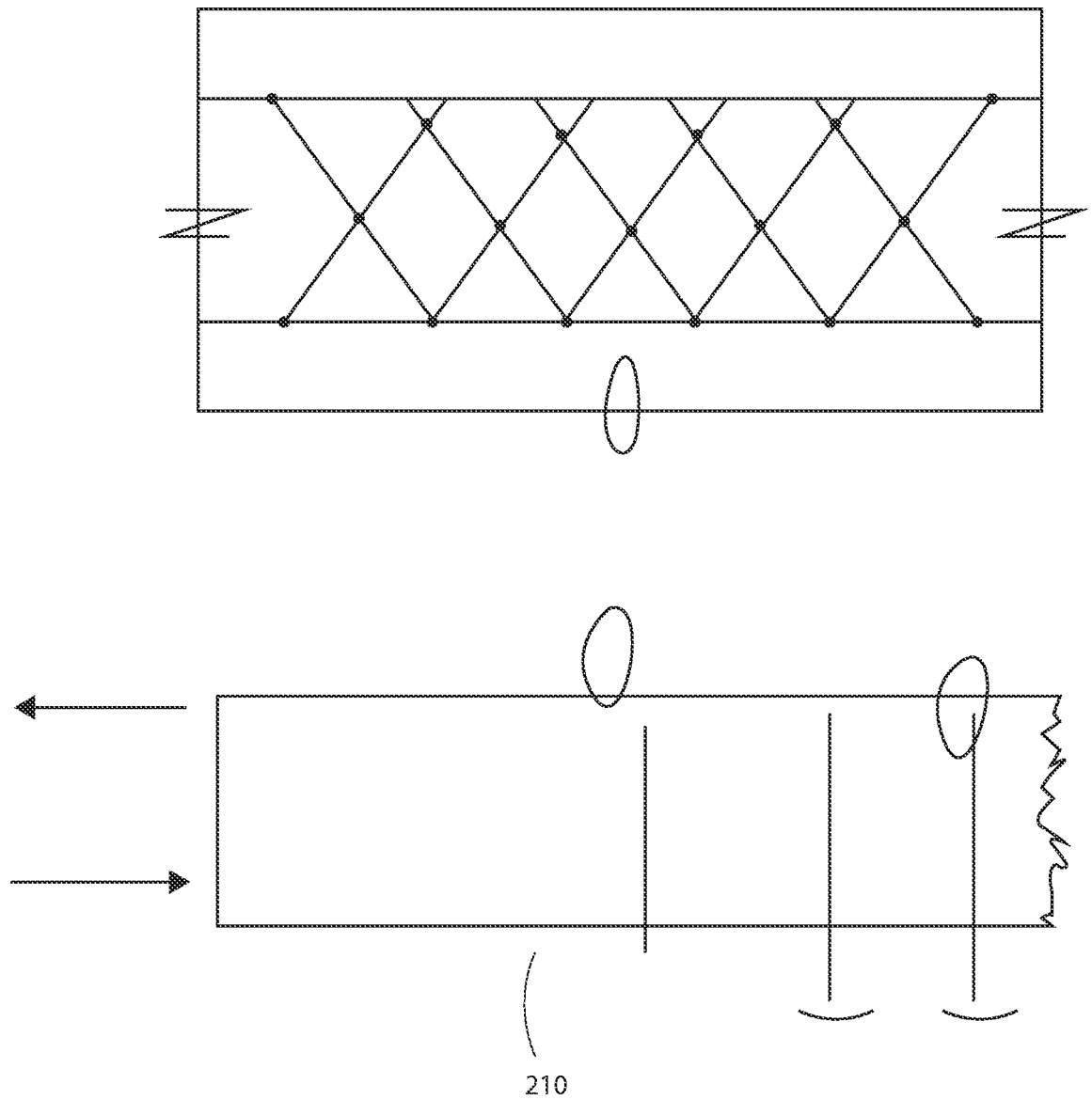
FIG. 28 is a plan and side view of a tissue mesher with yet another matrix of needles.
Figure 29:
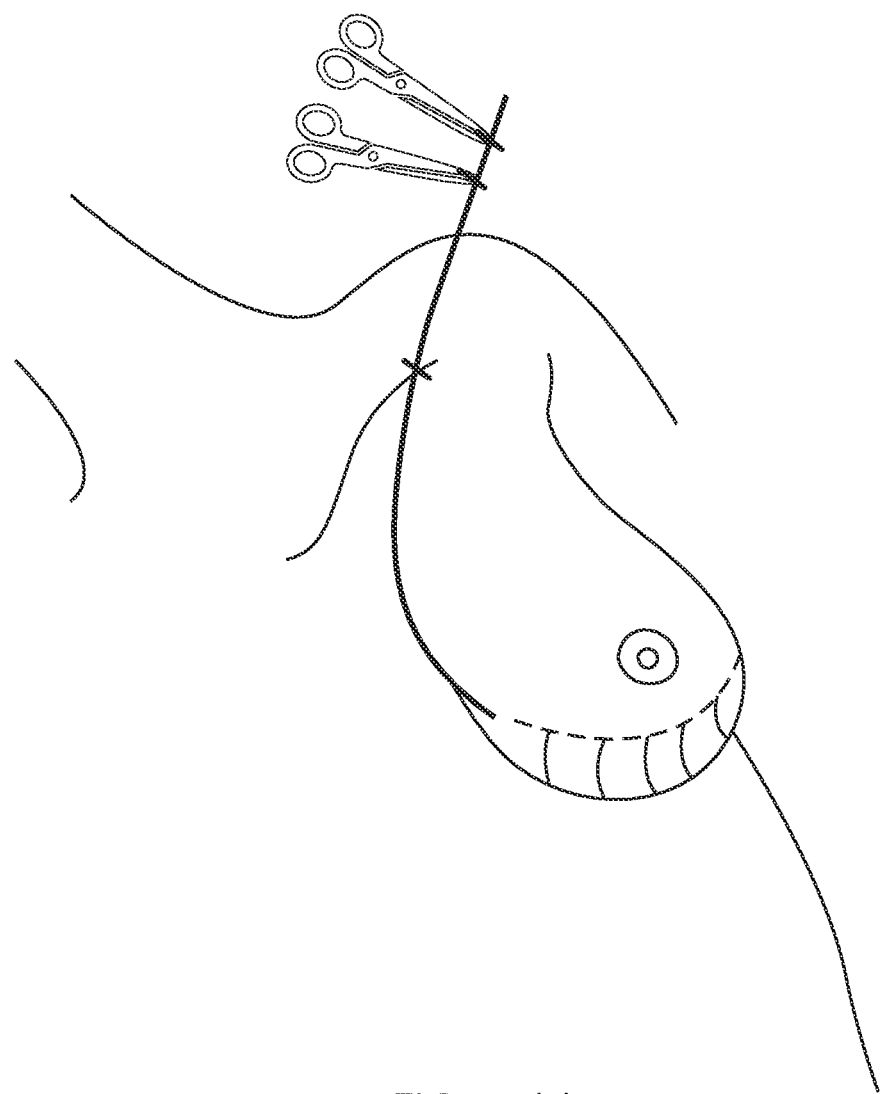
FIG. 29(a)-(g) are frontal views of a patient detailing the method of performing a RAFT breast augmentation/reconstruction.
Figure 29:
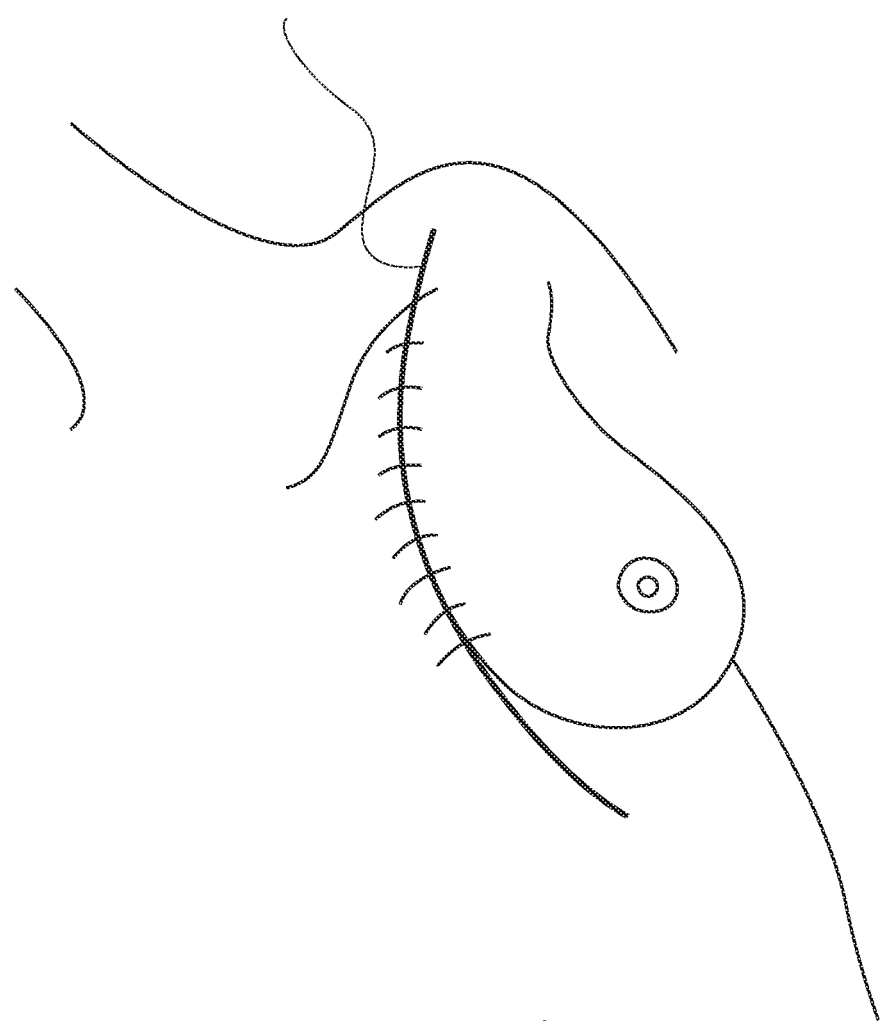
Figure 29:
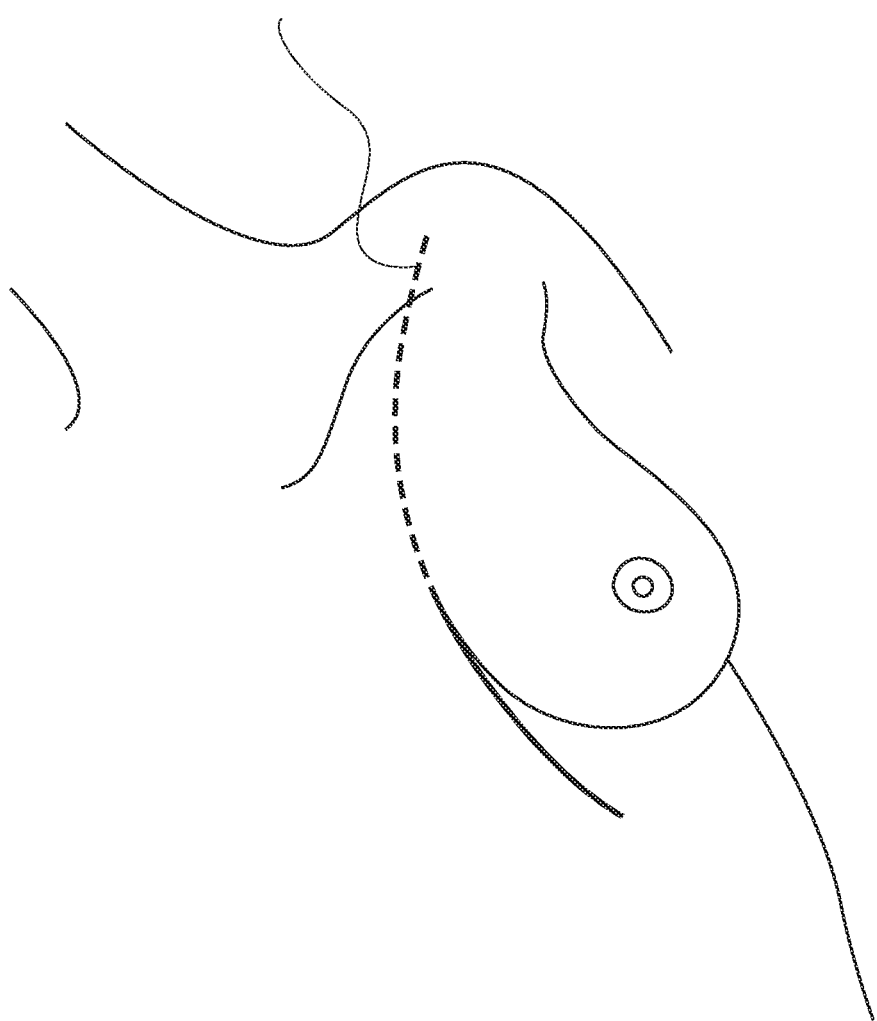
Figure 29:
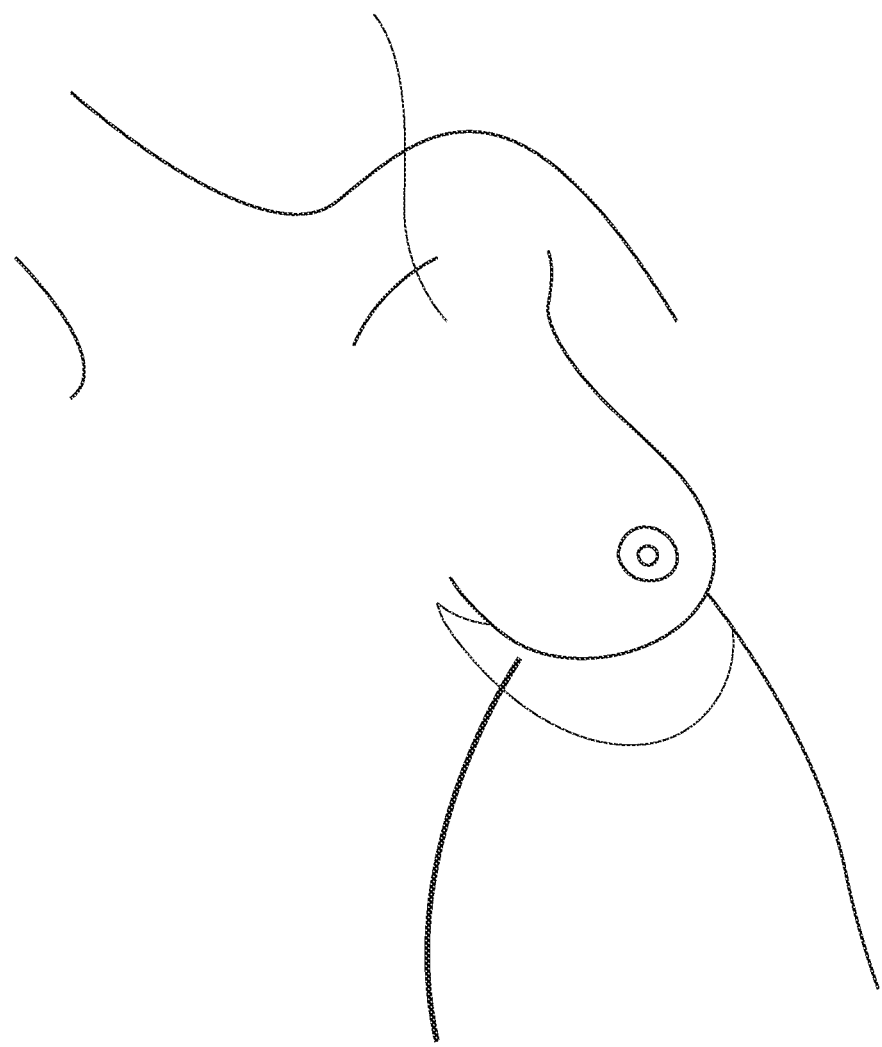
Figure 29:
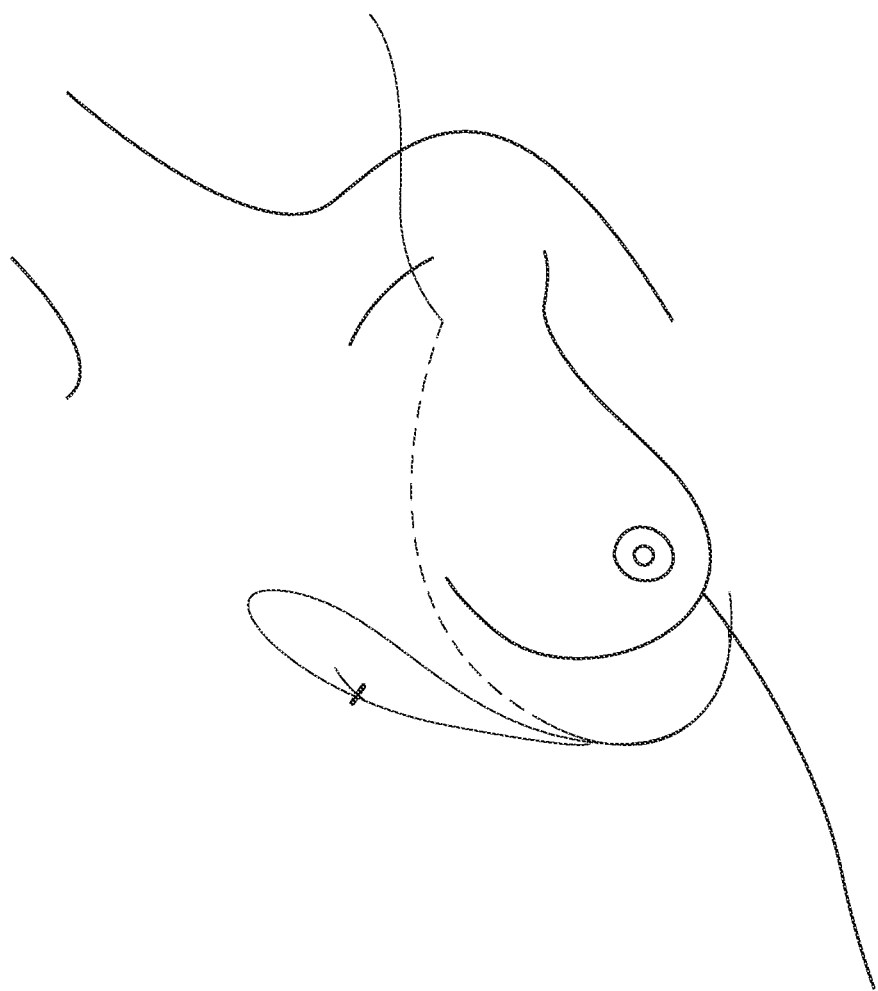
Figure 29:
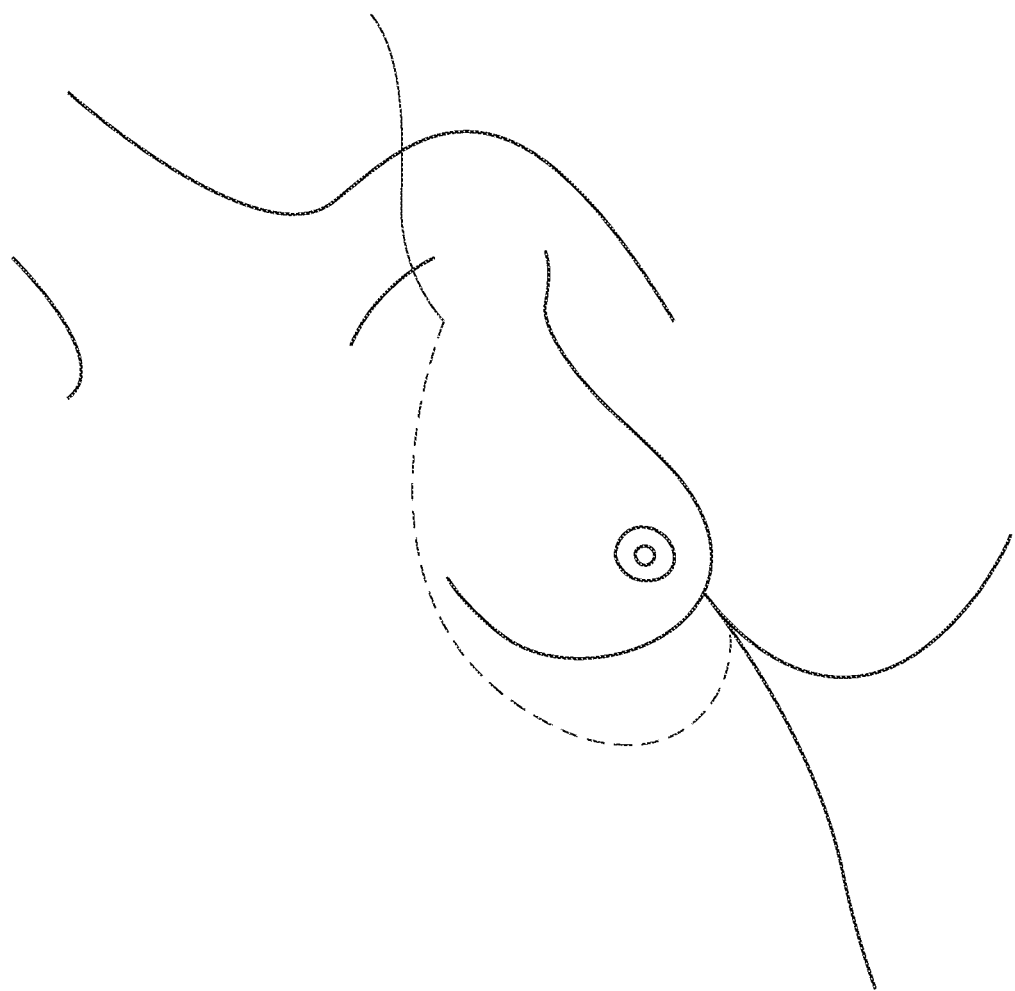
Figure 29:
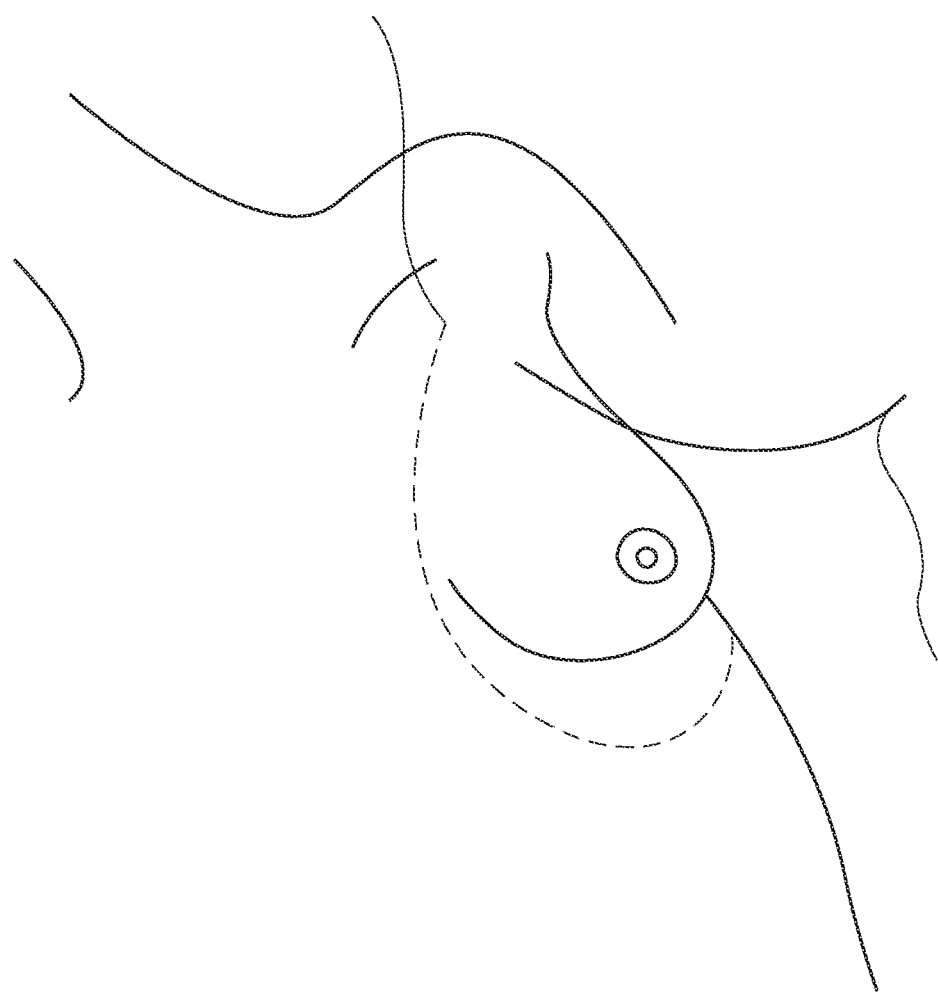

The tissue mesher 190 is shown in its various embodiments in FIG. 21-28. As shown in FIG. 21, three rectangular blocks 192 may be secured together with a pair of threaded rods and wing nut fasteners 194. A matrix of cylindrical holes 196, shown in a 2×4 pattern in FIG. 21, are formed between the blocks and each of which receives and clamps e.g. a hypodermic needle 198 with a sharp, cutting edge point 200. The needles could alternatively be sharpened rods, or other similar cutting pointed instruments, either hollow or solid. This embodiment of the tissue mesher 190 allows the cutting points to be positioned at different depths which provide for creating a three dimensional or two dimensional tissue block, as explained, supra. As shown in FIG. 22, the tissue mesher 190 may be provided with different matrices in essentially the same multi-block, fastened structure. As depicted, a six block 192 matrix of nineteen holes 196 may be readily formed for clamping cutting points at varying, or the same, depth. In order to provide for controlled lateral translation of the cutting points, as depicted in FIG. 23 a tissue mesher 190 similar to those already described may be slidably mounted to a pair of cross rails 202 secured at their ends 204 with a pair of support rods 206. When lateral movement is desired to make the incisions, the mesher 190 is first pressed against the dermis desired to be treated and then slid along the rails 202. FIG. 24-26 depict variations of swivel or articulated couplings 208 which may be similarly used to mount the tissue mesher and provide for controlled movement of the sharp cutting points (not shown) to create the desired incisions. FIG. 27-28 depict rack and pinion arrangements 210 also for achieving controlled lateral translation of the tissue mesher.

Various of the foregoing inventions may be provided in a surgical kit, for single use or as a reusable kit, for a surgeon to purchase and perform one of the surgical procedures described herein. The inventor contemplates that as these inventions are commercialized various ones of these instruments will be found to be included in one or more kits, as well as which variations of the individual instruments from amongst the alternative embodiments described herein. Thus, the inventions are not considered as being limited to the described embodiments but instead should be limited solely by the metes and bounds of claims as they are drafted and presented in a non-provisional application claiming priority to this provisional application.

Figure 30:
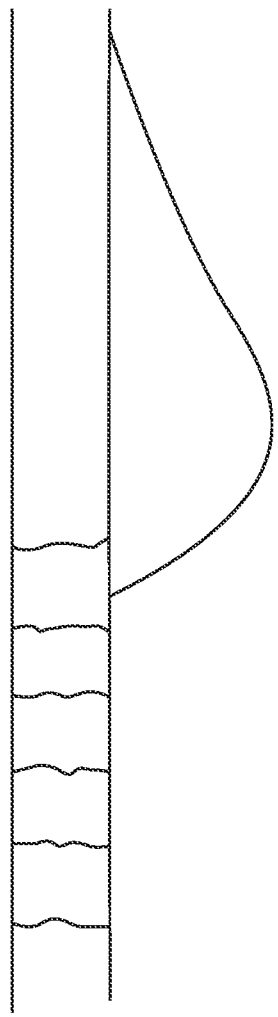
FIG. 30 is a side view of a normal breast, detailing the vertical connecting tissue otherwise restricting abnormal cephalic movement of the upper abdominal tissue.
Figure 31:
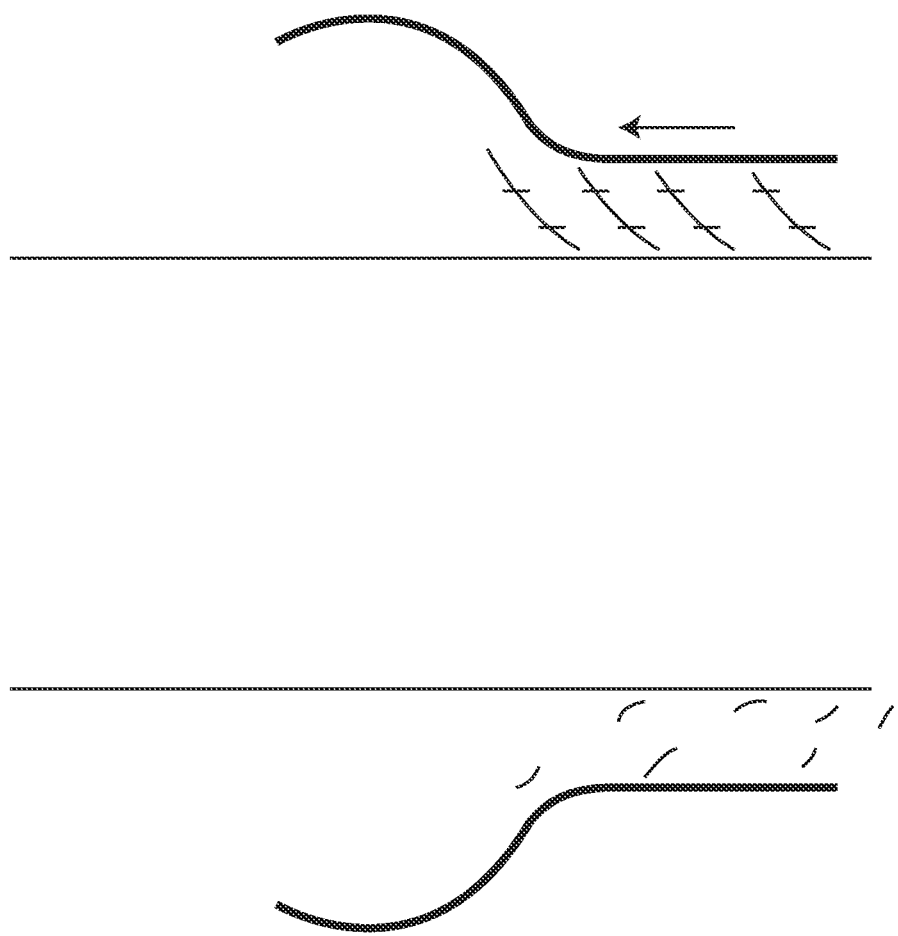
FIG. 31 is a side view detailing the cephalic sliding permitted as the vertical connecting tissues are "nicked" by a tissue mesher to break.
Figure 32:
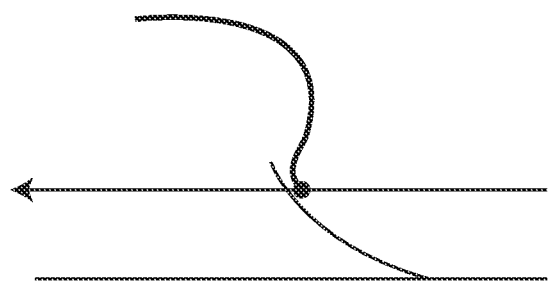
FIG. 32 is a side view detailing how the abdominal tissues mushroom as the RAFT procedure completes, with the vertical connecting tissue released.

Use of a number of these inventions will now be explained in the context of the RAFT breast augmentation/reconstruction procedure, and by reference to FIG. 29(a)-(g); and FIG. 30-32.

A—Design of the Arc of Abdominal Anterior Thoracic Tissue to be Purse Stringed and Advanced:

Depending upon the abdominal tissue laxity and the amount of tissue required for the reconstruction, up to a 12 cm wide arc of upper abdominal/lower thoracic tissue can be mobilized and brought up to form a breast or to augment a pre-existing one. The pattern of the purse string arc determines the tissue that will be advanced. This arc is outlined on the patient skin prior to the surgery. See FIG. 29(a).

The arc that will be purse stringed and advanced cephalically starts at the medial end of the inframammary fold (or where the inter-mammary fold starts), then continues caudally and laterally up to a level just anterior to the mid axillary line to extend back up cephalically at the level of the lateral end of the inframammary fold, or what is more correctly referred to as the end of the lateral mammary fold. The thread loop will be passed from the clavicle in a deep plane over the bony sternum up to the beginning of the arc. Along the course of the arc, the suture is kept subcutaneous or intra-dermal. Keeping an even level of needle passage is considered important by the inventor in order to avoid accordion curtain like irregular folds as the purse string is tightened. At the lateral end of the arc, the suture dives deep again into the subcutaneous tissue and is advanced medially and cephalically to close the loop up at the starting point at the level of the clavicle.

B—Passing the Looped Thread:

The passing of the suspension suture is the cornerstone of this procedure. This is where the "J" shaped needle invention disclosed herein is put to good use. It preferably is long enough to reach from the clavicle to the upper abdomen with enough shaft length left to handle and guide it. The curvature is like a double "J" and it is preferably rigid to be driven for such a long distance while malleable enough to be steered through the tunnel it slices longitudinally through the dermis with its sharp cutting edges. Maintaining an even depth of the needle as it courses through the preferred immediate subdermal plane is preferable. To that effect, special design of the cutting tissue dissecting tip might be required such as fins or ailerons. When the sutured is pulled, passages that are too superficial will lead to dimpling or puckering of the skin and passages that are too deep will lead to ridging. Since the desired result is an even line fold, it is preferred to stay in the same plane throughout the suspension arc. Alternatively, more than one suture may be passed such that any ridges left by deeper passes of the first suture are captured and brought down to create an even fold.

After making a small slit on the anterior chest wall just under the clavicle, (the level of the clavicular bone anchor) two strong needle holders are required to stepwise advance the needle. See FIG. 29(a). Though two strong, pliers like, needle drivers are currently used, the inventor conceives of a handling device that can effectively grab the needle and drive it down along its long downward spiral passage as it follows the spiral down contour of the sternum to emerge subcutaneously at the level of the breast. The needle tip is first allowed to exit at a point along the previously marked arc, just below the intermammary fold level. See FIG. 29(b). If this hole has been "matured" by liposuction (see below the dissecting of the abdominal apron section), then the needle used does not need to be double pointed. (A long needle such as this one is easier and safer to handle if it is not pointed on both ends.) Holes that have been "matured" by previous repeated cannula passage have loose and destroyed subdermal fibers such that an in and out passage of the needle through the same hole has little chance of catching intact fibers and therefore will not dimple down the skin when tightened.

The needle is then passed in the deep dermal/subcutaneous tissue along the pre-marked arc, coming in and out as necessary through the previous liposuction puncture holes till the end of the mammary fold, in the lateral chest at about the mid-axillary line and the third to fourth intercostal space. See FIG. 29(c)-(f). This last puncture wound is the position of the end of the lateral mammary fold and from there on, the course of the needle comes deep, it could pierce the pectoralis or course along the anterior axillary fold to emerge anteriorly through the original subclavicular incision and complete the loop. See FIG. 29(g).

Pulling cephalically on this suspension loop advances the upper abdominal tissue to the breast area and the purse string effect mushrooms it into a breast dome. See FIG. 30-32. The inferio-lateral portion of the thread in the subcutaneous tissues defines the inframammary and lateral breast folds. Anchoring the loop to the clavicle and tightening it advances the abdominal and lateral thoracic flaps to create a breast mound with new inframammary and lateral breast folds. See FIG. 29(g).

Inserting an implant is one of the alternatives to provide volume. However, lipofilling the mobilized tissue is often the preferred alternative, using one of my patented techniques and devices. Oftentimes these are combined.

C—Dissecting the Abdominal Apron and Mobilizing It:

This is actually the first step of the procedure. It consists of tumescent liposuction of the abdominal apron through 3-8 14 G needle puncture wounds along the previously marked upper abdominal arc with the most lateral puncture at the mid-axillary line, $3^{rd}$ to $4^{th}$ intercostal space (where the lateral mammary fold would naturally end). We make a few additional puncture wounds for liposuction cannula entry around the mid abdomen, the umbilicus and the lower abdomen. The crisscrossing of the cannula tunnels loosen the abdominal wall fibers to a certain extent. Then, through these same puncture wounds, using a special dissecting cannula (as described above), we mobilize the abdominal apron and the postero-lateral thoracic flap.

D—Re-Orienting the Fibers, Deepening the Fold and Relieving the Abdominal Tightness:

To further define the fold and create the natural overhang of a pendulous breast, the fibers that prevent the bulging and mushrooming of the tissue on the inner side of the purse string loop need to be divided. As described before, these fibers have to be divided in a staggered fashion with different fibers cut at different levels to generate an inter digitating expansion. Tissue meshers help re-orient the fascia fibers, relieve tension and eliminate unwanted folds. Dividing the stretched nerves is also achieved. Because pulling or stretching or strangulating sensory nerves causes severe pain, it is also important to avoid grabbing cutaneous sensory nerves in the loop. On the other hand simply dividing the nerves as is done during most operative procedures might lead to some decreased sensation of the territory of the nerve but usually causes no pain. The staggered meshing therefore also serves to cut the nerves and avoid the nerve pain.

E—Tightening the Skin Where Needed:

Tightening of the skin may be achieved with the tissue file and rasp described herein with the post dissection redraping, scarring and contraction maintained with the help of an external adhesive supportive splint and/or internal sutures.

F: Post Op Care Wearing the External Moldable Splint

To complete the treatment, an external splint is applied, which can be formed with transparent surgical tape, an elastic mesh tape or a supportive brassiere otherwise constructed specially for this purpose, to hold the reconstructed breast in position and shape. After a few weeks, the splint may be removed and the patient has achieved the desired result.

Figure 33:
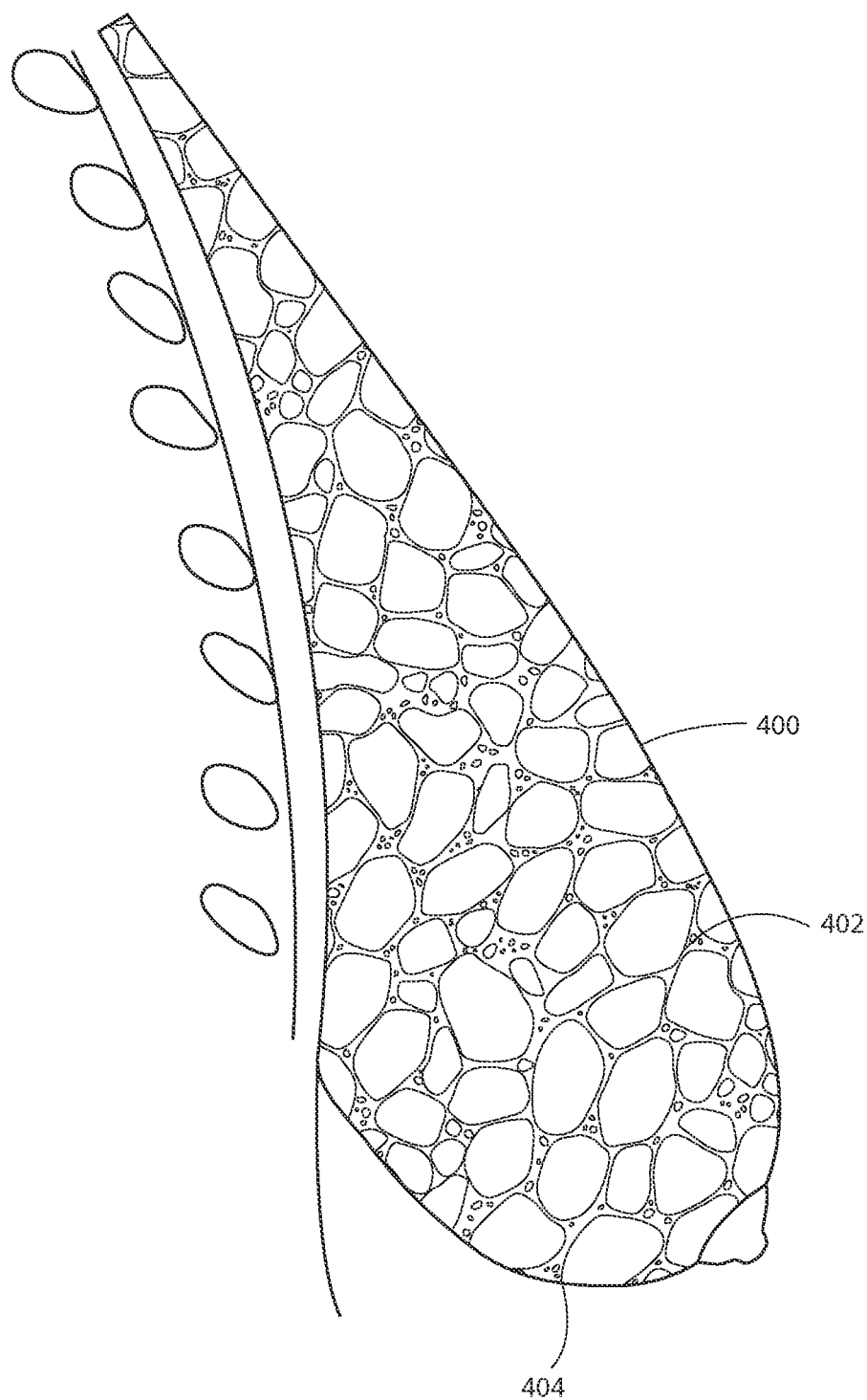
FIG. 33(a)-(c) are side, cross sectional views detailing the method of performing a breast lift using the tissue dissector and tissue rasp inventions.
Figure 33:
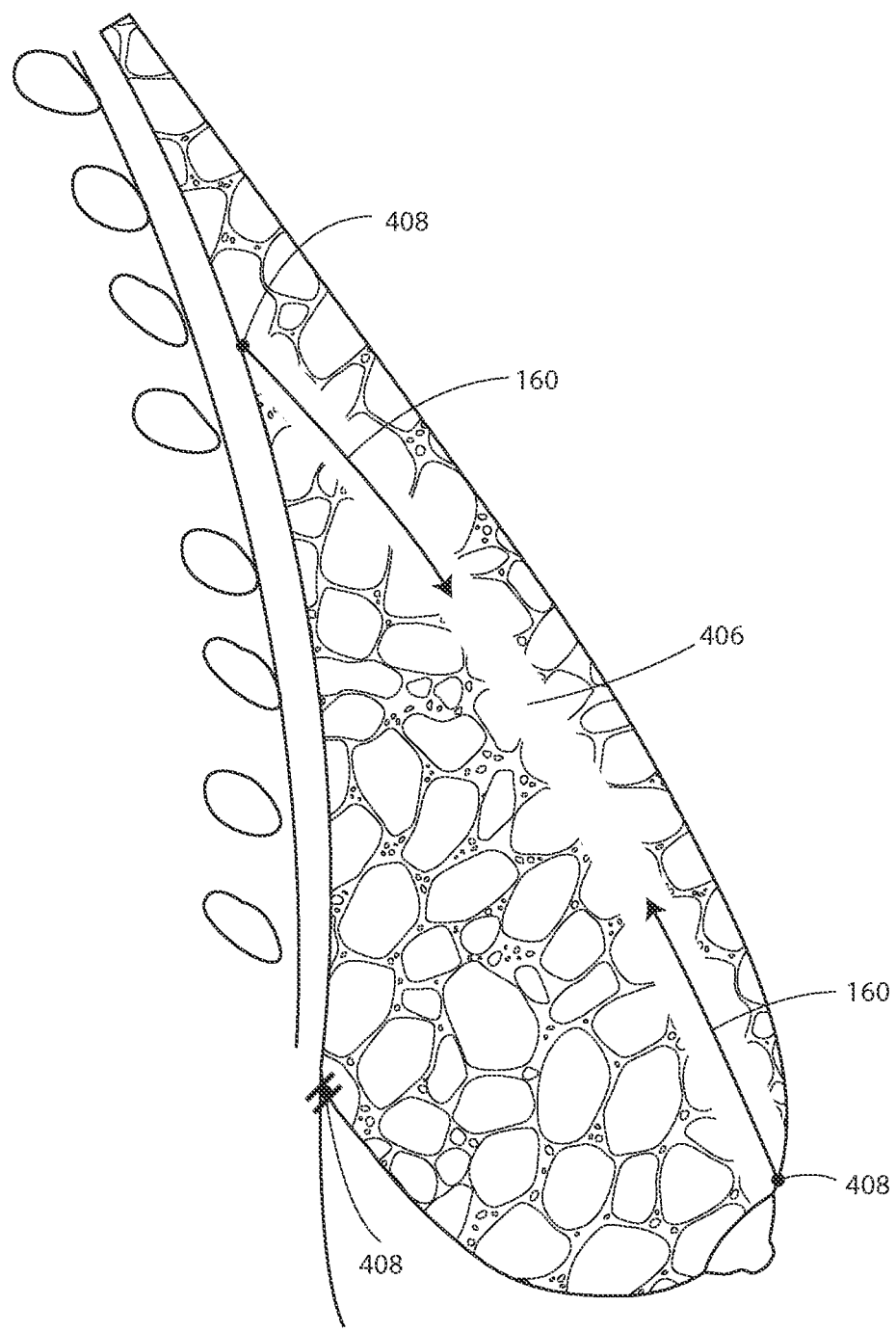
Figure 33:
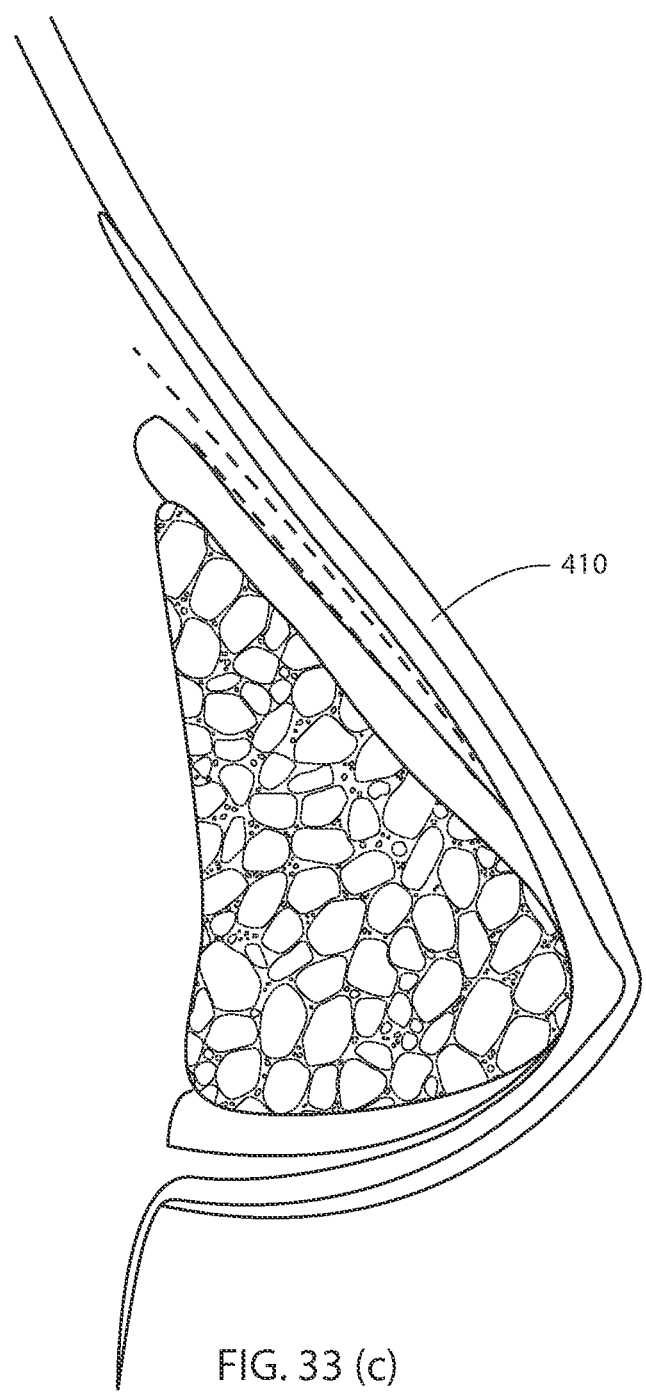

As shown in FIG. 33(a)-(c), the tissue dissectors and rasps disclosed herein may be themselves used, along with the transparent or inconspicuous easy to conceal and wear resistant bra, to perform a breast lift without surgical incisions typified by prior art procedures. For example, a woman suffering from ptosis of the breast, as depicted in FIG. 33(a), as is well known, has a sagging breast with the breast 400 being comprised of glandular tissue 402 surrounded by fat 404 all of which is connected. In this procedure, the breast 400 is first inflated with a suitable fluid such as fat and epinephrine containing physiologic solution to become tumescent which tightens the connecting tissue, and then tissue dissectors 160 are used to cut the connecting tissue between the fat 404 and the glandular tissue 402 to create a space 406, as depicted in FIG. 33(b). Several small dissector entry openings 408 are created in unobtrusive locations to be able to extend the tissue dissector 160 around the glandular tissue 402 and reach and cut most if not all of the connecting tissue. After separation, a tissue rasp (not shown) is inserted through these same openings 408 and the glandular tissue is abraded or irritated/inflamed to incite the desired scarring. Then the breast is lifted into its desired final position and shape, either manually or by use of a small suture to support the breast or with the patient laying on her back, and a preferably transparent bra 410 is applied preferably during this breast moving/shaping process which, when the breast reaches its final position preferably becomes adhesive to the breast and also above the breast and perhaps as high as the clavicle, or around the shoulder as bra straps to hold it in its desired final position and shape. The supportive bra can come in predetermined shapes with a protective sheet for the adhesive layer or can be applied as multiple pieces or strands that overlap and interdigitate to reach the desired shape and support. The breast 400 is then held in position, as depicted in FIG. 33(c), for a somewhat extended time period, perhaps a few or even up to six weeks, while the tissue scarring forms in sufficient rigidity to hold the breast in place without the bra. After achieving the formation of the supporting scar tissue, the bra 410 may be removed (might use the help of an adhesive remover) and the patient is finished with the process having achieved a successful breast lift. The inventor contemplates that this bra 410 is preferably transparent so that the underlying skin tissues may be examined to ensure no complications. Alternatively could be skin colored for better concealment. Also, the bra may be made of a sheet or mesh fiber, or elastic weave, that would be pliable upon application and then could be fixed, for example such as by adding a rigidifying layer or spraying a fixative thereon, to hold it in place. The bra could be made of thin cotton or silk fabric that would cure, could be pre-formed or cut into shape during or before surgery to suit the particular patient's physique. Although depicted and explained as a breast lift, this same method is envisioned by the inventor as being suitable for other tissue engineering applications such as body lifts, tummy tucks or face lifts, for example.

Figure 34:
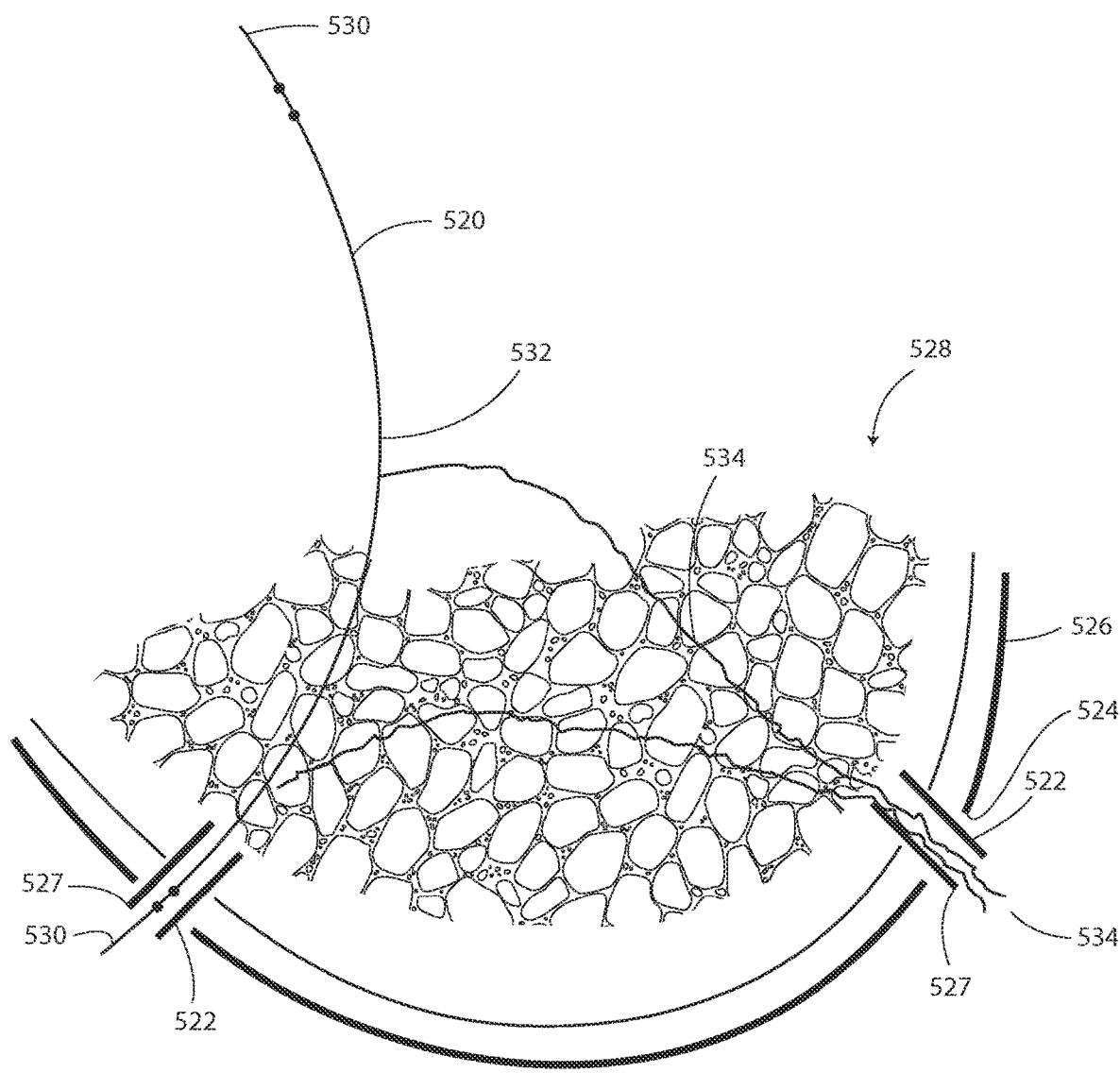
FIG. 34 is a cross sectional view of the breast with the bra supporting it, a pair of grommets inserted over the needle and through the bra with thread passing through one of the grommets.
Figure 35:
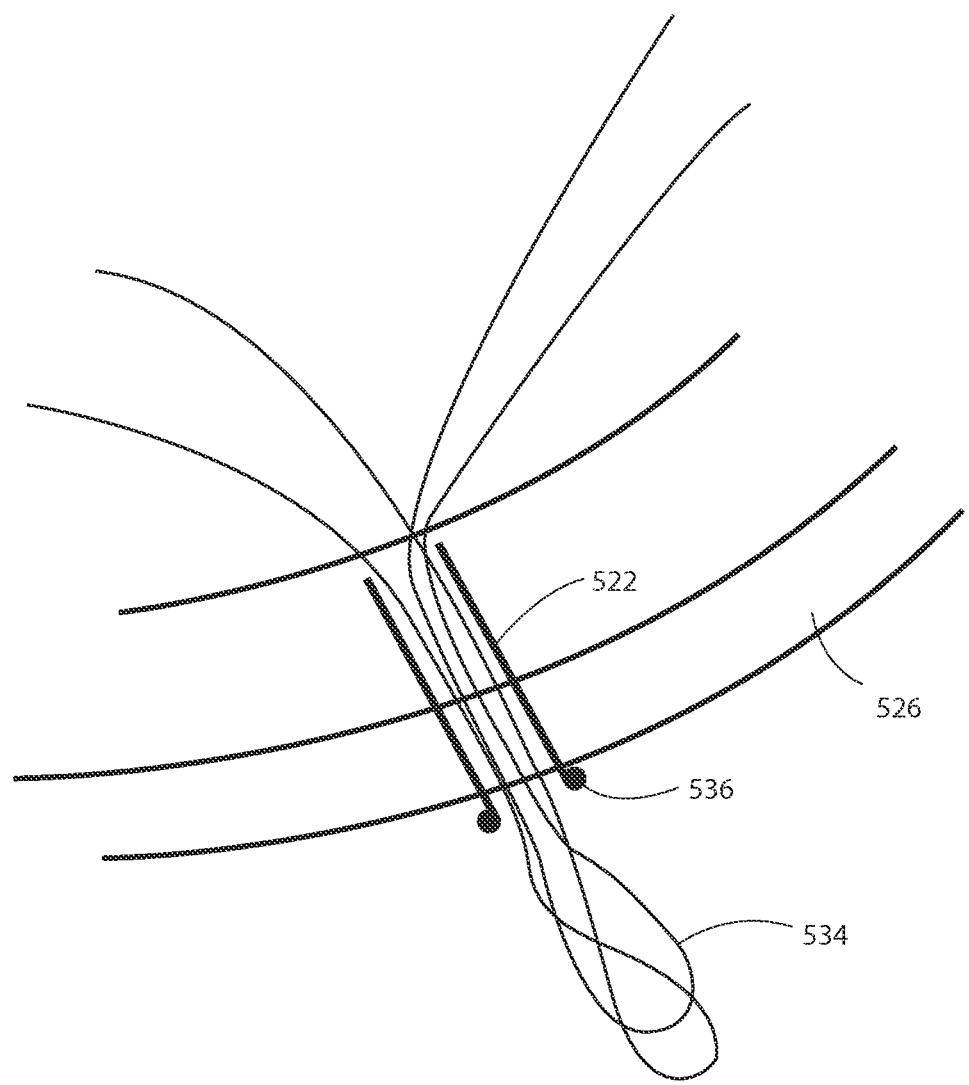
FIG. 35 is a cross sectional view of the breast and bra, with a grommet having a shoulder to hold it in place in the bra and a pair of threads looped together to start the weave.
Figure 36:
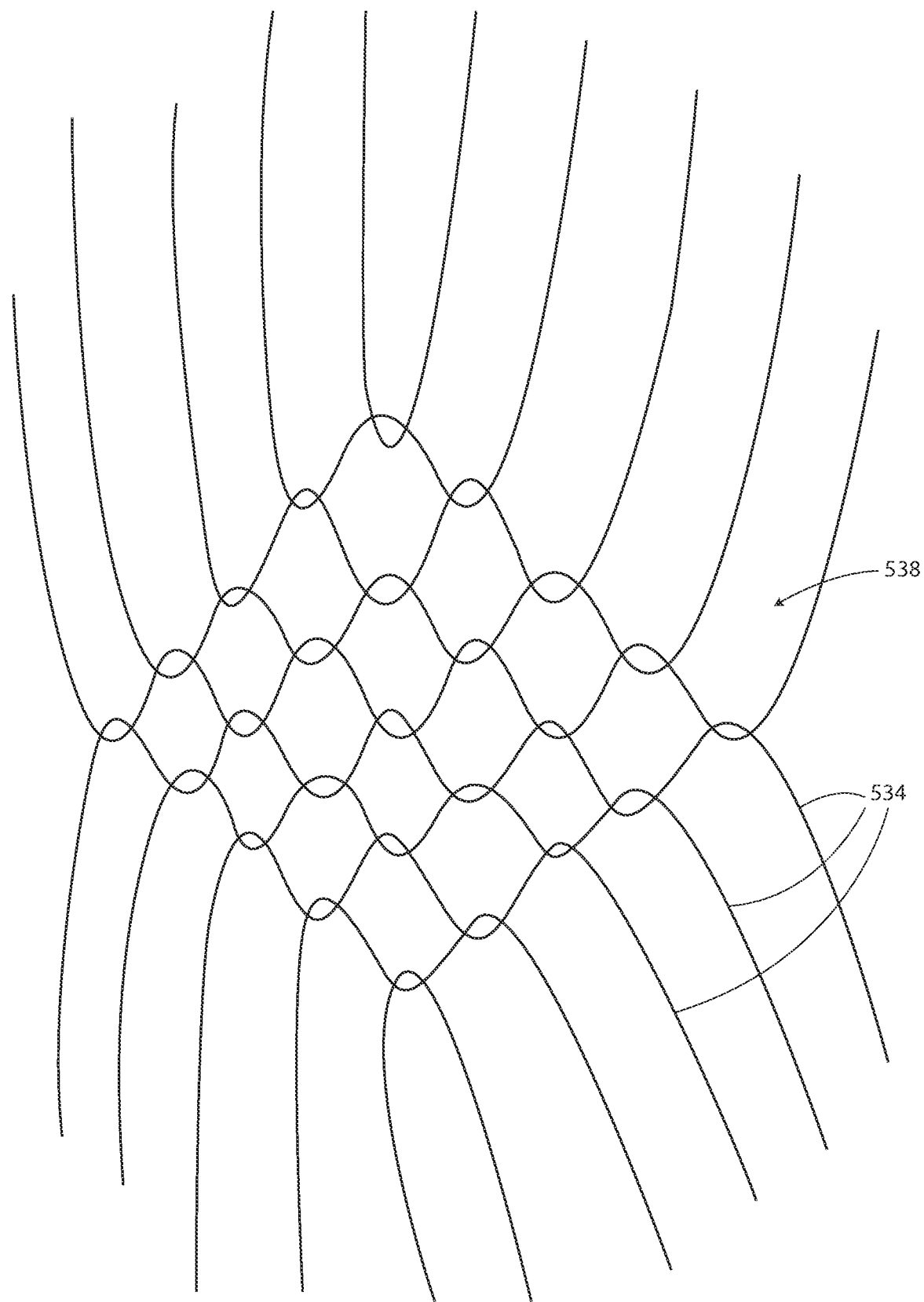
FIG. 36 is a perspective view of the basket weave result achieved through use of the invention, the basket weave being woven in place subcutaneously in the breast.
Figure 37:
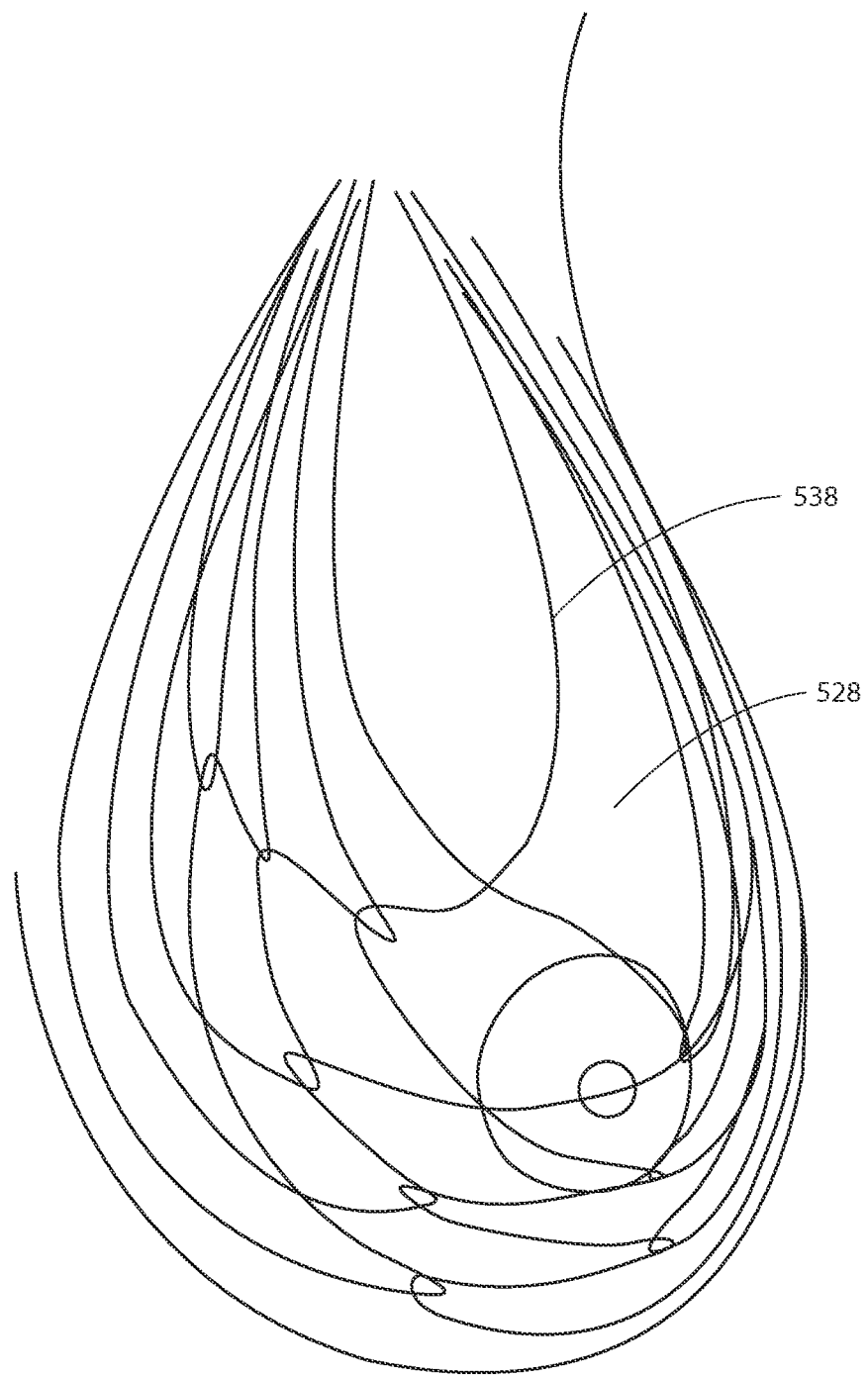
FIG. 37 is a perspective view, with the breast in phantom, depicting the basket weave in relation to the breast as it is formed inside the breast.
Figure 38:
FIG. 38 is a side view of the shuttle needle, with graduation marks near each end and a thread through a centrally located eye.
Figure 39:
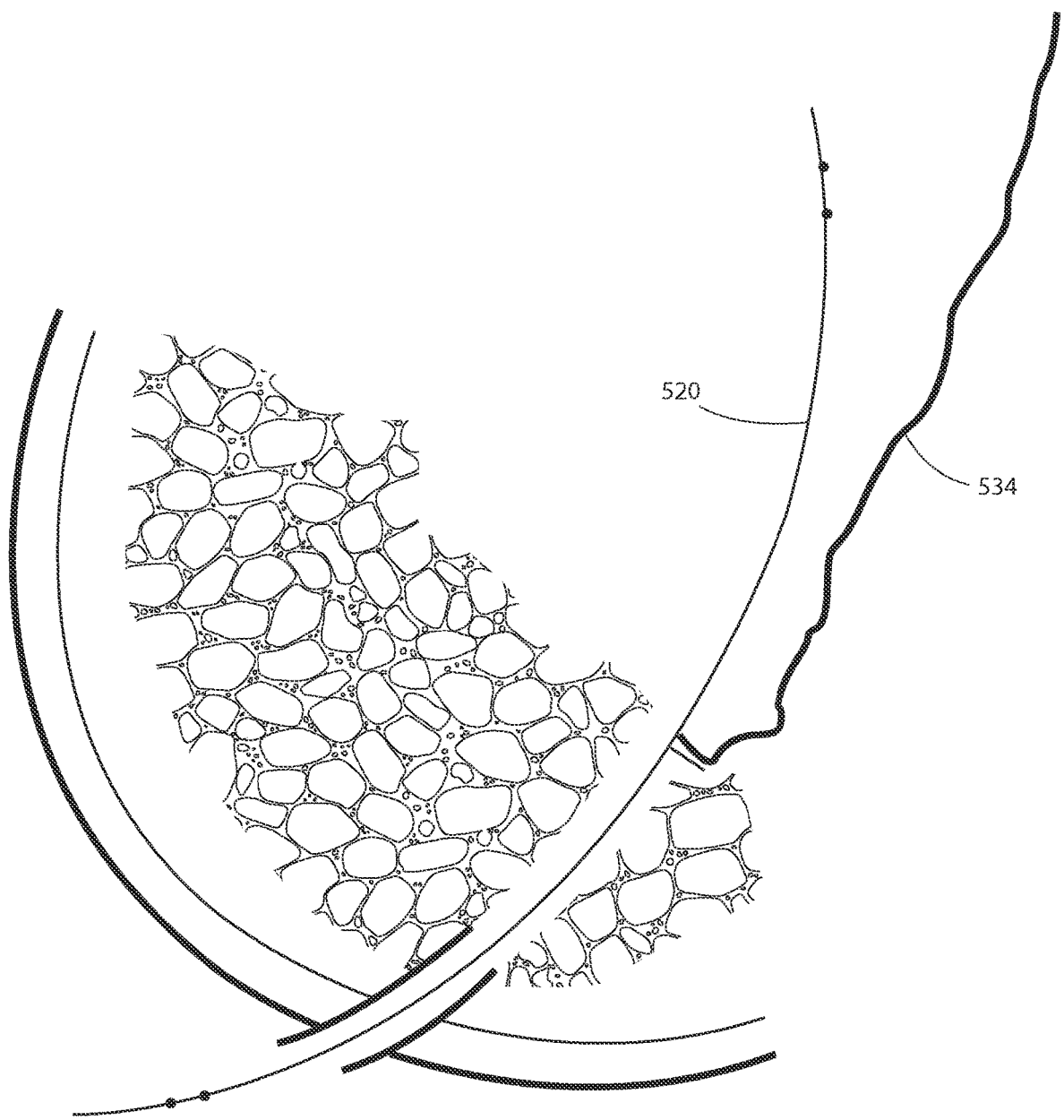
FIG. 39 is a cross sectional view of the breast with bra, and the needle inserted through one of the grommets and into the breast with a thread being threaded through the breast.
Figure 40:
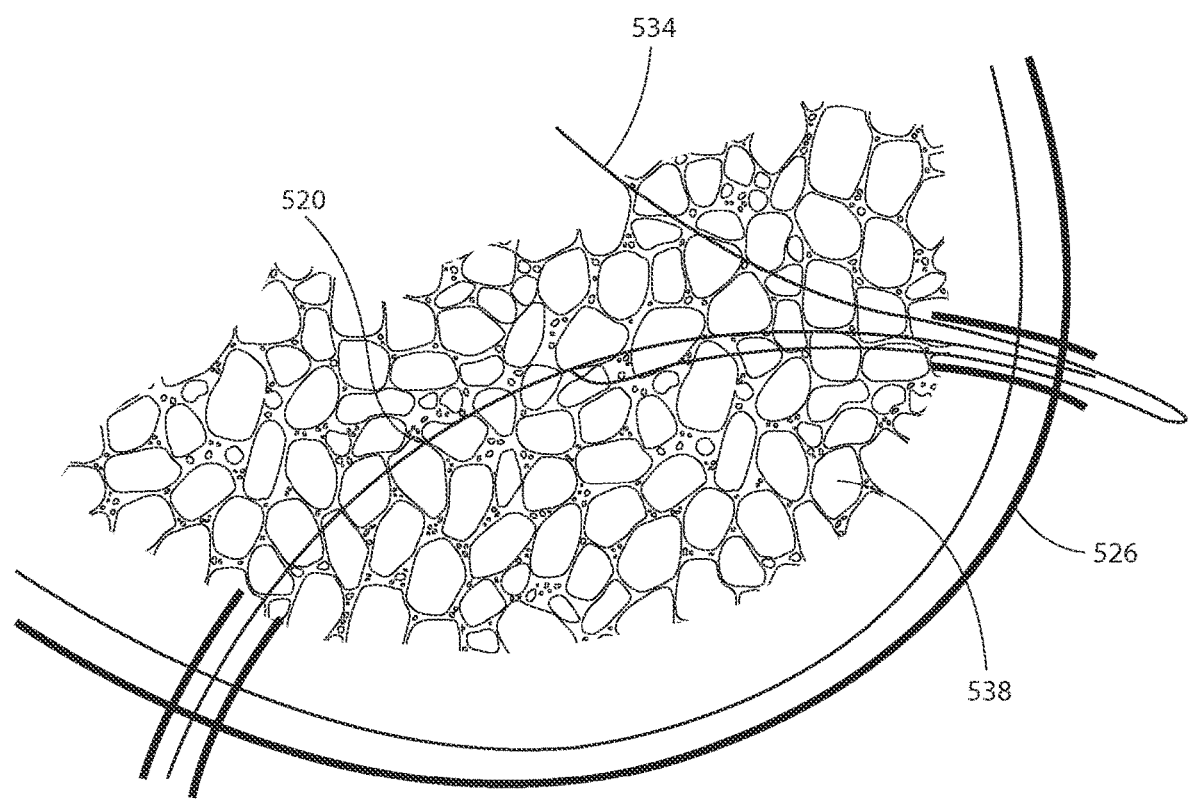
FIG. 40 is a cross sectional view of the shuttle needle inserted through grommets at each end and showing the thread looped through one of the grommets.
Figure 41:
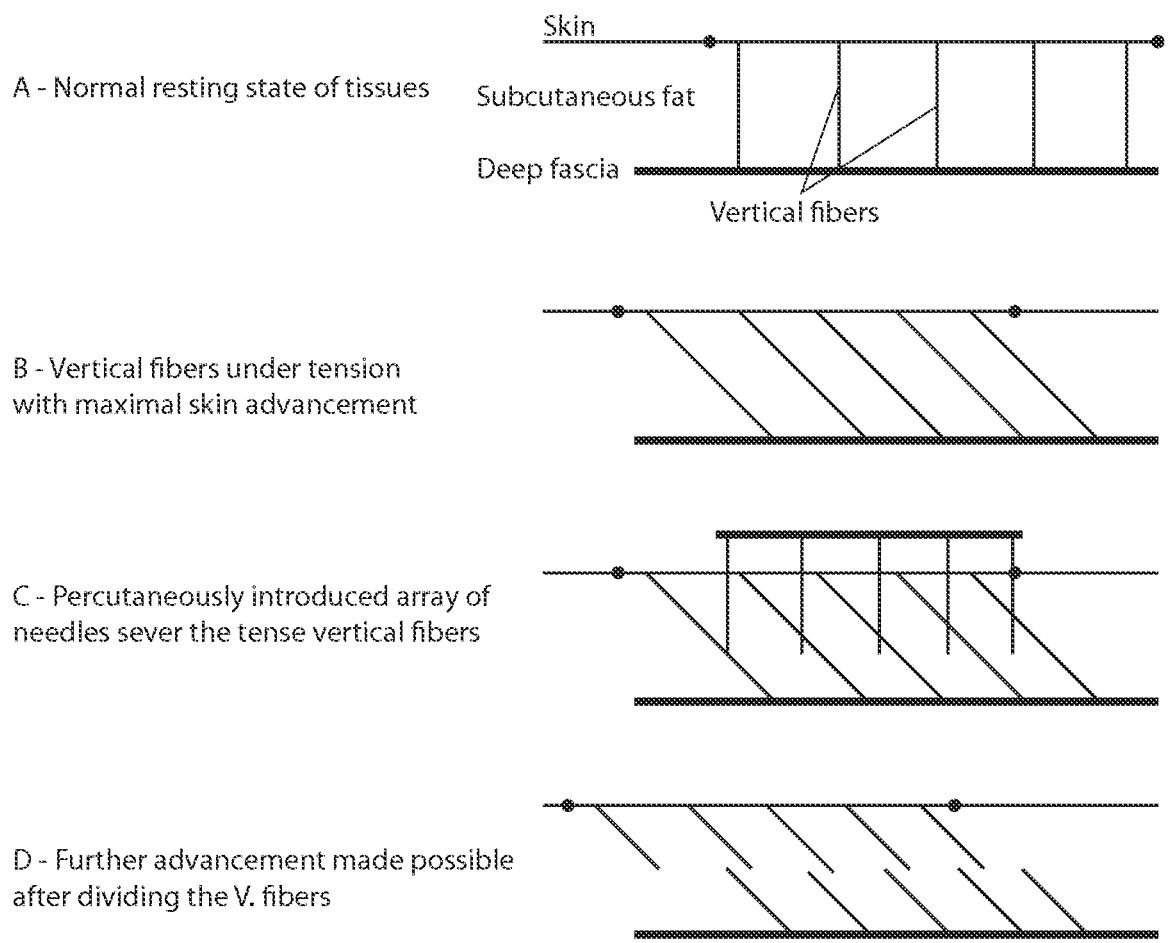
FIG. 41 depicts in several views the use of the Rigotome.

As shown in FIG. 34, a shuttle needle 520 is inserted through a grommet 522 inserted into a hole 524 in a bra 526 created by the needle 520 as it is passed through the bra 526 at points 527 marked along the bra 526 in a pattern, and with the bra 526 preferably adhered but at least close fitting to a breast 528. The shuttle needle 520 is used to form the basket weave (see below) within the breast 528, as explained in greater detail below. The shuttle needle 520 generally is formed in a curve with two ends 530 and a centrally located eye 532 through which one or more threads 534 are passed for weaving a supporting basket weave inside the breast 528. Although the inventor discloses a shuttle needle 520 as his preferred embodiment, other needles may be used so long as care is taken to loop the thread 534 and form the basket weave. Furthermore, the needles disclosed and described above may also be used, keeping in mind the teaching of this specification. FIG. 35 depicts an alternate design for a grommet 522 and which includes a shoulder 536 to better hold the grommet 528 in place in the bra 526 and prevent the needle 520 or tensioning of the thread 534 by continued weaving from inadvertently and prematurely pulling the thread 534 back inside the breast 528. FIG. 36 depicts the basket weave 538 which is formed inside the breast through use of the kit 540 of the invention, as explained below. Although the inventor prefers the interlocking basket weave construction depicted in FIG. 36, in would be understood by those of skill in the art that other patterns could be used to like effect and even specialized weaves to address and correct particular construction issues in a patient. FIG. 37 depicts the basket weave 538 inside the breast 528 to give a better idea of the relative size, location and spacing of the inventor's preferred basket weave 538. FIG. 38 depicts the shuttle needle 520 with its two ends 530 and centrally located eye 532. Also depicted are two sets of graduations 542 which are used by a surgeon as a guide and indicator as to the relative position of the needle inside the breast as the basket weave 538 is created. FIGS. 39 and 40 depict the shuttle needle 520 passing through the breast parenchyma as desired to anchor the basket weave 538, as explained below.

The kit described above is preferably used to surgically construct subcutaneously the "internal brassiere" as next described.

Technique for Use of the Kit

1—Preparation of the Breast:

The procedure preferably starts with tumescent diffuse injection of the subcutaneous tissue with dilute lipoaspirate containing adrenaline. The fluid in the injected dilute fat graft distends the subcutaneous plane making it easier to dissect while the fat grafts provide fill and glue & are a source of regenerative factors. While the procedure can be performed without fat injection, only with tumescent fluid containing adrenaline, the inventor prefers to add fat grafts or other regenerative reagents such as allograft preparations as most women also desire some additional volume augmentation. Furthermore, the inventor is aware of the regenerative properties of fat grafts and their ability to help correct contour defects.

Subcutaneous dissection of the skin away from the breast parenchyma allows the crucial re-draping of the skin over the breast parenchyma as the mastopexy will ultimately hold thanks to this re-draping and to the healing interface created by the dissection. This dissection is preferably done with a special cannula through a number of circum-mammary and circum-areolar needle puncture sites. This subdermal abrasion performed in this stage also in itself causes deep scarring and retraction of the stretched out skin.

Kit Components Used: A standard liposuction—dissecting injection cannula may be provided as part of the kit, but may also be readily available to most plastic and reconstructive surgeons and thus not provided as part of the kit.

2—Placement of Bra:

With the patient sitting as upright as possible on the operative table, nice fitting brassiere is preferably applied that restores the desired shape and position of the nipple areola complex. Once the ideal breast shape is reached, the breast is preferably suspended to the shoulders and the bra is preferably made to harden and stick to the skin such as by applying a hardening/gluing biocompatible material.

Kit Components Used: A sterile mesh fabric or initially stretchable material that can be formed into a nice fitting and supportive brassiere. A glue-like biocompatible compound that is preferably incorporated in the fabric, and which sticks & hardens. A bra that preferably stays semi-transparent with rubbery/plastic consistency with a pattern of thread weave preferably marked on the bra.

3—Weaving the Threads:

Through a small, approximately 0.5 cm incision at the clavicle, a bone anchor is inserted and through that same incision is passed the shuttle needles and threads. The needle preferably follows the weaving pattern outlined on the bra and a grommet/sleeve is preferably inserted at each needle exit/entry site. A small loop of thread is left outside (with a separate thread or small pin to prevent retraction of that loop as the thread continues to be weaved).

The depth of the sleeve/grommet is preferably adjusted to ensure that the thread weaves a brassiere mesh in the deeper tissues and does not grab the dermis and subdermal tissue.

The grommet/sleeve device has been found to permit the weaving of the internal bra. They insure that dermal fibers are not inadvertently caught as the needle comes in and out. The thread loops left outside allow the interlacing of the separate threads to create a weave that is then pulled deep inside as the threads are brought snugly together and the grommets are removed.

A total of 6-12 threads are preferably used depending upon the size of the breast, the degree of ptosis and the consistency of the breast (fatty loose breasts require more loops than the more parenchymal denser firmer breasts).

Kit Components Used: A long sharp curved needle (preferably shuttle type) which may be passed with a heavy needle holder. Grommets/needle sleeves, that stick out of the hardened conforming adherent bra to ensure that the weave is kept in the deeper tissues and that it is the deeper tissues that are suspended. Threads (preferable to have each thread color coded to follow its weave pattern and to couple them together at the time of tying). Threads non-resorbable (preferably use #1 Prolene). However a fascia/collagen based allograft or synthetic material that could regenerate tendon might also be preferable depending on the surgeon and the patient.

4—Completing the Suspension.

The threads are pulled with the same even gentle tension on all threads. It is considered important not to tighten too much but rather to just pull them snug to where there is no laxity in the thread. The thread should hold the position given to it by the bra.

The rigid adherent bra is considered important as it preserves and ensures the proper shape and prevents indents and unevenness in the breast. The contour of the breast has been found to be uneven if the loops do not have the proper length.

The inventor has found that the variable that perhaps is the most important is the length of the individual thread loops. This is determined by tying the knot or crimpling together the two ends of the thread. The supporting bra is the device that adjusts this variable. It insures that virtually the exact loop length is reached when the two ends are just snug while supported by the bra and not too tight so that the skin dimples inside the bra. This is the rationale behind having the bra device become rigid and adherent to the skin.

The transparent/translucent property of the bra allows inspection to ensure that the skin has not separated/unstuck itself from the bra if a loop is tied too tightly. Without this static support it would probably be difficult to get the exact tension on each one of the individual thread loops as they are tied/crimpled together. The Bra further ensures that the support is not dependent on the sutures—no dimples—no dermis or subdermis caught in the sutures and that we achieve an even suspension of the deeper tissues, allowing the dissected off skin to passively redrape.

A preferred alternative to tying the individual thread is a device that can crimple/lock them all together in one step. This also avoids having many sutures bulked together under the clavicle.

Kit Components Used: Crimpling/locking tool/device that connects all the threads together to the clavicle anchor.

5—Final Stage/Post Op Dressing:

Remove the adherent Bra and grommets. Simply close the small clavicle incision and inject some fat around the crimple site to camouflage the thread.

Apply a tagaderm type adherent dressing that supports the breast and immobilizes it for a few days to a couple of weeks till the repositioned skin heals in the desired position.

Other Additional Features:

1—Array of needle tips inserted through non-scar inducing tiny punctures selectively divide the vertical fibers that are under tensed by the forced advancement of the superficial tissue layers. The cuts are discrete and are at different levels such as to open no tissue plane and leave no cavities as the tissue advances.

Figure 44:
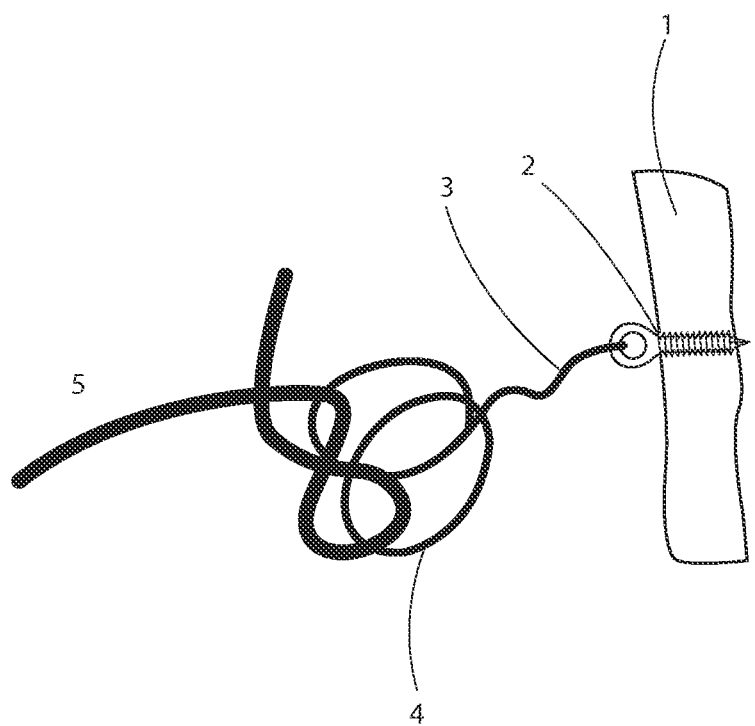
FIG. 44 depicts a clavicle suture fastening, fixture embodiment.

2—Belt like locking device consisting of two or more holes on a small band. The device is connected to the bone anchor. The holes might have winglets for added directional grabbing ability. The threads having completed the purse-string loop are inserted through the holes through a simple passage or a back and forth loop such that the tension can be adjusted and the sutures locked into place. Additionally, the device can be crimpled tight for a more secure hold; 1—outer cortex of the bone; 2—bone anchor inserted in the bone;

3—connector between anchor and locking device; 4—belt-like ring locking device that can also be crimpled for better locking strength; 5—threads having completed the purse-string suspension loop. See for example the embodiment depicted and as described above in FIG. 44.

Figure 43:
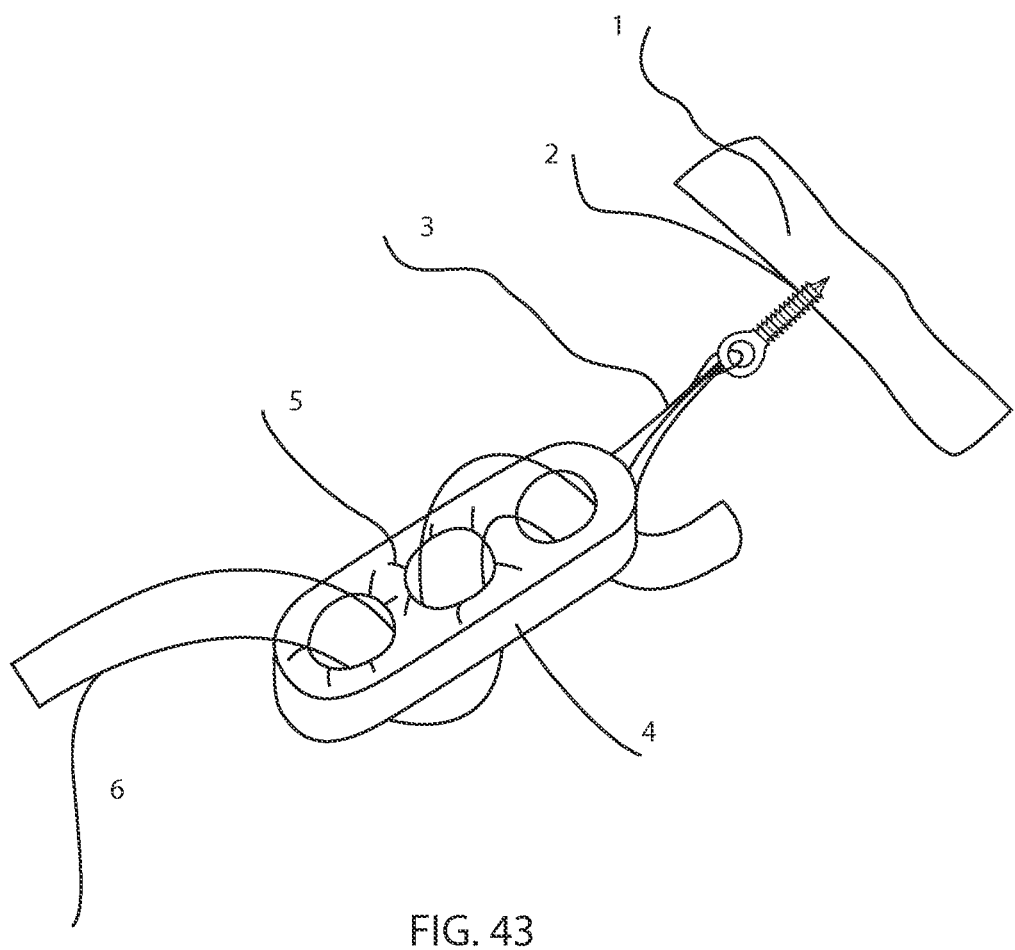
FIG. 43 depicts a clavicle suture fastening, double ring embodiment.

3—Belt like locking device consisting of two or rings. The device is connected to the bone anchor. The threads having completed the purse-string loop are inserted through the loops with back and forth loops such that the tension can be adjusted and the sutures locked into place. Additionally, the device can be crimpled tight for a more secure hold; 1—outer cortex of the bone; 2—bone anchor inserted in the bone; 3—connector between anchor and locking device; 4—washer slit winglets to directionally grab suture; 5—belt-like locking device that can also be crimpled for better locking strength; 6—threads having completed the purse-string suspension loop. See for example the embodiment depicted and as described above in FIG. 43.

Figure 45:
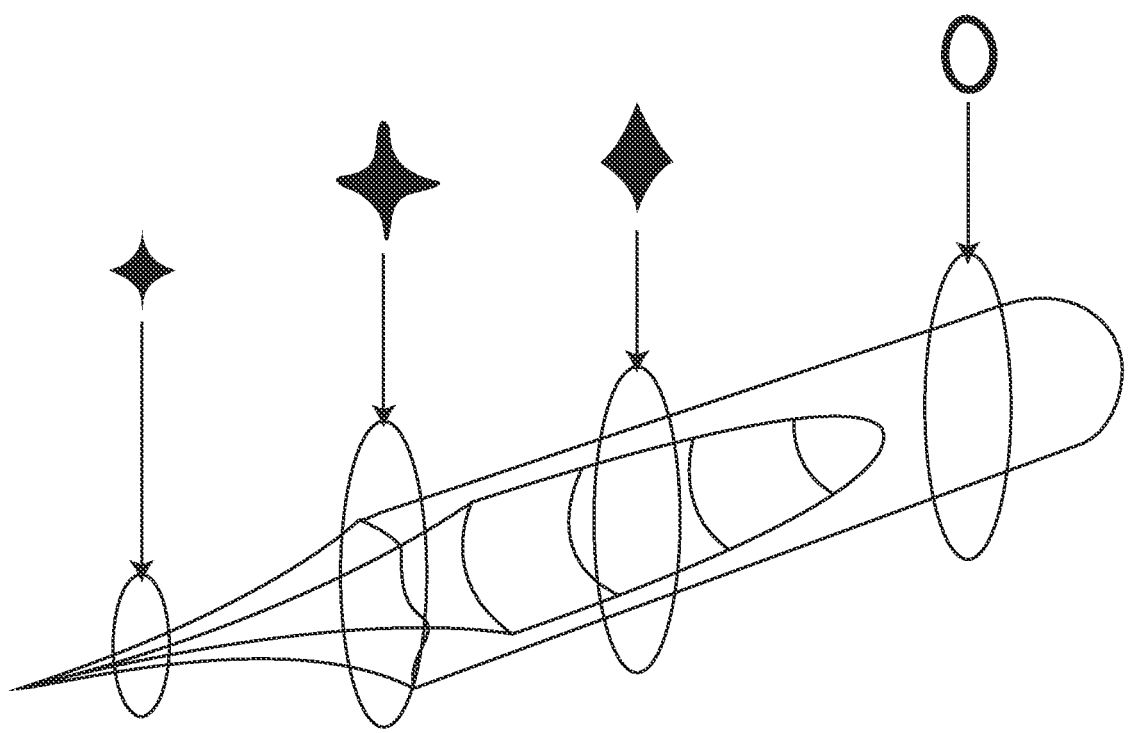
FIG. 45 depicts a needle embodiment with ailerons or wing extensions.

4—Alternative design of the "J" needle used for the RAFT procedure. The cutting sharp end of the needle has triangular or as shown has quadrangular winglets that facilitate maintaining the same plane of penetration along the tissue. The sharp pointed tip rapidly assumes a cross like configuration in cross section to eventually resume the rounded cross section of the needle shaft at the end of the long bevel. Inserts show the cross section at multiple levels. See for example the embodiment depicted and as described above in FIG. 45.

Figure 42:
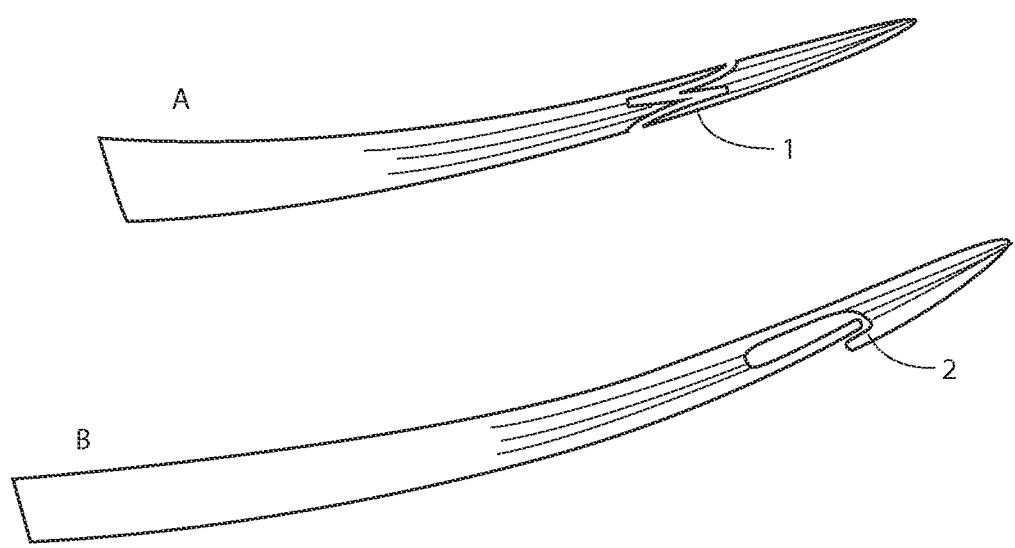
FIG. 42 depicts the needle with opening eye.

5—Design of needle with an eye that allows it to grab a suture loop or segment. A—key chain like spiral loop where the thread loop can be fed to end up locked inside the needle. 1 thread entrance site. B—slit gap that can be spring loaded to insert the suture loop into the eye of the needle. 2—thread entrance site. See for example the embodiment depicted and as described above in FIG. 42.

The principal advantages and features of the several related inventions have been disclosed and described illustratively in the preferred embodiments. However, as would be understood by those of skill in the art, the inventions are not limited to these illustrative embodiments and instead the inventor intends that the scope of his inventions be limited solely to the scope of the claims appended hereto, and their legal equivalents.

What is claimed is:

1. A double-pointed needle comprising:
an elongated body having a double J shape having a first end region, a second end region, and a central more linear region disposed between the first and second end regions;
the first end region of the elongated body forming a curved shape relative to the central region wherein the curved shape includes a sharp elongated cutting tip with a pointed end forming a blade to cut tissue along a curve and not upwardly to stay level and in a same plane throughout the curve;
the second end region of the elongated body forming a curved shape relative to the central region wherein the curved shape of the second end region includes a sharp elongated cutting tip with a pointed end forming a blade to cut tissue along the curve and not upwardly to stay level and in the same plane throughout the curve; and
an opening within the second end region for receiving a thread maintained in the same plane along the curve, the opening extending entirely transversely through the elongated body and at a fixed position through the elongated body and spaced from the central region, the opening being closer to the pointed end of the first region than to a midpoint of the needle.

2. The needle of claim 1, wherein the central region is straight.

3. The needle of claim 1, wherein the central region has a circular cross-section.

4. The needle of claim 1, wherein the opening disposed in the second end region includes a metal sleeve oriented around the opening.

5. The needle of claim 1, wherein the opening disposed in the second end region comprises a cross section that is different than a cross section of the central region.

6. The needle of claim 1, wherein the opening disposed in the second end region is formed of a non-linear passageway configured to hook a suture.

7. The needle of claim 1, wherein the opening disposed in the second end region includes a deflectable arm that, in a deflected state, forms a slot in a perimeter of the opening to allow a suture to pass through the slot and into the opening, and, in a non-deflected state, closes the slot to form a continuous perimeter of the opening.

8. The needle of claim 1, further comprising a second opening located at the first end region or the central region.

9. The needle of claim 1, wherein at least one of the first end region and the second end region includes at least one of a graduation mark, a groove, or a ring to indicate a depth of needle penetration.

10. The needle of claim 1, wherein the curved shape of the first end region has a first curvature that is different than a second curvature of the curved shape of the second end region.

11. The needle of claim 1, wherein the central region is curved in the same plane as the first and second end regions.

12. The needle of claim 1, wherein the opening is configured to be swaged such that the thread is secured in place.

13. The needle of claim 1, wherein the elongated body is 20-50 centimeters in length.

14. The needle of claim 1, wherein the elongated body has a diameter in the range of 1.5 to 3.5 millimeters.

15. The needle of claim 1, wherein at least a portion of the first end region is wider than the central region.

16. The needle of claim 1, wherein the cutting tip of the first end region and the cutting tip of the second end region have the same shape.

17. The needle of claim 1, wherein the cutting tip of the second end region comprises a cross section and only two cutting edges, the cross section having a long axis and a short axis, the long axis extending along the same plane as the curved shape of the second end region, the short axis being oriented perpendicular to the plane of the curved shape of the second end region, and the two cutting edges being disposed on opposite ends of the long axis and extending along the same plane as the curved shape of the second end region.

* * * * *